US010611778B2

(12) United States Patent
Angibaud et al.

(10) Patent No.: US 10,611,778 B2
(45) Date of Patent: Apr. 7, 2020

(54) FUSED BICYCLIC INHIBITORS OF MENIN-MLL INTERACTION

(71) Applicant: Janssen Pharmaceutica NV, Beerse (BE)

(72) Inventors: Patrick Rene Angibaud, Saint Pierre d'Autils (FR); Vineet Pande, Vosselaar (BE); Barbara Herkert, Flonheim (DE); Daniel Jason Krosky, Blue Bell, PA (US); Olivier Alexis Georges Querolle, Saint Vigor (FR); Aaron Nathaniel Patrick, Doylestown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/331,579

(22) PCT Filed: Sep. 13, 2017

(86) PCT No.: PCT/EP2017/073001
§ 371 (c)(1),
(2) Date: Mar. 8, 2019

(87) PCT Pub. No.: WO2018/050684
PCT Pub. Date: Mar. 22, 2018

(65) Prior Publication Data
US 2019/0218230 A1 Jul. 18, 2019

Related U.S. Application Data

(60) Provisional application No. 62/394,291, filed on Sep. 14, 2016.

(30) Foreign Application Priority Data

Oct. 5, 2016 (EP) .................................... 16192424
Jul. 7, 2017 (EP) .................................... 17180228

(51) Int. Cl.
*C07D 519/00* (2006.01)
*A61P 35/02* (2006.01)
*A61P 3/10* (2006.01)

(52) U.S. Cl.
CPC .............. *C07D 519/00* (2013.01); *A61P 3/10* (2018.01); *A61P 35/02* (2018.01)

(58) Field of Classification Search
CPC ....... C07D 519/00; C07D 519/04; A61P 3/10; A61P 35/02
USPC ........................................ 544/278; 514/260.1
See application file for complete search history.

(56) References Cited

U.S. PATENT DOCUMENTS

2014/0275070 A1  9/2014  Grembecka et al.

FOREIGN PATENT DOCUMENTS

| WO | WO 2011/029054 A1 | 3/2011 |
|----|-------------------|--------|
| WO | WO 2014/164543 A1 | 10/2014 |
| WO | WO 2015/191701 A1 | 12/2015 |
| WO | WO 2016/040330 A1 | 3/2016 |
| WO | WO 2016/081732 A1 | 5/2016 |
| WO | WO 2016/197027 A1 | 12/2016 |
| WO | WO 2017/112768 A1 | 6/2017 |
| WO | WO 2017/161002 A1 | 9/2017 |
| WO | WO 2017/161028 A1 | 9/2017 |
| WO | WO 2017/192543 A1 | 11/2017 |
| WO | WO 2017/207387 A1 | 12/2017 |
| WO | WO 2017/214367 A1 | 12/2017 |
| WO | WO 2018/024602 A1 | 2/2018 |
| WO | WO 2018/050684 A1 | 3/2018 |
| WO | WO 2018/050686 A1 | 3/2018 |
| WO | WO 2018/053267 A1 | 3/2018 |
| WO | WO 2018/109088 A1 | 6/2018 |
| WO | WO 2018/175746 A1 | 9/2018 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Simone, Introduction, Omenn, Cancer Prevention, Part XIV. Oncology, Cecil Textbook of Medicine, 20th Edition, vol. 1, pp. 1004-1010 (1996).*
Borkin, D., et al., "Pharmacologic Inhibition of the Menin-MLL Interaction Blocks Progression of MLL Leukemia In Vivo", Cancer Cell, 2015, pp. 589-602, vol. 27.
Borkin, D., et al., "Property Focused Structure-Based Optimization of Small Molecule Inhibitors of the Protein-Protein Interaction between Menin and Mixed Lineage Leukemia (MLL)", J. Med. Chem., 2016, pp. 892-913, vol. 59.
Cermakova, K., et al., "Validation and Structural Characterization of the LEDGF/p75-MLL Interface as a New Target for the Treatment of MLL-Dependent Leukemia", Cancer Research, 2014, pp. 5139-5151, vol. 15.
Charron, C.L., et al., "Recent developments in radiolabeled peptides for PET imaging of cancer", Tetrahedron Letters, 2016, pp. 4119-4127, vol. 57.
Chen, Ya-Xiong, et al., "The tumor suppressor menin regulates hematopoiesis and myeloid transformation by influencing Hox gene expression", PNAS, 2006, pp. 1018-1023, vol. 103, No. 4.
Cierpicki, T., et al., "Challenges and opportunities in targeting the menin-MLL interaction", Future Med. Chem, 2014, pp. 447-462, vol. 6, No. 4.

(Continued)

*Primary Examiner* — Deepak R Rao

(57) ABSTRACT

The present invention relates to pharmaceutical agents useful for therapy and/or prophylaxis in a mammal, and in particular to fused bicyclic compounds, pharmaceutical composition comprising such compounds, and their use as menin/MLL protein/protein interaction inhibitors, useful for treating diseases such as cancer, myelodysplastic syndrome (MDS) and diabetes.

10 Claims, No Drawings

Specification includes a Sequence Listing.

(56) References Cited

OTHER PUBLICATIONS

Grembecka, J., et al., "Menin-MLL inhibitors reverse oncogenic activity of MLL fusion proteins in leukemia", Nature Chemical Biology, 2012, pp. 277-284, vol. 8.
Greene, T.W., et al., "Greene's Protective Groups in Organic Synthesis", 4th ed., (2007), Wiley-Interscience, Hoboken, New Jersey.
He, S., et al., "High-Affinity Small-Molecule Inhibitors of the Menin-Mixed Lineage Leukemia (MLL) Interaction Closely Mimic a Natural Protein-Protein Interaction", J. Med. Chem., 2014, pp. 1543-1556, vol. 57.
Li, B.E., et al., "Distinct pathways regulated by menin and by MLL1 in hematopoietic stem cells and developing B cells", Blood, 2013, pp. 2039-2046, vol. 122, No. 12.
Malik, R., et al., "Targeting the MLL complex in castration-resistant prostate cancer", Nature Medicine, 2015, pp. 34-352, vol. 21, No. 4.
Marschalek, R., "Mechanisms of leukemogenesis by MLL fusion proteins", British Journal of Haematology, 2010, pp. 141-154, vol. 152, vol. 2.
Meyer, C., et al., "The MLL recombinome of acute leukemias in 2013", Leukemia, 2013, pp. 2165-2176, vol. 27.
Mishra, B.P., et al., "The Histone Methyltransferase Activity of MLL1 is Dispensable for Hematopoiesis and Leukemogenesis", Cell Reports, 2014, pp. 1239-1247, vol. 7.
Pantel, A.R., et al., "Molecular imaging to guide systematic career therapy: Illustrative examples of PET imaging cancer biomarkers", Cancer Letters, 2017, pp. 25-31, vol. 387.
Gennaro, A.R., Remington's 18th ed., Mack Publishing Company, (1990) see especially Part 8: Pharmaceutical preparations and their Manufacture, pp. 1435-1712.
Ren, J., et al., "Design and synthesis of benzylpiperidine inhibitors targeting the menin-MLL1 interface", Bioorganic & Medicinal Chemistry Letters, 2016, pp. 4472-4476, vol. 26.
Shah, S.K., et al., "Synthesis and evaluation of CCR5 antagonists containing modified 4-piperidinyl-2-phenyl-1-(phenylsulfonylamino)-butane", Bioorganic & Medicinal Chemistry Letters, 2005, pp. 977-982, vol. 15.
Thiel, A.T., et al., "Menin as a hub controlling mixed lineage leukemia", Bioessays, 2012, pp. 771-880, vol. 34.
Tomizawa, D., et al., "Repetitive Cycles of High-Dose Cytarabine Are Effective for Childhood Acute Myeloid Leukemia: Long-Term Outcome of the Children With AML Treated on Two Conservative Trials of Tokyo Children's Cancer Study Group", Pediatr Blood Cancer, 2007, pp. 127-132, vol. 49, No. 2.
Yokoyama, A., et al., "The Menin Tumor Suppressor Protein Is an Essential Oncogenic Cofactor for MLL-Associated Leukemogenesis", Cell, 2005, pp. 207-218, vol. 123.
Yokoyama, A., et al., "Menin Critically Links MLL Proteins with LEDGF on Cancer-Associated Target Genes", Cancer Cell, 2008, pp. 36-46, vol. 14.
International Search Report PCT/EP2017/073001 dated Nov. 6, 2017.
Written Opinion PCT/EP2017/073001 dated Nov. 6, 2017.
European Search Report EP17150502 completed Mar. 7, 2017.
European Search Report EP18201390 completed Nov. 14, 2018.
International Search Report PCT/EP2017/073004 dated Nov. 28, 2017.
International Search Report PCT/EP2017/082826 dated Feb. 14, 2018.
International Search Report PCT/CN2017/117536 dated Jul. 31, 2018.

\* cited by examiner

SEQUENCE LISTING

<160> NUMBER OF SEQ ID NOS: 1

<210> SEQ ID NO 1
<211> LENGTH: 616
<212> TYPE: PRT
<213> ORGANISM: Artificial Sequence
<220> FEATURE:
<223> OTHER INFORMATION: MENIN protein sequence with His tag

<400> SEQUENCE: 1

```
Met Gly Leu Lys Ala Ala Gln Lys Thr Leu Phe Pro Leu Arg Ser Ile
1               5                  10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
            180                 185                 190

Thr Ala Glu Val Thr Trp His Gly Lys Gly Asn Glu Asp Arg Arg Gly
        195                 200                 205
```

```
Gln Thr Val Asn Ala Gly Val Ala Glu Arg Ser Trp Leu Tyr Leu Lys
    210                 215                 220

Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
                245                 250                 255

Leu Gln Leu Gln Gln Lys Leu Leu Trp Leu Leu Tyr Asp Leu Gly His
            260                 265                 270

Leu Glu Arg Tyr Pro Met Ala Leu Gly Asn Leu Ala Asp Leu Glu Glu
        275                 280                 285

Leu Glu Pro Thr Pro Gly Arg Pro Asp Pro Leu Thr Leu Tyr His Lys
    290                 295                 300

Gly Ile Ala Ser Ala Lys Thr Tyr Tyr Arg Asp Glu His Ile Tyr Pro
305                 310                 315                 320

Tyr Met Tyr Leu Ala Gly Tyr His Cys Arg Asn Arg Asn Val Arg Glu
                325                 330                 335

Ala Leu Gln Ala Trp Ala Asp Thr Ala Thr Val Ile Gln Asp Tyr Asn
            340                 345                 350

Tyr Cys Arg Glu Asp Glu Glu Ile Tyr Lys Glu Phe Phe Glu Val Ala
        355                 360                 365

Asn Asp Val Ile Pro Asn Leu Leu Lys Glu Ala Ala Ser Leu Leu Glu
    370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
                405                 410                 415

Tyr Asp Gly Ile Cys Lys Trp Glu Glu Gly Ser Pro Thr Pro Val Leu
            420                 425                 430

His Val Gly Trp Ala Thr Phe Leu Val Gln Ser Leu Gly Arg Phe Glu
        435                 440                 445

Gly Gln Val Arg Gln Lys Val Arg Ile Val Ser Arg Glu Ala Glu Ala
    450                 455                 460

Ala Glu Ala Glu Glu Pro Trp Gly Glu Glu Ala Arg Glu Gly Arg Arg
465                 470                 475                 480

Arg Gly Pro Arg Arg Glu Ser Lys Pro Glu Glu Pro Pro Pro Pro Lys
                485                 490                 495

Lys Pro Ala Leu Asp Lys Gly Leu Gly Thr Gly Gln Gly Ala Val Ser
            500                 505                 510

Gly Pro Pro Arg Lys Pro Pro Gly Thr Val Ala Gly Thr Ala Arg Gly
        515                 520                 525

Pro Glu Gly Gly Ser Thr Ala Gln Val Pro Ala Pro Ala Ala Ser Pro
    530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
                565                 570                 575

Leu Gln Leu Thr Ala Gln Ser Gln Val Gln Met Lys Lys Gln Lys Val
            580                 585                 590

Ser Thr Pro Ser Asp Tyr Thr Leu Ser Phe Leu Lys Arg Gln Arg Lys
        595                 600                 605

Gly Leu His His His His His His
    610                 615
```

FUSED BICYCLIC INHIBITORS OF MENIN-MLL INTERACTION

CROSS-REFERENCE TO RELATED APPLICATIONS

This application is a U.S. national stage of PCT Application No. PCT/EP2017/073001, filed Sep. 13, 2017, which claims the benefit of priority of U.S. Patent Application No. 62/394,291, filed Sep. 14, 2016, and European Patent Application No. 16192424.6, filed Oct. 5, 2016, and European Patent Application No. 17180228.3, filed Jul. 7, 2017, all of which are incorporated by reference herein, in their entireties and for all purposes.

FIELD OF THE INVENTION

The present invention relates to pharmaceutical agents useful for therapy and/or prophylaxis in a mammal, and in particular to fused bicyclic compounds, pharmaceutical composition comprising such compounds, and their use as menin/MLL protein/protein interaction inhibitors, useful for treating diseases such as cancer, myelodysplastic syndrome (MDS) and diabetes.

BACKGROUND OF THE INVENTION

Chromosomal rearrangements affecting the mixed lineage leukemia gene (MLL; MLL1; KMT2A) result in aggressive acute leukemias across all age groups and still represent mostly incurable diseases emphasizing the urgent need for novel therapeutic approaches. Acute leukemias harboring these chromosomal translocations of MLL represent as lymphoid, myeloid or biphenotypic disease and constitute 5 to 10% of acute leukemias in adults and approximately 70% in infants (Marschalek, Br J Haematol 2011. 152(2), 141-54; Tomizawa et al., Pediatr Blood Cancer 2007. 49(2), 127-32).

MLL is a histone methyltransferase that methylates histone H3 on lysine 4 (H3K4) and functions in multiprotein complexes. Use of inducible loss-of-function alleles of Mll1 demonstrated that Mll1 plays an essential role in sustaining hematopoietic stem cells (HSCs) and developing B cells although its histone methyltransferase activity is dispensable for hematopoiesis (Mishra et al., Cell Rep 2011. 7(4), 1239-47).

Fusion of MLL with more than 60 different partners has been reported to date and has been associated with leukemia formation/progression (Meyer et al., Leukemia 2013. 27, 2165-2176). Interestingly, the SET (Su(var)3-9, enhancer of zeste, and trithorax) domain of MLL is not retained in chimeric proteins but is replaced by the fusion partner (Thiel et al., Bioessays 2012. 34, 771-80). Recruitment of chromatin modifying enzymes like Dot1L and/or the pTEFb complex by the fusion partner leads to enhanced transcription and transcriptional elongation of MLL target genes including HOXA genes (e.g. HOXA9) and the HOX cofactor MEIS1 as the most prominent ones. Aberrant expression of these genes in turn blocks hematopoietic differentiation and enhances proliferation.

Menin which is encoded by the Multiple Endocrine Neoplasia type 1 (MEN1) gene is expressed ubiquitously and is predominantly localized in the nucleus. It has been shown to interact with numerous proteins and is, therefore, involved in a variety of cellular processes. The best understood function of menin is its role as an oncogenic cofactor of MLL fusion proteins. Menin interacts with two motifs within the N-terminal fragment of MLL that is retained in all fusion proteins, MBM1 (menin-binding motif 1) and MBM2 (Thiel et al., Bioessays 2012. 34, 771-80). Menin/MLL interaction leads to the formation of a new interaction surface for lens epithelium-derived growth factor (LEDGF). Although MLL directly binds to LEDGF, menin is obligatory for the stable interaction between MLL and LEDGF and the gene specific chromatin recruitment of the MLL complex via the PWWP domain of LEDGF (Cermakova et al., Cancer Res 2014. 15, 5139-51; Yokoyama & Cleary, Cancer Cell 2008. 8, 36-46). Furthermore, numerous genetic studies have shown that menin is strictly required for oncogenic transformation by MLL fusion proteins suggesting the menin/MLL interaction as an attractive therapeutic target. For example, conditional deletion of Men1 prevents leukomogenesis in bone marrow progenitor cells ectopically expressing MLL fusions (Chen et al., Proc Natl Acad Sci 2006. 103, 1018-23). Similarly, genetic disruption of menin/MLL fusion interaction by loss-of-function mutations abrogates the oncogenic properties of the MLL fusion proteins, blocks the development of leukemia in vivo and releases the differentiation block of MLL-transformed leukemic blasts. These studies also showed that menin is required for the maintenance of HOX gene expression by MLL fusion proteins (Yokoyama et al., Cell 2005. 123, 207-18). In addition, small molecule inhibitors of menin/MLL interaction have been developed suggesting druggability of this protein/protein interaction and have also demonstrated efficacy in preclinical models of AML (Borkin et al., Cancer Cell 2015. 27, 589-602; Cierpicki and Grembecka, Future Med Chem 2014. 6, 447-462). Together with the observation that menin is not a requisite cofactor of MLL1 during normal hematopoiesis (Li et al., Blood 2013. 122, 2039-2046), these data validate the disruption of menin/MLL interaction as a promising new therapeutic approach for the treatment of MLL rearranged leukemia and other cancers with an active HOX/MEIS1 gene signature. For example, an internal partial tandem duplication (PTD) within the 5' region of the MLL gene represents another major aberration that is found predominantly in de novo and secondary AML as well as myeloid dysplasia syndromes. Although the molecular mechanism and the biological function of MLL-PTD is not well understood, new therapeutic targeting strategies affecting the menin/MLL interaction might also prove effective in the treatment of MLL-PTD-related leukemias. Furthermore, castration-resistant prostate cancer has been shown to be dependent on the menin/MLL interaction (Malik et al., Nat Med 2015. 21, 344-52).

Several references describe inhibitors targeting the menin-MLL interaction: WO2011029054, J Med. Chem 2016, 59, 892-913 describes the preparation of thienopyrimidine and benzodiazepine derivatives; WO2014164543 describes thienopyrimidine and thienopyridine derivatives; Nature Chemical Biology March 2012, 8, 277-284 and Ren, J.; et al. Bioorg Med Chem Lett (2016), http://dx.doi.org/10.1016/j.bmcl.2016.07.074 describe thienopyrimidine derivatives; J Med Chem 2014, 57, 1543-1556 describes hydroxy- and aminomethylpiperidine derivatives; and Future Med Chem 2014, 6, 447-462 reviews small molecule and peptidomimetic compounds.

DESCRIPTION OF THE INVENTION

The present invention concerns novel compounds of Formula (I)

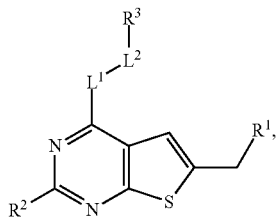

and the tautomers and the stereoisomeric forms thereof, wherein $R^1$ is selected from the group consisting of $CH_3$, $CH_2F$, $CHF_2$ and $CF_3$;

$R^2$ is selected from the group consisting of hydrogen and $CH_3$;

$L^1$ is a 7- to 9-membered fused heterocycle of Formula (a)

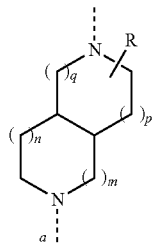

wherein a represents the position of linkage to the thienopyrimidinyl heterocycle;

m is equal to 0 or 1;

n is equal to 0 or 1;

p is equal to 0, 1 or 2;

q is equal to 0 or 1;

R is selected from the group consisting of hydrogen and oxo; and $L^2$-$R^3$ is selected from (a), (b), (c), (d) or (e), wherein (a) $L^2$ is selected from the group consisting of >$SO_2$, >$CR^{4a}R^{4b}$, and —$CHR^{4a}CHR^5$—; wherein $R^{4a}$ is selected from the group consisting of hydrogen; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;

$R^{4b}$ is selected from the group consisting of hydrogen and methyl; or $R^{4a}$ and $R^{4b}$ together with the carbon atom to which they are attached form a $C_{3-5}$cycloalkyl or a C-linked 4- to 6-membered heterocyclyl containing an oxygen atom;

$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom; wherein $R^6$, $R^{7a}$, $R^{7b}$, $R^8$, $R^{9a}$ and $R^{9b}$ are each independently selected from the group consisting of hydrogen; $C_{1-4}$alkyl optionally substituted with a substituent selected from the group consisting of fluoro, —CN and —C(=O)$NR^{10a}R^{10b}$; and $C_{2-4}$alkyl substituted with a substituent selected from the group consisting of —$OR^{11}$ and —$NR^{10a}R^{10b}$; wherein $R^{10a}$, $R^{10b}$ and $R^{11}$ are each independently selected from the group consisting of hydrogen; $C_{1-4}$alkyl; and C-linked 4- to 7-membered non-aromatic heterocyclyl containing at least one nitrogen, oxygen or sulfur atom; and $R^3$ is selected from the group consisting of Ar; $Het^1$; $Het^2$; and a 7- to 10-membered saturated spirocarbobicyclic system; or (b) $L^2$ is selected from >$CR^{4c}R^{4d}$ and —$CHR^{4c}CHR^{5a}$—; wherein $R^{4c}$, $R^{4d}$ and $R^{5a}$ are each independently selected from the group consisting of hydrogen and $C_{1-4}$alkyl; and $R^3$ is selected from the group consisting of

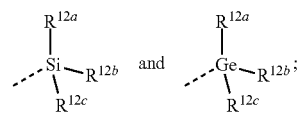

wherein $R^{12a}$, $R^{12b}$, and $R^{12c}$ are each independently selected from the group consisting of $C_{1-6}$alkyl optionally substituted with a —OH or a —$NH_2$ substituent; and —$OC_{1-6}$alkyl; or (c) -$L^2$-$R^3$ is $C_{1-6}$alkyl optionally substituted with one, two or three fluoro or —OH substituents; or (d) -$L^2$-$R^3$ is

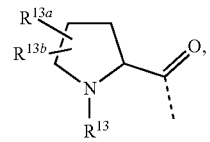

wherein $R^{13}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{14}$ and —$NR^{15a}R^{15b}$; wherein $R^{14}$, $R^{15a}$ and $R^{15b}$ are each independently selected from the group consisting of hydrogen; $C_{1-4}$alkyl optionally substituted with a substituent selected from the group consisting of fluoro, —CN, and —C(=O)$NR^{16a}R^{16b}$; $C_{2-4}$alkyl substituted with a substituent selected from the group consisting of —$OR^{17}$ and —$NR^{16a}R^{16b}$; and C-linked 4- to 7-membered non-aromatic heterocyclyl containing at least one nitrogen, oxygen or sulfur atom; wherein $R^{16a}$, $R^{16b}$ and $R^{17}$ are each independently selected from the group consisting of hydrogen and $C_{1-4}$alkyl; and $R^{13a}$ is selected from the group consisting of hydrogen, fluoro and $C_{1-4}$alkyl;

$R^{13b}$ is selected from the group consisting of hydrogen, fluoro, —$OC_{1-4}$alkyl, and $C_{1-4}$alkyl optionally substituted with 1, 2 or 3 fluoro substituents; or $R^{13a}$ and $R^{13b}$ are bound to the same carbon atom and together form a $C_{3-5}$cycloalkyl or a C-linked 4- to 6-membered heterocyclyl containing an oxygen atom; or (e) -L²-R³ is

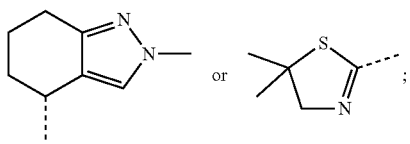

and wherein

Ar is phenyl or naphthyl, each of which may be optionally substituted with one, two, or three substituents each independently selected from the group consisting of halo, —CN, —OR$^{18}$, —NR$^{19a}$R$^{19b}$, and C$_{1-4}$alkyl optionally substituted with a substituent selected from the group consisting of fluoro, —CN, —OR$^{20}$, —NR$^{21a}$R$^{21b}$ and —C(=O)NR$^{21a}$R$^{21b}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —OR$^{18}$, —NR$^{19a}$R$^{19b}$, C$_{3-6}$cycloalkyl, and C$_{1-4}$alkyl optionally substituted with a substituent selected from the group consisting of fluoro, —CN, —OR$^{20}$, —NR$^{21a}$R$^{21b}$, and —C(=)NR$^{21a}$R$^{21b}$; and Het$^2$ is a non-aromatic heterocyclyl optionally substituted with one, two, or three substituents each independently selected from the group consisting of halo, —CN, —OR$^{18}$, —NR$^{19a}$R$^{19b}$, —C(=O)C$_{1-6}$alkyl, —C(=O)—O—C$_{1-6}$alkyl, —C(=O)—C$_{3-6}$cycloalkyl, —C(=O)—Ar$^2$, —C(=O)—Het$^3$, —C(=O)—Het$^4$, and C$_{1-4}$alkyl optionally substituted with a substituent selected from the group consisting of fluoro, —CN, —OR$^{20}$, —NR$^{21a}$R$^{21b}$, and —C(=O)NR$^{21a}$R$^{21b}$;

Ar$^2$ is phenyl;
Het$^3$ is pyridyl;
Het$^4$ is oxetanyl, tetrahydrofuranyl, or tetrahydropyranyl;
wherein R$^{18}$, R$^{19a}$, R$^{19b}$, R$^{20}$, R$^{21a}$, and R$^{21b}$ are each independently selected from the group consisting of hydrogen; C$_{1-4}$alkyl optionally substituted with a substituent selected from the group consisting of fluoro and —C(=O)NR$^{22a}$R$^{22b}$; and C$_{2-4}$alkyl substituted with a substituent selected from the group consisting of —OR$^{23}$ and —NR$^{22a}$R$^{22b}$; wherein R$^{22a}$, R$^{22b}$ and R$^{23}$ are each independently selected from the group consisting of hydrogen; C$_{1-4}$alkyl; and C-linked 4- to 7-membered non-aromatic heterocyclyl containing at least one nitrogen, oxygen or sulfur atom;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, myelodysplastic syndrome (MDS) and diabetes.

In a particular embodiment, the invention relates to a compound of Formula (I), a pharmaceutically acceptable salt, or a solvate thereof, for use in the treatment or in the prevention of cancer.

In a specific embodiment said cancer is selected from leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

The invention also relates to the use of a compound of Formula (I), a pharmaceutically acceptable salt, or a solvate thereof, in combination with an additional pharmaceutical agent for use in the treatment or prevention of cancer, myelodysplastic syndrome (MDS) and diabetes.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, myelodysplastic syndrome (MDS) and diabetes.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix 'C$_{x-y}$' (where x and y are integers) as used herein refers to the number of carbon atoms in a given group. Thus, a C$_{1-6}$alkyl group contains from 1 to 6 carbon atoms, a C$_{3-6}$cycloalkyl group contains from 3 to 6 carbon atoms, and so on.

The term 'C$_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term 'C$_{2-4}$alkyl' as used herein as a group or part of a group represents a straight or branched chain saturated hydrocarbon radical having from 2 to 4 carbon atoms, such as ethyl, n-propyl, isopropyl, n-butyl, s-butyl, t-butyl and the like.

The term 'C$_{1-6}$alkyl' as used herein as a group or part of a group represents a straight or branched chain saturated hydrocarbon radical having from 1 to 6 carbon atoms such as the groups defined for C$_{1-4}$alkyl and n-pentyl, n-hexyl, 2-methylbutyl and the like.

The term 'C$_{3-5}$cycloalkyl' as used herein as a group or part of a group defines a saturated, cyclic hydrocarbon radical having from 3 to 5 carbon atoms, such as cyclopropyl, cyclobutyl and cyclopentyl.

The term 'C$_{3-6}$cycloalkyl' as used herein as a group or part of a group defines a saturated, cyclic hydrocarbon radical having from 3 to 6 carbon atoms, such as cyclopropyl, cyclobutyl, cyclopentyl and cyclohexyl.

'Oxo' represents =O.

As used herein 'spiro bicyclic' systems are cyclic systems wherein two cycles are joined at a single atom. Examples of 7- to 10-membered saturated spirocarbobicyclic systems include, but are not limited to

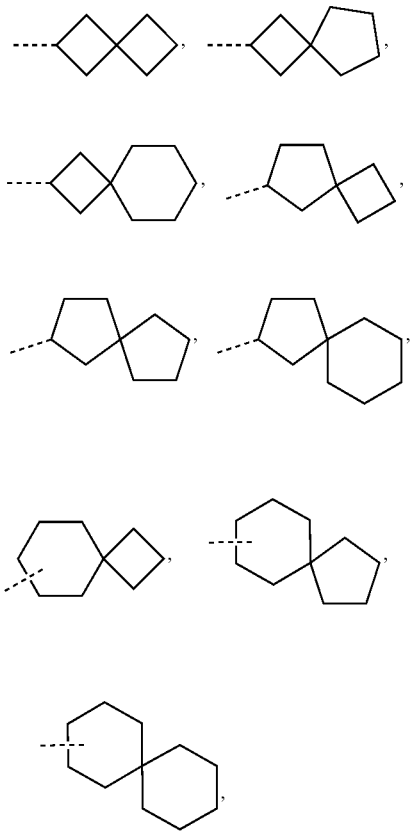

and the like.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection froth the indicated group, provided that the normal valency is not exceeded, and that the substitution results in a chemically stable compound, i.e. a compound that is sufficiently robust to survive isolation to a useful degree of purity from a reaction mixture.

Combinations of substituents and/or variables are permissible only if such combinations result in chemically stable compounds. 'Stable compound' is meant to indicate a compound that is sufficiently robust to survive isolation to a useful degree of purity from a reaction mixture.

The skilled person will understand that when an atom or radical is substituted with 'a substituent', it is meant that the atom or radical referred to is substituted with one substituent selected from the indicated group.

The skilled person will understand that the term 'optionally substituted' means that the atom or radical indicated in the expression using 'optionally substituted' may or may not be substituted (this means substituted or unsubstituted respectively).

When two or more substituents are present on a moiety they may, where possible and unless otherwise indicated or clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent).

Within the context of this invention 'saturated' means 'fully saturated', if not otherwise specified.

A 'non-aromatic group' embraces unsaturated ring systems without aromatic character, partially saturated and fully saturated carbocyclic and heterocyclic ring systems. The term 'partially saturated' refers to rings wherein the ring structure(s) contain(s) at least one multiple bond e.g. a C=C, N=C bond. The term 'fully saturated' refers to rings where there are no multiple bonds between ring atoms. Thus, a 'non-aromatic heterocyclyl' is a non-aromatic monocyclic or bicyclic system, unless otherwise specified, having for example, 3 to 12 ring members, more usually 5 to 10 ring members. Examples of monocyclic groups are groups containing 4 to 7 ring members, more usually, 5 or 6 ring members. Examples of bicyclic groups are those containing 8 to 12, more usually 9 or 10 ring members.

Non-limiting examples of monocyclic heterocyclyl systems containing at least one heteroatom selected from nitrogen, oxygen or sulfur (N, O, S) include, but are not limited to 4- to 7-membered heterocyclyl systems such as azetidinyl, oxetanyl, pyrrolidinyl, tetrahydrofuranyl, piperidinyl, piperazinyl, pyranyl, dihydropyranyl, tetrahydropyranyl, morpholinyl, thiomorpholinyl. Non-limiting examples of bicyclic heterocyclyl systems containing at least one heteroatom selected from nitrogen, oxygen or sulfur (N, O, S) include, but are not limited to octahydro-1H-indolyl, indolinyl,

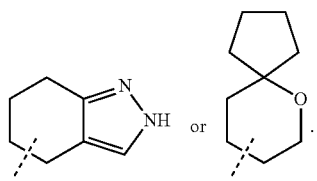

Unless otherwise specified, each can be bound to the remainder of the molecule of Formula (I) through any available ring carbon atom (C-linked) or nitrogen atom (N-linked), and may optionally be substituted, where possible, on carbon and/or nitrogen atoms according to the embodiments.

Examples of a C-linked 4- to 7-membered non-aromatic heterocyclyl containing at least one nitrogen atom include, but are not limited to, azetidinyl, pyrrolidinyl and piperidinyl, bound to the rest of the molecule through an available carbon atom.

The term 'C-linked 4- to 6-membered heterocyclyl containing an oxygen atom' as used herein alone or as part of another group, defines a saturated, cyclic hydrocarbon radical containing an oxygen atom having from 4 to 6 ring members, such as oxetanyl, tetrahydrofuranyl, and tetrahydropyranyl.

Whenever substituents are represented by chemical structure, '---' represents the bond of attachment to the remainder of the molecule of Formula (I).

Lines (such as '---') drawn into ring systems indicate that the bond may be attached to any of the suitable ring atoms.

Het$^1$, Het$^2$ and Het$^3$ may be attached to the remainder of the molecule of Formula (I) through any available ring carbon or nitrogen atom as appropriate, if not otherwise specified.

It will be clear that a saturated cyclic moiety may, where possible, have substituents on both carbon and N-atoms, unless otherwise is indicated or is clear from the context.

It will be clear that when L$^2$ is >SO$_2$, this is equivalent to L$^2$ is —SO$_2$—. It will be clear that when L$^2$ is >CR$^{4a}$R$^{4b}$, this is equivalent to L is

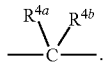

For example, in compound 1, L$^2$ is >CR$^{4a}$R$^{4b}$ wherein both R$^{4a}$ and R$^{4b}$ are hydrogen.

Similar, it will be clear that when L$^2$ is >CR$^{4c}$R$^{4d}$, this is equivalent to L is

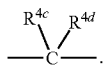

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

For example

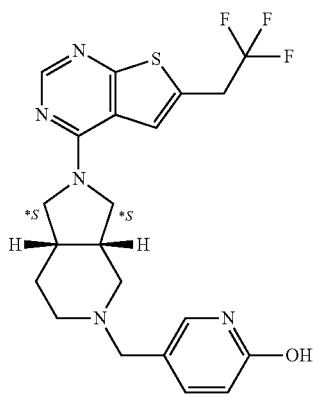 [SMILES: Oc1ccc(CN2CC[C@@H]3CN(c4ncnc5sc(CC(F)(F)F)cc45)C[C@@H]3C2)cn1]

also covers the other tautomeric form

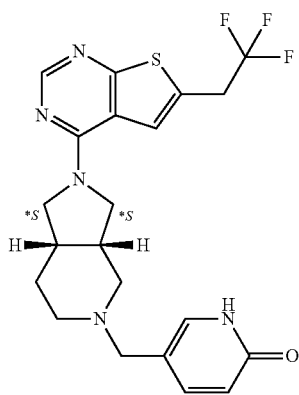 [SMILES: O=c1ccc(CN2CC[C@@H]3CN(c4ncnc5sc(CC(F)(F)F)cc45)C[C@@H]3C2)c[nH]1]

Pharmaceutically acceptable salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable salts as mentioned hereinabove or hereinafter are meant to comprise the therapeutically active non-toxic acid and base salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluene-sulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts; and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^2$H. In particular, deuterated compounds are intended to be included within the scope of the present invention.

Certain isotopically-labeled compounds of the present invention (e.g., those labeled with $^3$H and $^{14}$C) may be useful for example in substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H may afford certain therapeutic advantages resulting from greater metabolic stability (e.g., increased in vivo half-life or reduced dosage requirements) and hence may be preferred in some circumstances. Thus, in a particular embodiment of the present invention, $R^2$ is selected from hydrogen or deuterium, in particular deuterium. In another embodiment, $L^2$ can be >C($^2$H)$_2$. Positron emitting isotopes such as $^{15}$O, $^{13}$N, $^{11}$C and $^{18}$F are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$R^2$ is selected from the group consisting of hydrogen and $CH_3$;

$L^1$ is a 7- to 9-membered fused heterocycle of Formula (a)

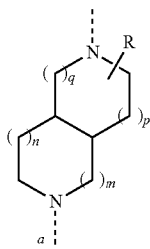

(a)

wherein
a represents the position of linkage to the thienopyrimidinyl heterocycle;
m is equal to 0 or 1;
n is equal to 0 or 1;
p is equal to 0, 1 or 2;
q is equal to 0 or 1;
R is selected from the group consisting of hydrogen and oxo; and
-$L^2$-$R^3$ is selected from (a), (b), (c), (d) or (e), wherein
(a) $L^2$ is selected from the group consisting of >SO$_2$, >CR$^{4a}$R$^{4b}$, and —CHR$^{4a}$CHR$^5$—;

wherein
$R^{4a}$ is selected from the group consisting of hydrogen; —C(=O)NR$^{7a}$R$^{7b}$; C$_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;
$R^{4b}$ is selected from the group consisting of hydrogen and methyl; or
$R^{4a}$ and $R^{4b}$ together with the carbon atom to which they are attached form a C$_{3-5}$cycloalkyl or a C-linked 4- to 6-membered heterocyclyl containing an oxygen atom;
$R^5$ is selected from the group consisting of hydrogen; —OR$^6$; —NR$^{7a}$R$^{7b}$; —C(=O)NR$^{7a}$R$^{7b}$; C$_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;
wherein
$R^6$, $R^{7a}$, $R^{7b}$, $R^8$, $R^{9a}$ and $R^{9b}$ are each independently selected from the group consisting of hydrogen; C$_{1-4}$alkyl optionally substituted with a substituent selected from the group consisting of fluoro, —CN and —C(=O)NR$^{10a}$R$^{10b}$; and C$_{2-4}$alkyl substituted with a substituent selected from the group consisting of —OR$^{11}$ and —NR$^{10a}$R$^{10b}$;
wherein
$R^{10a}$, $R^{10b}$ and $R^{11}$ are each independently selected from the group consisting of hydrogen; C$_{1-4}$alkyl; and C-linked 4- to 7-membered non-aromatic heterocyclyl containing at least one nitrogen, oxygen or sulfur atom; and
$R^3$ is selected from the group consisting of Ar; Het$^1$; Het$^2$; and a 7- to 10-membered saturated spirocarbobicyclic system; or
(b) $L^2$ is selected from >CR$^{4c}$R$^{4d}$ and —CHR$^{4c}$CHR$^{5a}$—; wherein $R^{4c}$, $R^{4d}$ and $R^{5a}$ are each independently selected from the group consisting of hydrogen and C$_{1-4}$alkyl; and
$R^3$ is selected from the group consisting of

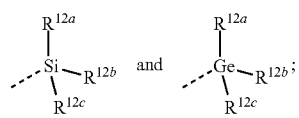

wherein
$R^{12a}$, $R^{12b}$ and $R^{12c}$ are each independently selected from the group consisting of C$_{1-6}$alkyl optionally substituted with a —OH or a —NH$_2$ substituent; and —OC$_{1-6}$alkyl; or
(c) -$L^2$-$R^3$ is C$_{1-6}$alkyl optionally substituted with one, two or three fluoro substituents; or
(d) -$L^2$-$R^3$ is

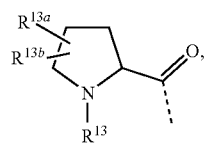

wherein
R$^{13}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{11}$ and —NR$^{15a}$R$^{15b}$, wherein R$^{14}$, R$^{15a}$ and R$^{15b}$ are each independently selected from the group consisting of hydrogen; C$_{1-4}$alkyl optionally substituted with a substituent selected from the group consisting of fluoro, —CN, and —C(=O)NR$^{16a}$R$^{16b}$; C$_{2-4}$alkyl substituted with a substituent selected from the group consisting of —OR$^{17}$ and —NR$^{16a}$R$^{16b}$; and C-linked 4- to 7-membered non-aromatic heterocyclyl containing at least one nitrogen, oxygen or sulfur atom; wherein R$^{16a}$, R$^{16b}$ and R$^{17}$ are each independently selected from the group consisting of hydrogen and C$_{1-4}$alkyl; and R$^{13a}$ is selected from the group consisting of hydrogen, fluoro and C$_{1-4}$alkyl;

R$^{13b}$ is selected from the group consisting of fluoro, —OC$_{1-4}$alkyl, and C$_{1-4}$alkyl optionally substituted with 1, 2 or 3 fluoro substituents; or R$^{13a}$ and R$^{13b}$ are bound to the same carbon atom and together form a C$_{3-5}$cycloalkyl or a C-linked 4- to 6-membered heterocyclyl containing an oxygen atom; or (e) -L$^2$-R$^3$ is

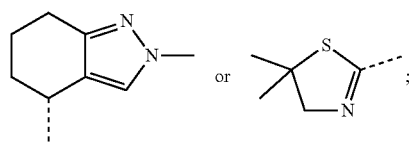

and wherein
Ar is phenyl or naphthyl, each of which may be optionally substituted with one, two, or three substituents each independently selected from the group consisting of halo, —CN, —OR$^{18}$, —NR$^{19a}$R$^{19b}$, and C$_{1-4}$alkyl optionally substituted with a substituent selected from the group consisting of fluoro, —CN, —OR$^{20}$, —NR$^{21a}$R$^{21b}$ and —C(=O)NR$^{21a}$R$^{21b}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —OR$^{18}$, —NR$^{19a}$R$^{19b}$, and C$_{1-4}$alkyl optionally substituted with a substituent selected from the group consisting of fluoro, —CN, —OR$^{20}$, —NR$^{21a}$R$^{21b}$, and —C(=O)NR$^{21a}$R$^{21b}$; and Het$^2$ is a non-aromatic heterocyclyl optionally substituted with one, two, or three substituents each independently selected from the group consisting of halo, —CN, —OR$^{18}$, —NR$^{19a}$R$^{19b}$, and C$_{1-4}$alkyl optionally substituted with a substituent selected from the group consisting of fluoro, —CN, —OR$^{20}$, —NR$^{21a}$R$^{21b}$, and —C(=O)NR$^{21a}$R$^{21b}$;

wherein
R$^{18}$, R$^{19a}$, R$^{19b}$, R$^{20}$, R$^{21a}$, and R$^{21b}$ are each independently selected from the group consisting of hydrogen; C$_{1-4}$alkyl optionally substituted with a substituent selected from the group consisting of fluoro and —C(=O)NR$^{22a}$R$^{22b}$; and C$_{2-4}$alkyl substituted with a substituent selected from the group consisting of —OR$^{23}$ and —NR$^{22a}$R$^{22b}$; wherein R$^{22a}$, R$^{22b}$ and R$^{23}$ are each independently selected from the group consisting of hydrogen; C$_{1-4}$alkyl; and C-linked 4- to 7-membered non-aromatic heterocyclyl containing at least one nitrogen, oxygen or sulfur atom;

and the pharmaceutically acceptable salts and the solvates thereof.

The present invention relates in particular to compounds of Formula (I) as defined herein, and the tautomers and the stereoisomeric forms thereof, wherein R$^1$ is selected from the group consisting of CF$_3$;
R$^2$ is selected from the group consisting of hydrogen;
L$^1$ is a 7- to 9-membered fused heterocycle of Formula (a)

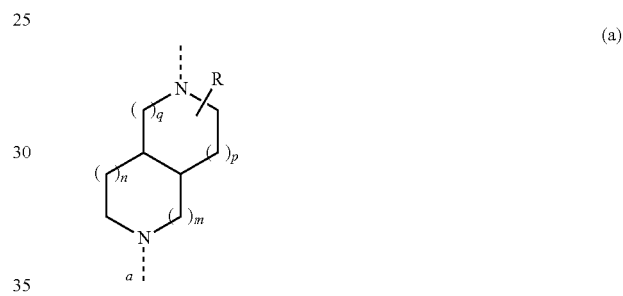

wherein
a represents the position of linkage to the thienopyrimidinyl heterocycle;
m is equal to 0 or 1;
n is equal to 0 or 1;
p is equal to 0, 1 or 2;
q is equal to 0 or 1;
R is selected from the group consisting of hydrogen and oxo; and
-L$^2$-R$^3$ is selected from (a), (b), (c) or (d) wherein
(a) L$^2$ is selected from the group consisting of >SO$_2$, >CR$^{4a}$R$^{4b}$ and —CHR$^{4a}$CHR$^5$—;
wherein
R$^{4a}$ is selected from the group consisting of hydrogen and C$_{1-4}$alkyl;
R$^{4b}$ is hydrogen; o
R$^5$ is selected from the group consisting of hydrogen and C$_{1-4}$alkyl; and
R$^3$ is selected from the group consisting of Ar; Het$^1$; and Het$^2$; or
(b) L$^2$ is >CR$^{4c}$R$^{4d}$; wherein R$^{4c}$ and R$^{4d}$ are hydrogen; and
R$^3$ is

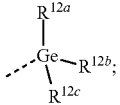

wherein
R$^{12a}$, R$^{12b}$, and R$^{12c}$ are C$_{1-6}$alkyl; or
(c) -L$^2$-R$^3$ is C$_{1-6}$alkyl optionally substituted with one, two or three fluoro or —OH substituents; or
(d) -L$^2$-R$^3$ is

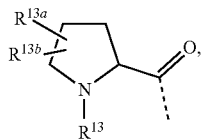

wherein
R$^{13}$ is hydrogen; and
R$^{13a}$ is hydrogen;
R$^{13b}$ hydrogen; or
R$^{13a}$ and R$^{13b}$ are bound to the same carbon atom and together form a C$_{3-5}$cycloalkyl;
Ar is phenyl which may be optionally substituted with one, two, or three substituents each independently selected from halo;
Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^{18}$, —NR$^{19a}$R$^{19b}$, C$_{3-6}$cycloalkyl, and C$_{1-4}$alkyl optionally substituted with a substituent selected from the group consisting of —OR$^{20}$, and —NR$^{21a}$R$^{21b}$; and
Het$^2$ is a non-aromatic heterocyclyl optionally substituted with one, two, or three substituents each independently selected from the group consisting of halo, —OR$^{18}$, —C(=O)—O—C$_{1-6}$alkyl, —C(=O)—Ar$^2$, —C(=O)—Het$^3$, and —C(=O)—Het$^4$;
Ar$^2$ is phenyl;
Het$^3$ is pyridyl;
Het$^4$ is oxetanyl, or tetrahydropyranyl;
wherein
R$^{18}$, R$^{20}$, R$^{21a}$, and R$^{21b}$ are each independently selected from the group consisting of hydrogen; and C$_{1-4}$alkyl;
and the pharmaceutically acceptable salts and the solvates thereof.

The present invention relates in particular to compounds of Formula (I) as defined herein, and the tautomers and the stereoisomeric forms thereof, wherein
(a) L$^2$ is selected from the group consisting of >SO$_2$, >CR$^{4a}$R$^{4b}$, and —CHR$^{4a}$CHR$^5$—;
wherein
R$^{4a}$ is selected from the group consisting of hydrogen; —C(=O)NR$^{7a}$R$^{7b}$; C$_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom;
R$^{4b}$ is selected from the group consisting of hydrogen and methyl; or
R$^{4a}$ and R$^{4b}$ together with the carbon atom to which they are attached form a C$_{3-5}$cycloalkyl or a C-linked 4- to 6-membered heterocyclyl containing an oxygen atom;
R$^5$ is selected from the group consisting of hydrogen; —OR$^6$; —NR$^{7a}$R$^{7b}$; —C(=O)NR$^{7a}$R$^{7b}$; C$_{1-4}$alkyl optionally substituted with a substituent selected from the group consisting of fluoro, —CN, —OR$^8$, and —NR$^{9a}$R$^{9b}$; and C-linked 4- to 7-membered non-aromatic heterocyclyl containing at least one nitrogen, oxygen or sulfur atom; wherein
R$^6$, R$^{7a}$, R$^{7b}$, R$^8$, R$^{9a}$ and R$^{9b}$ are each independently selected from the group consisting of hydrogen; C$_{1-4}$alkyl optionally substituted with a substituent selected from the group consisting of fluoro, —CN and —C(=O)NR$^{10a}$R$^{10b}$; and C$_{2-4}$alkyl substituted with a substituent selected from the group consisting of —OR$^{11}$ and —NR$^{10a}$R$^{10b}$; wherein
R$^{10a}$, R$^{10b}$ and R$^{11}$ are each independently selected from the group consisting of hydrogen and C$_{1-4}$alkyl; and
R$^3$ is selected from the group consisting of Ar; Het$^1$; Het$^2$; and a 7- to 10-membered saturated spirocarbobicyclic system; or
(b) L$^2$ is selected from >CR$^{4c}$R$^{4d}$, and —CHR$^{4c}$CHR$^{5a}$—; wherein R$^{4c}$, R$^{4d}$ and R$^{5a}$ are each independently selected from the group consisting of hydrogen; and C$_{1-4}$alkyl; and
R$^3$ is selected from the group consisting of

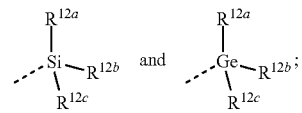

wherein
R$^{12a}$, R$^{12b}$ and R$^{12c}$ are each independently selected from the group consisting of C$_{1-6}$alkyl optionally substituted with a —OH or a —NH$_2$ substituent; or
(c) -L$^2$-R$^3$ is C$_{1-6}$alkyl optionally substituted with one, two or three fluoro substituents; or
(d) -L$^2$-R$^3$ is

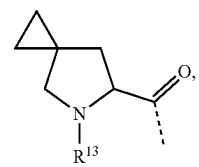

wherein R$^{13}$ is hydrogen; or
(e) -L$^2$-R$^3$ is

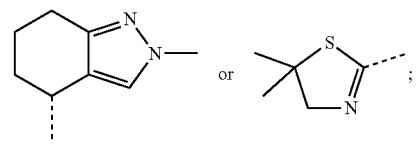

and wherein
Ar is phenyl optionally substituted with one, two, or three substituents each independently selected from the group consisting of halo, —CN, and C$_{1-4}$alkyl optionally substituted with a substituent selected from the group consisting of fluoro, —CN, —OR$^{20}$, —NR$^{21a}$R$^{21b}$, and —(=O)NR$^{21a}$R$^{21b}$;
Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, and C$_{1-4}$alkyl optionally substituted with a substituent selected from the group consisting of fluoro, —CN, —OR$^{20}$, —NR$^{21a}$R$^{21b}$ and —C(=O)NR$^{21a}$R$^{21b}$; and Het$^2$ is a non-aromatic heterocyclyl selected from azetidinyl, pyrrolidinyl and piperidinyl; wherein R$^{20}$, R$^{21a}$, and R$^{21b}$ are each independently selected from the group consisting of hydrogen and C$_{1-4}$alkyl;

and the pharmaceutically acceptable salts and the solvates thereof.

The present invention relates in particular to compounds of Formula (I) as defined herein, and the tautomers and the stereoisomeric forms thereof, wherein R$^1$ is CF$_3$;

(a) L$^2$ is >CR$^{4a}$R$^{4b}$; wherein
R$^{4a}$ is selected from the group consisting of hydrogen; —C(=O)NR$^{7a}$R$^{7b}$; C$_{1-4}$alkyl; and C-linked 4- to 7-membered non-aromatic heterocyclyl containing at least one nitrogen, oxygen or sulfur atom; and
R$^{4b}$ is selected from the group consisting of hydrogen and methyl; wherein
R$^{7a}$ and R$^{7b}$ are each independently selected from the group consisting of hydrogen; C$_{1-4}$alkyl; and C$_{2-4}$alkyl substituted with a substituent selected from the group consisting of —OR$^{11}$ and —NR$^{10a}$R$^{10b}$, wherein
R$^{10a}$, R$^{10b}$ and R$^{11}$ are each independently selected from the group consisting of hydrogen and C$_{1-4}$alkyl; and
R$^3$ is selected from the group consisting of Ar; Het$^1$; and a 7- to 10-membered saturated spirocarbobicyclic system; or (b) L$^2$ is >CR$^{4c}$R$^{4d}$, wherein R$^{4c}$ and R$^{4d}$ are each independently selected from the group consisting of hydrogen; and C$_{1-4}$alkyl; and
R$^3$ is selected from the group consisting of

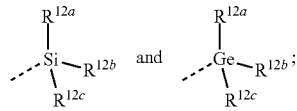

wherein
R$^{12a}$, R$^{12b}$ and R$^{12c}$ are each independently selected from the group consisting of C$_{1-6}$alkyl optionally substituted with a —NH$_2$ substituent; or (c) -L$^2$-R$^3$ is C$_{1-6}$alkyl optionally substituted with one, two or three fluoro substituents; or (d) -L$^2$-R$^3$ is wherein R$^{13}$ is hydrogen; or

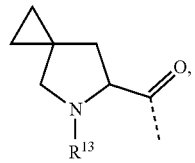

(e) -L$^2$-R$^3$ is

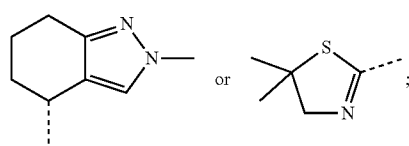

and wherein
Ar is phenyl optionally substituted with a halo substituent; and

Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, and 4- or 5-thiazolyl; each of which may be optionally substituted with one or two substituents each independently selected from the group consisting of halo and C$_{1-4}$alkyl optionally substituted with a substituent selected from the group consisting of —CN, —OR$^{20}$, —NR$^{21a}$R$^{21b}$, and —C(=O)NR$^{21a}$R$^{21b}$; wherein
R$^{20}$, R$^{21a}$, and R$^{21b}$ are each independently selected from the group consisting of hydrogen and C$_{1-4}$alkyl;

and the pharmaceutically acceptable salts and the solvates thereof.

The present invention relates in particular to compounds of Formula (I) as defined herein, and the tautomers and the stereoisomeric forms thereof, wherein R$^1$ is CF$_3$;

L$^1$ is a 7- to 9-membered fused heterocycle of Formula (a) as described herein wherein
m is equal to 0 or 1;
n is equal to 0 or 1;
p is 1 and q is 0;
R is hydrogen; and (a) L$^2$ is >CH$_2$; and R$^3$ is Ar; or Het$^1$; or
(b) L$^2$ is >CH$_2$; and R$^3$ is

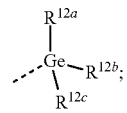

wherein R$^{12a}$, R$^{12b}$, and R$^{12c}$ are each independently selected from C$_{1-6}$alkyl; or (c) -L$^2$-R$^3$ is C$_{1-6}$alkyl optionally substituted with one, two or three fluoro substituents; wherein
Ar is phenyl optionally substituted with a halo substituent; and Het$^1$ is a monocyclic heteroaryl selected from the group consisting of pyridyl, 4-, 5- or 6-pyrimidinyl, pyrazinyl, pyridazinyl, pyrrolyl, pyrazolyl, and 4- or 5-thiazolyl; each of which may be optionally substituted with a halo or a C$_{1-4}$alkyl substituent;

and the pharmaceutically acceptable salts and the solvates thereof.

The present invention relates in particular to compounds of Formula (I) as defined herein, and the tautomers and the stereoisomeric forms thereof, wherein R$^1$ is CF$_3$;
R$^2$ is hydrogen;
L$^1$ is a 8- to 9-membered fused heterocycle of Formula (a-1) or (a-2)

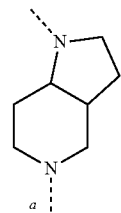

(a-1)

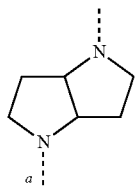
(a-2)

(a) L² is >CH₂; and R³ is Ar; or Het¹; or
(b) L² is >CH₂; and R³ is —Ge(CH₃)₃; wherein
Ar is phenyl optionally substituted with a halo substituent; and
Het¹ is a monocyclic heteroaryl selected from the group consisting of pyridyl, 4-, 5- or 6-pyrimidinyl, pyrrolyl, pyrazolyl, and 4- or 5-thiazolyl; each of which may be optionally substituted with a halo or a $C_{1-4}$alkyl substituent;

and the pharmaceutically acceptable salts and the solvates thereof.

The present invention relates in particular to compounds of Formula (I) as defined herein, and the tautomers and the stereoisomeric forms thereof, wherein
R¹ is CF₃;
R² is hydrogen;
L¹ is a 8- to 9-membered fused heterocycle of Formula (a-1), (a-3)

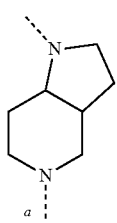
(a-1)

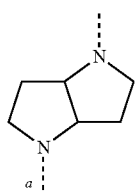
(a-2)

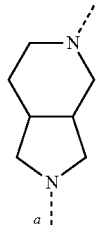
(a-3)

(a) L² is >CH₂; and R³ is Ar; Het¹; or Het²; or
(b) L² is >CH₂; and R³ is —Ge(CH₃)₃; or
(c) -L²-R³ is $C_{1-6}$alkyl;
wherein
Ar is phenyl optionally substituted with a halo substituent; and
Het¹ is a monocyclic heteroaryl selected from the group consisting of pyridyl, 4-, 5- or 6-pyrimidinyl, pyrrolyl, pyrazolyl, and 4- or 5-thiazolyl; each of which may be optionally substituted with a halo, OR¹⁸ or a $C_{1-4}$alkyl substituent;

Het² is a non-aromatic heterocyclyl selected from the group consisting of 4-piperidinyl and 4-tetrahydropyranyl;

R¹⁸ is hydrogen or $C_{1-4}$alkyl;

and the pharmaceutically acceptable salts and the solvates thereof.

In an embodiment, the present invention relates to those compounds of Formula (I) and the pharmaceutically acceptable salts, and the solvates thereof, or any subgroup thereof as mentioned in any of the other embodiments, wherein
L¹ is a 8- to 9-membered fused heterocycle of Formula (a-1) or (a-2)

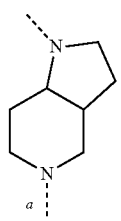
(a-1)

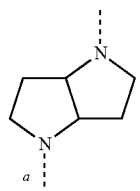
(a-2)

L² >CH₂; and R³ is Ar or Het¹; or
L² is >CH₂ and R³ is

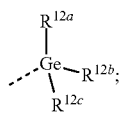

wherein R¹²ᵃ, R¹²ᵇ, and R¹²ᶜ are each independently selected from $C_{1-6}$alkyl.

In an embodiment, the present invention relates to those compounds of Formula (I) and the pharmaceutically acceptable salts, and the solvates thereof, or any subgroup thereof as mentioned in any of the other embodiments, wherein
L¹ is a 8- to 9-membered fused heterocycle of Formula (a-1), (a-2) or (a-3)

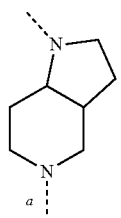
(a-1)

-continued (a-2)
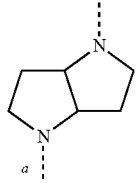

L² >CH₂; and R³ is Ar, Hell or Het²; or
L² is >CH₂ and R³ is

wherein $R^{12a}$, $R^{12b}$, and $R^{12c}$ are each independently selected from $C_{1-6}$ alkyl; or
-L²-R³ is $C_{1-6}$alkyl.

In an embodiment, the present invention relates to those compounds of Formula (I) and the pharmaceutically acceptable salts, and the solvates thereof, or any subgroup thereof as mentioned in any of the other embodiments, wherein
L¹ is a 8- to 9-membered fused heterocycle of Formula (a-3)

(a-3)
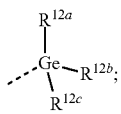

In an embodiment, the present invention relates to those compounds of Formula (I) and the pharmaceutically acceptable salts, and the solvates thereof, or any subgroup thereof as mentioned in any of the other embodiments, wherein L¹ is a 8- to 9-membered fused heterocycle of Formula (a-1), (a-2), (a-3), (a-4), (a-5), (a-6), (a-7), (a-8), (a-9), (a-10) or (a-11)

(a-1)
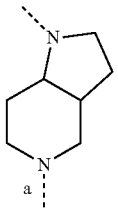

(a-2)
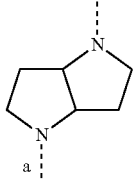

(a-3)
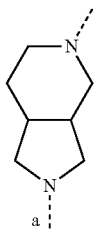

(a-4)

(a-5)
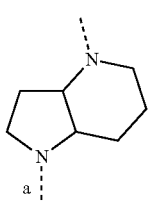

(a-6)
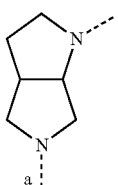

(a-7)
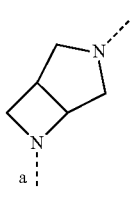

-continued (a-8) 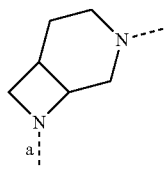

(a-9) 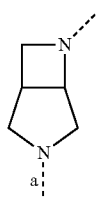

(a-10) 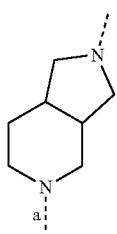

(a-11) 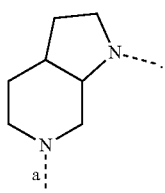

Another embodiment of the present invention relates to those compounds of Formula (I) and the pharmaceutically acceptable salts, and the solvates thereof, or any subgroup thereof as mentioned in any of the other embodiments wherein one or more of the following restrictions apply:

(a) $R^1$ is $CF_3$;
(b) $R^2$ is hydrogen;
(c) m is 0 or 1; n is 1; p is 1 and q is 0;
(d) $L^1$ is (a-1);
(e) $L^1$ is (a-2);
(f) $L^2$ is >$CH_2$;
(g) $R^3$ is Ar or $Het^1$;
(h) -$L^2$-$R^3$ is selected from the group consisting of

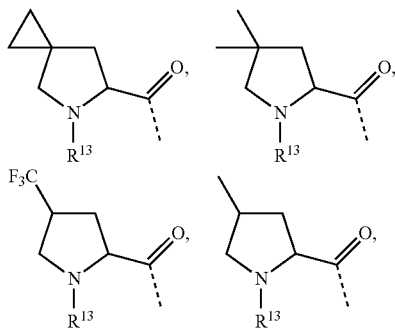

-continued

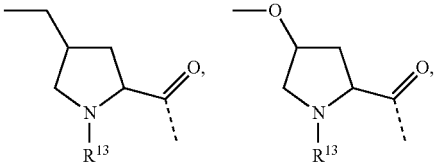

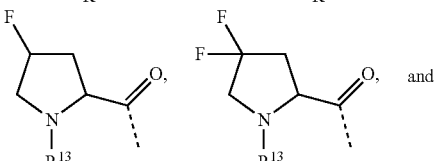

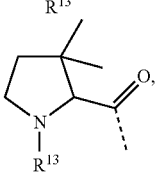

wherein
$R^{13}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{14}$ and —$NR^{15a}R^{15b}$; wherein
$R^{14}$, $R^{15a}$ and $R^{15b}$ are each independently selected from the group consisting of hydrogen; $C_{1-4}$alkyl optionally substituted with a substituent selected from the group consisting of fluoro, —CN, and —C(=O)$NR^{16a}R^{16b}$; $C_{2-4}$alkyl substituted with a substituent selected from the group consisting of —$OR^{17}$ and —$NR^{16a}R^{16b}$; and C-linked 4- to 7-membered non-aromatic heterocyclyl containing at least one nitrogen, oxygen or sulfur atom; wherein
$R^{16a}$, $R^{16b}$ and $R^{17}$ are each independently selected from the group consisting of hydrogen and $C_{1-4}$alkyl;
(i) -$L^2R^3$ is —$CH_2R^3$ wherein $R^3$ is selected from the group consisting of

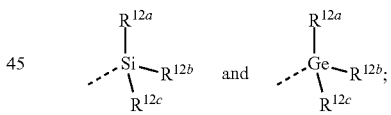

wherein $R^{12a}$, $R^{12b}$ and $R^{12c}$ are each independently selected from the group consisting of $C_{1-6}$alkyl optionally substituted with —$NH_2$;
(j) Ar is phenyl optionally substituted with one or two substituents each independently selected from the group consisting of halo and $C_{1-4}$ alkyl optionally substituted with a substituent selected from the group consisting of —CN, —$OR^{20}$, —$NR^{21a}R^{21b}$, and —C(=O)$NR^{21a}R^{21b}$, wherein $R^{20}$, $R^{21a}$, and $R^{21b}$ are each independently selected from the group consisting of hydrogen and $C_{1-4}$alkyl;
(k) Ar is phenyl optionally substituted with one or two halo substituents;
(l) Ar is phenyl optionally substituted with a halo substituent;
(m) $Het^1$ is a monocyclic heteroaryl selected from the group consisting of pyrazolyl, imidazolyl, pyrrolyl, 4- or 5-thiazolyl, pyridyl, pyridazinyl, 4-, 5- or 6-pyrimidinyl, and pyrazinyl, each of which may be optionally substituted with one or two substituents each independently selected from the group consisting of halo and $C_{1-4}$alkyl optionally substituted with a substituent selected from the group consisting of —CN, —OR$^{20}$, —NR$^{21a}$R$^{21b}$, and —C(=O)NR$^{21a}$R$^{21b}$;
wherein R$^{20}$, R$^{21a}$, and R$^{21b}$ are each independently selected from the group consisting of hydrogen and $C_{1-4}$alkyl;

(n) Het$^1$ is a monocyclic heteroaryl selected from the group consisting of pyrazolyl, imidazolyl, pyrrolyl, 4- or 5-thiazolyl, pyridyl, pyridazinyl, 4-, 5- or 6-pyrimidinyl, and pyrazinyl, each of which may be optionally substituted with one or two substituents each independently selected from the group consisting of halo and $C_{1-4}$alkyl;

(o) Het$^1$ is a monocyclic heteroaryl selected from the group consisting of pyrazolyl, pyrrolyl, 4- or 5-thiazolyl, pyridyl, and 4-, 5- or 6-pyrimidinyl, each of which may be optionally substituted with one or two substituents each independently selected from the group consisting of halo and $C_{1-4}$alkyl;

(p) Het$^1$ is a monocyclic heteroaryl selected from the group consisting of pyrazolyl, pyrrolyl, 4- or 5-thiazolyl, pyridyl, and 4-, 5- or 6-pyrimidinyl, each of which may be optionally substituted with a halo or a $C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein at least one of m, n, q and p is different from 0.

In an embodiment, the present invention relates to those compounds of Formula (I) and the pharmaceutically acceptable salts, and the solvates thereof, or any subgroup thereof as mentioned in any of the other embodiments, wherein
m is equal to 1;
n is equal to 0;
p is equal to 1;
q is equal to 1.

In an embodiment, the present invention relates to those compounds of Formula (I) and the pharmaceutically acceptable salts, and the solvates thereof, or any subgroup thereof as mentioned in any of the other embodiments, wherein m is 1.

In an embodiment, the present invention relates to those compounds of Formula (I) and the pharmaceutically acceptable salts, and the solvates thereof, or any subgroup thereof as mentioned in any of the other embodiments, wherein n is 1.

In an embodiment, the present invention relates to those compounds of Formula (I) and the pharmaceutically acceptable salts, and the solvates thereof, or any subgroup thereof as mentioned in any of the other embodiments, wherein p is 1 or 2.

In an embodiment, the present invention relates to those compounds of Formula (I) and the pharmaceutically acceptable salts, and the solvates thereof, or any subgroup thereof as mentioned in any of the other embodiments, wherein q is 1.

In an embodiment, the present invention relates to those compounds of Formula (I) and the pharmaceutically acceptable salts, and the solvates thereof, or any subgroup thereof as mentioned in any of the other embodiments, wherein R$^1$ is CF$_3$ In an embodiment, the present invention relates to those compounds of Formula (I) and the pharmaceutically acceptable salts, and the solvates thereof, or any subgroup thereof as mentioned in any of the other embodiments, wherein IV is CF$_3$, and wherein R$^2$ is hydrogen.

In an embodiment, the present invention relates to those compounds of Formula (I) and the pharmaceutically acceptable salts, and the solvates thereof, or any subgroup thereof as mentioned in any of the other embodiments, wherein R$^1$ is CF$_3$; R$^2$ is hydrogen;
m is equal to 1;
n is equal to 0;
p is equal to 1;
q is equal to 1.

In an embodiment, the present invention relates to those compounds of Formula (I) and the pharmaceutically acceptable salts, and the solvates thereof, or any subgroup thereof as mentioned in any of the other embodiments, wherein Ar is phenyl optionally substituted according to any of the other embodiments.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (b). In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (c).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (d).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (e).

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$ or Het$^2$.

In an embodiment, the present invention relates to those compounds of Formula (I) and the pharmaceutically acceptable salts, and the solvates thereof, or any subgroup thereof as mentioned in any of the other embodiments, wherein -L$^2$-R$^3$ is (a); R$^3$ is Het$^1$.

In an embodiment, the present invention relates to those compounds of Formula (I) and the pharmaceutically acceptable salts, and the solvates thereof, or any subgroup thereof as mentioned in any of the other embodiments, wherein
Ar is phenyl which may be optionally substituted with one, two, or three substituents each independently selected from the group consisting of halo, —CN, —OR$^{18}$, —NR$^{19a}$R$^{19b}$, and $C_{1-4}$alkyl optionally substituted with a substituent selected from the group consisting of fluoro, —CN, —OR$^{20}$, —NR$^{21a}$R$^{21b}$ and —(=O)NR$^{21a}$R$^{21b}$;
Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^{18}$, —NR$^{19a}$R$^{19b}$, $C_{3-6}$cycloalkyl, and $C_{1-4}$alkyl optionally substituted with a substituent selected from the group consisting of fluoro, —CN, —OR$^{20}$, —NR$^{21a}$R$^{21b}$, and —C(=O)NR$^{21a}$R$^{21b}$, and Het$^2$ is a non-aromatic heterocyclyl optionally substituted with one, two, or three substituents each independently selected from the group consisting of halo, —CN, —OR$^{18}$, —NR$^{19a}$R$^{19b}$, —C(=O)C$_{1-6}$alkyl, —C(=O)—O—C$_{1-6}$alkyl, —C(=O)—C$_{3-6}$cycloalkyl, —C(=O)—Ar$^2$, —C(=O)—Het$^3$, —C(=O)—Het$^4$, and C$_{1-4}$alkyl optionally substituted with a substituent selected from the group consisting of fluoro, —CN, —OR$^2$—NR$^{21a}$R$^{21b}$, and —C(=O)NR$^{21a}$R$^{21b}$.

In an embodiment, the present invention relates to those compounds of Formula (I) and the pharmaceutically acceptable salts, and the solvates thereof, or any subgroup thereof as mentioned in any of the other embodiments, wherein
R$^1$ is CF$_3$;
R$^2$ is hydrogen;
m is equal to 1; n is equal to 0; p is equal to 1; q is equal to 1;
R is hydrogen.

In an embodiment, the present invention relates to those compounds of Formula (I) and the pharmaceutically acceptable salts, and the solvates thereof, or any subgroup thereof as mentioned in any of the other embodiments, wherein
R$^1$ is CF$_3$;
R$^2$ is hydrogen;
m is equal to 1; n is equal to 0; p is equal to 1; q is equal to 1;
R is hydrogen;
L$^2$ is >CR$^{4a}$R$^{4b}$; R$^3$ is Het$^1$ or Het$^2$; or -L$^2$-R$^3$ is C$_{1-6}$alkyl.

In an embodiment, the present invention relates to those compounds of Formula (I) and the pharmaceutically acceptable salts, and the solvates thereof, or any subgroup thereof as mentioned in any of the other embodiments, wherein
R$^1$ is CF$_3$;
R$^2$ is hydrogen;
m is equal to 1; n is equal to 0; p is equal to 1; q is equal to 1;
R is hydrogen;
L$^2$ is >CR$^{4a}$R$^{4b}$; R$^3$ is Het$^1$ or Het$^2$; or -L$^2$-R$^3$ is C$_{1-6}$alkyl;
R$^{4a}$ and R$^{4b}$ are hydrogen.

In an embodiment, the present invention relates to those compounds of Formula (I) and the pharmaceutically acceptable salts, and the solvates thereof, or any subgroup thereof as mentioned in any of the other embodiments, wherein Het$^2$ is piperidinyl or tetrahydropyranyl, each of which are optionally substituted with one, two, or three substituents as described in the other embodiments.

In an embodiment, the present invention relates to those compounds of Formula (I) and the pharmaceutically acceptable salts, and the solvates thereof, or any subgroup thereof as mentioned in any of the other embodiments, wherein Het$^2$ is monocyclic heterocyclyl optionally substituted with one, two, or three substituents as described in the other embodiments.

In an embodiment, the present invention relates to those compounds of Formula (I) and the pharmaceutically acceptable salts, and the solvates thereof, or any subgroup thereof as mentioned in any of the other embodiments, wherein Het$^2$ is a non-aromatic heterocyclyl selected from

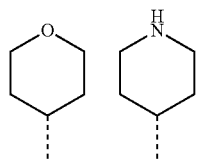

each of which are optionally substituted with one, two, or three substituents as described in the other embodiments.

Particular compounds of Formula (I) are:

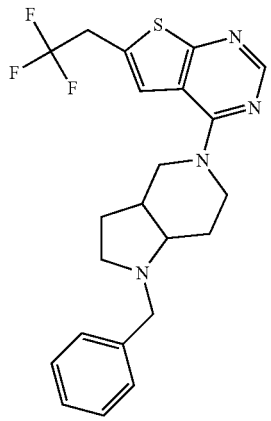

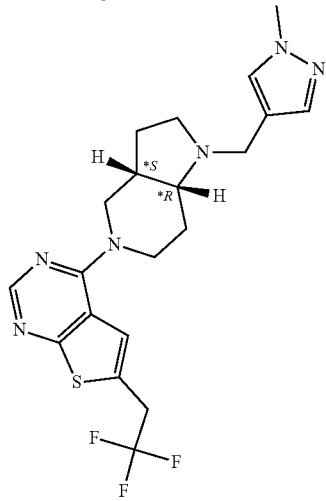

including the stereoisomeric forms, the pharmaceutically acceptable salts thereof, in particular the hydrochloride salts thereof, and the solvates thereof.

Particular compounds of Formula (I) are compounds 70, 71B, 36, 87 and 102, including the stereoisomeric forms, the pharmaceutically acceptable salts thereof, in particular the hydrochloride salts thereof, and the solvates thereof.

Particular compounds of Formula (I) are compounds 70, 71B, 36, 87 and 102.

In an embodiment the compound of Formula (I) is selected from the group consisting of any of the exemplified compounds,
and the free bases, the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 1, the NH moiety on the $L^1$ 7- to 9-fused heterocycle can be protected with a tert-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt.

In general, compounds of Formula (I) wherein all variables are defined according to the scope of the present invention, can be prepared according to the following reaction Scheme 1. In Scheme 1, $LG^1$ and $LG^2$ each represent a suitable leaving group, such as for example halo; $PG^1$ represents a suitable protecting group, such as for example tert-butyloxycarbonyl; $R^{3a}$-$PG^2$ represents an $R^3$ as defined in Formula (I) with an appropriate protecting group, such as for example tert-butyloxycarbonyl, when the $R^3$ substituent bears an amino group. All other variables in Scheme 1 are defined according to the scope of the present invention.

In Scheme 1, the following reaction conditions apply:

SCHEME 1

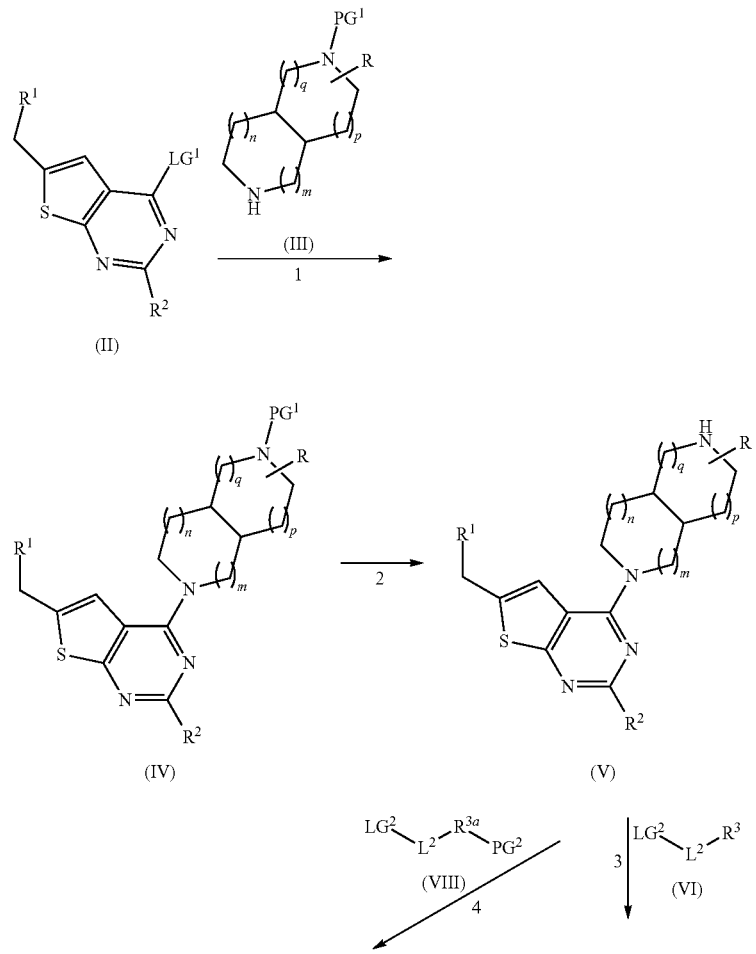

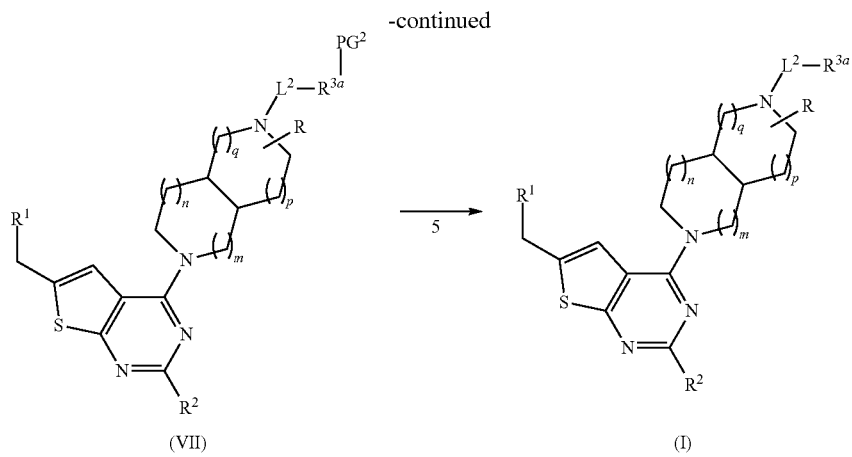

(VII) → (I)

1: at a suitable temperature such as for example at 90° C., in the presence of a suitable base such as for example diisopropylethylamine, in a suitable solvent such as for example acetonitrile or isopropanol;

2: at a suitable temperature range such as for example from 0° C. to room temperature, in the presence of suitable cleavage conditions, such as for example an acid such as HCl or trifluoroacetic acid in a suitable solvent such as acetonitrile or dichloromethane or methanol when $PG^1$ is tert-butyloxycarbonyl;

3: at a suitable temperature such as for example room temperature, in the presence of a suitable base such as for example potassium carbonate or Diazabicyclo[5.4.0]undec-7-ene, in a suitable solvent such as for example acetonitrile, dimethylformamide or dimethylsulfoxide;

4: at a suitable temperature such as for example room temperature, in the presence of a suitable base such as for example potassium carbonate or Diazabicyclo[5.4.0]undec-7-ene, in a suitable solvent such as for example acetonitrile, dimethylformamide or dimethylsulfoxide;

5: at a suitable reaction temperature range such as for example from 0° C. to room temperature, in the presence of suitable cleavage conditions, such as for example an acid such as HCl or trifluoroacetic acid in a suitable solvent such as acetonitrile, dioxane or methanol when $PG^2$ is tert-butyloxycarbonyl.

Intermediates of Formula (II), wherein $R^2$ is methyl, can be prepared according to the following reaction Scheme 2, wherein $LG^1$ represents a suitable leaving group, such as for example halo or methanesulfonyl. All other variables in Scheme 2 are defined according to the scope of the present invention.

In Scheme 2, the following reaction conditions apply:

SCHEME 2

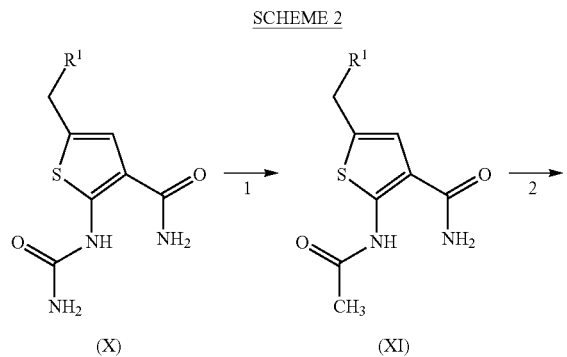

(X) → (XI) → (XII) → (XIII)

1: at a suitable temperature such as for example at reflux temperature, in the presence of acetic anhydride and a suitable base such as for example trimethylamine, in a suitable solvent such as for example toluene;

2: at a suitable temperature such as for example at reflux temperature, in the presence of a suitable base such as potassium hydroxide, in a suitable solvent such as for example ethanol;

3: under suitable reaction conditions to form a leaving group, such as for example, chloro, for example by reaction with phosphoryl trichloride at a suitable temperature such as 110° C.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

THF or dicholoromethane or a mixture of dichloromethane and methanol, yielding a compound of Formula (Ia).

Alternatively, step 1 can be performed in the presence of a suitable catalyst such as platinum oxide, in a suitable solvent such as for example ethanol at a suitable temperature such as for example 60° C.;

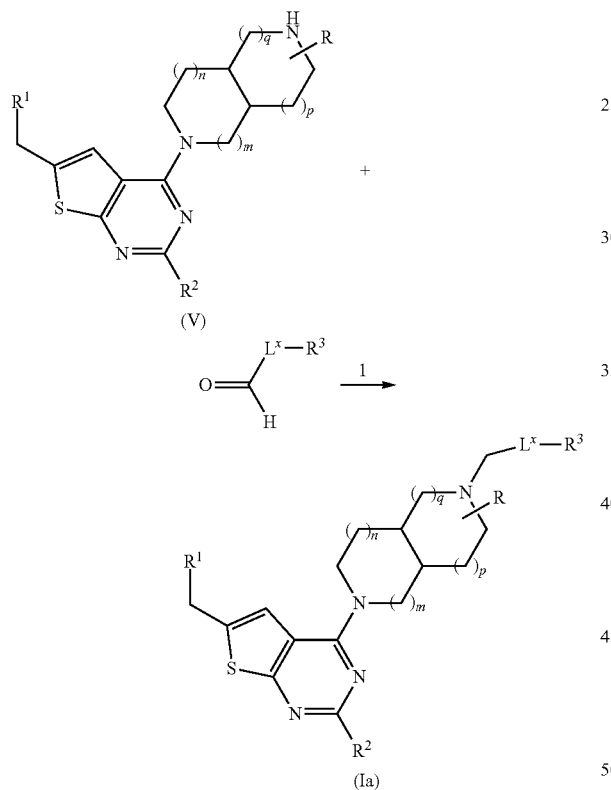

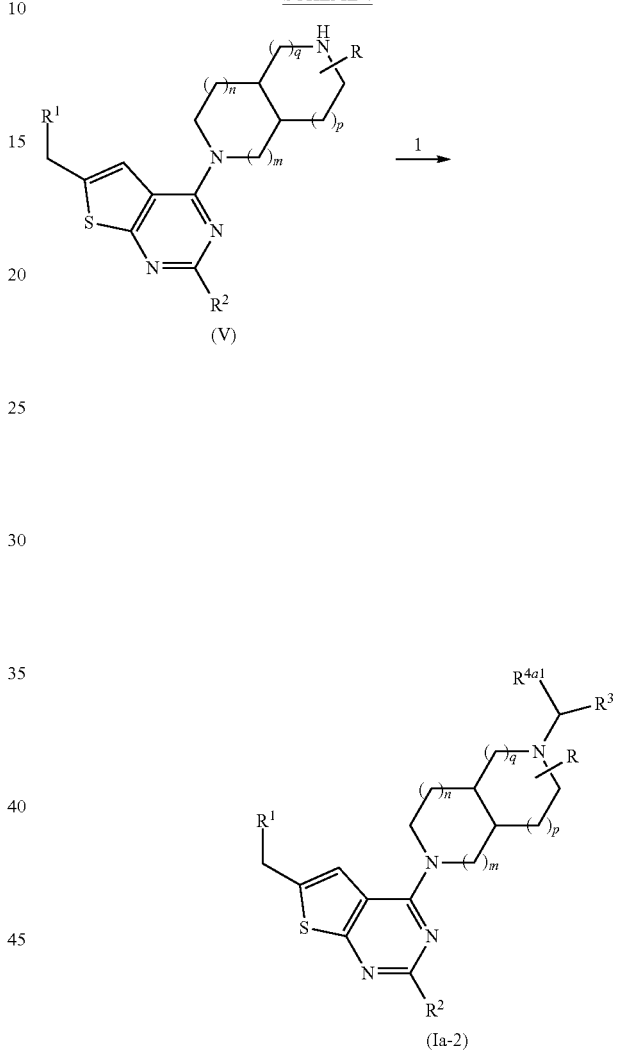

In general, compounds of Formula (I) wherein all variables are defined according to the scope of the present invention, can be prepared according to the following reaction Scheme 3. In Scheme 3, $L^x$ is $L^2$ which is attached to $L^1$ via a $CH_2$ group (which is also part of $L^2$). All other variables in Scheme 3 are defined according to the scope of the present invention. In Scheme 3, the following reaction conditions apply:

1: At a suitable temperature, for example room temperature, optionally in the presence of a suitable acid such as for example acetic acid, in a suitable solvent such as THF or dicholoromethane or a mixture of dichloromethane and methanol followed by addition of a suitable reducing agent, such as for example $NaBH(OAc)_3$, at a suitable temperature, for example room temperature, in a suitable solvent such as In general, compounds of Formula (Ia-2) wherein all variables are defined according to the scope of the present invention, can be prepared according to the following reaction Scheme 4. In Scheme 4, $R^{4a1}$ is defined as $C_{1-4}$alkyl or a C-linked 4- to 7-membered non-aromatic heterocyclyl containing at least one nitrogen, oxygen or sulfur atom). All other variables in Scheme 4 are defined according to the scope of the present invention. In Scheme 4, the following reaction conditions apply:

1: At a suitable temperature, for example room temperature, in the presence of Titanium (IV) ethoxide, in a suitable solvent such as THF, followed by addition with suitable organolithium ($R^{4a1}$—Li) or Grignard ($R^{4a1}$—Mg-halo) reagents that are either commercially available or can be prepared by methods known to the skilled person, yielding a compound of Formula (Ia-2).

SCHEME 5

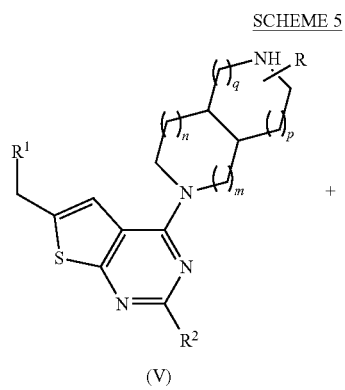

(V)

+

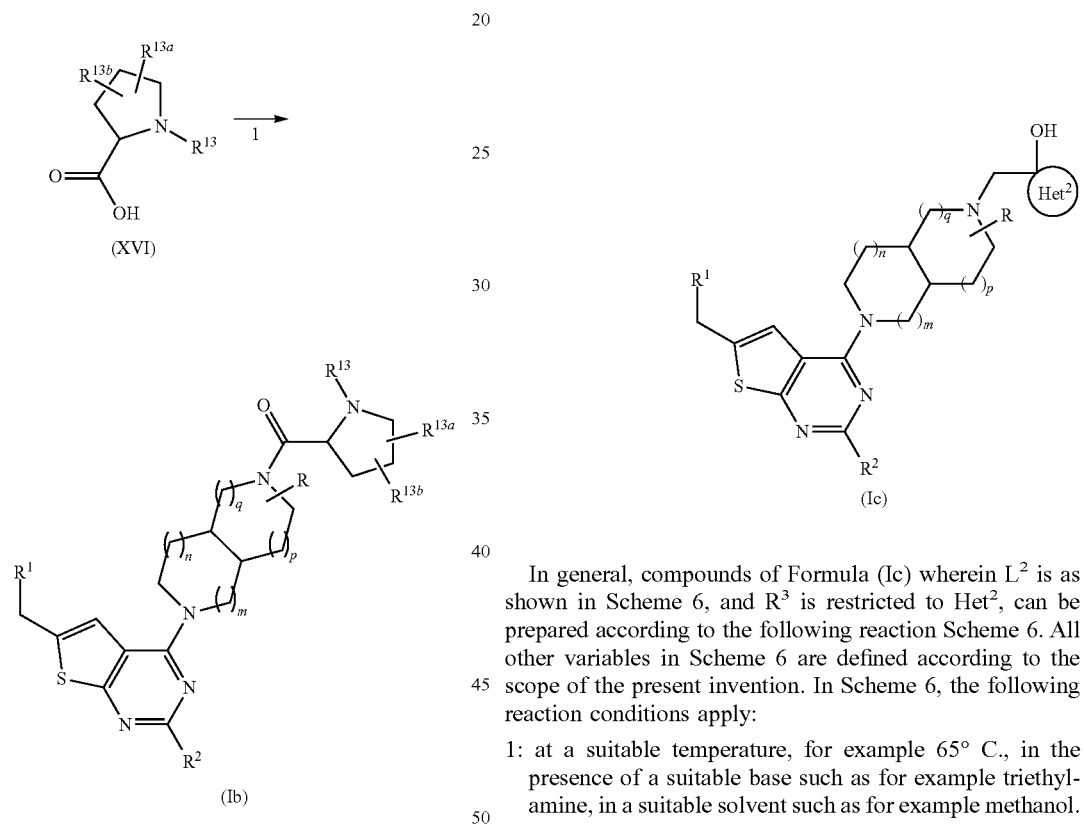

(XVI)

(Ib)

In general, compounds of Formula (I) wherein all variables are defined according to the scope of the present invention, hereby named compounds of Formula (Ib), can be prepared according to the following reaction Scheme 5. All variables in Scheme 5 are defined according to the scope of the present invention. In Scheme 5, the following reaction conditions apply:

1: at a suitable temperature, for example room temperature, in the presence of a suitable acid coupling agent, such as for example 1-[bis(dimethylamino)methylene]-1H-benzotriazoliumhexafluorophosphate(1-)₃-oxide (HBTU), in a suitable solvent such as N,N-dimethylformamide (DMF); with a suitable base such as N-ethyl-N-(1-methylethyl)-2-propanamine (DIPEA) yielding a compound of Formula (Ib).

SCHEME 6

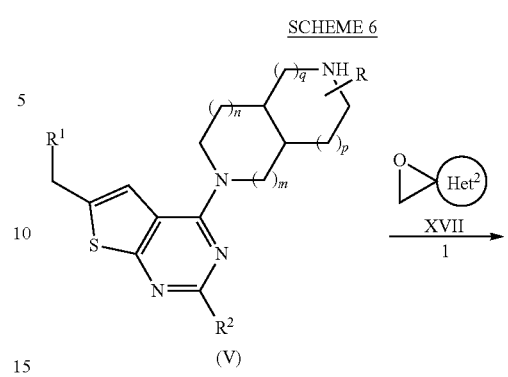

(V)

(Ic)

In general, compounds of Formula (Ic) wherein $L^2$ is as shown in Scheme 6, and $R^3$ is restricted to $Het^2$, can be prepared according to the following reaction Scheme 6. All other variables in Scheme 6 are defined according to the scope of the present invention. In Scheme 6, the following reaction conditions apply:

1: at a suitable temperature, for example 65° C., in the presence of a suitable base such as for example triethylamine, in a suitable solvent such as for example methanol.

SCHEME 7

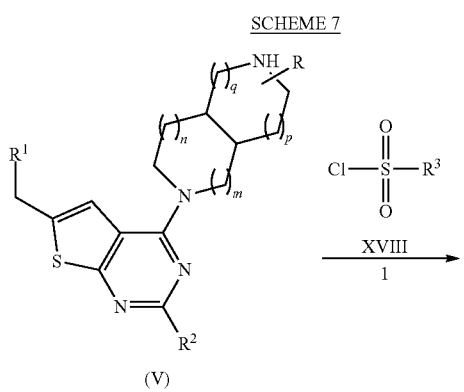

(V)

-continued

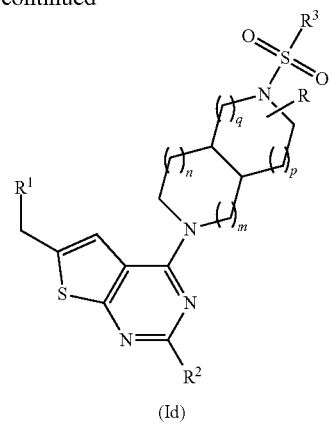

(Id)

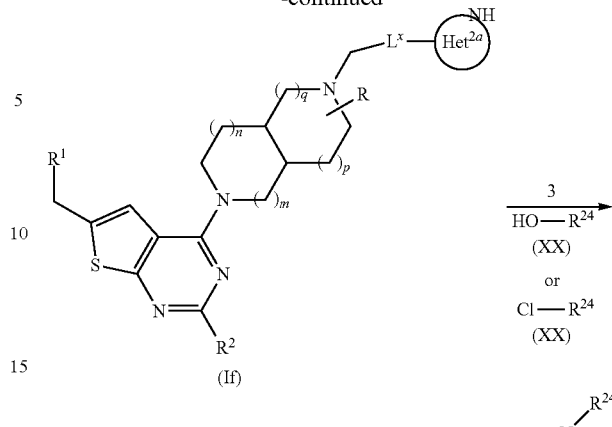

(If)

In general, compounds of Formula (Id) wherein $L^2$ is as shown in Scheme 7, and wherein all variables are defined according to the scope of the present invention, can be prepared according to the following reaction Scheme 7.

In Scheme 7, the following reaction conditions apply:

1: at a suitable temperature, for example room temperature, in the presence of a suitable base such as for example potassium carbonate, in a suitable solvent such as for example acetonitrile.

SCHEME 8

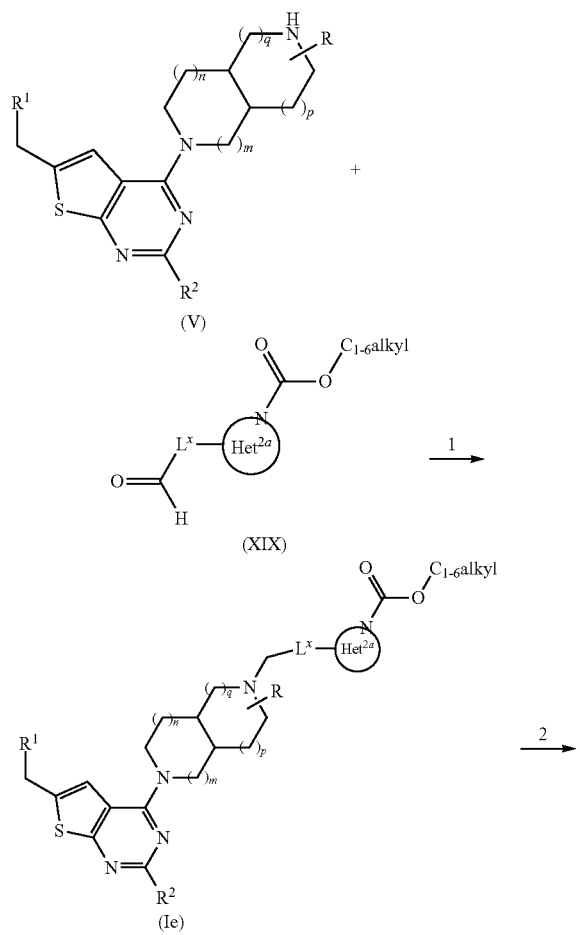

(Ig)

In general, compounds of Formula (Ie), (If) and (Ig) wherein $R^3$ is restricted to $Het^2a$ being an optionally substituted non-aromatic heterocyclyl containing a nitrogen atom, can be prepared according to the following reaction Scheme 8. In scheme 8, $R^{24}$ is defined as being —C(=O)—$C_{1-6}$alkyl, —C(=O)—O—$C_{1-6}$alkyl, —C(=O)—$C_{3-6}$cycloalkyl, —C(=O)—$Ar^2$, —C(=O)—$Het^3$, —C(=O)—$Het^4$. $L^x$ is a bond or —$CHR^{5a}$ wherein $R^{5a}$ is H or $C_{1-4}$alkyl. All other variables in Scheme 8 are defined according to the scope of the present invention.

In Scheme 8, the following reaction conditions apply:

Pharmacology

It has been found that the compounds of the present invention block the interaction of menin with MLL proteins and oncogenic MLL fusion proteins. Therefore the compounds according to the present invention and the pharmaceutical compositions comprising such compounds may be useful for the treatment or prevention, in particular treatment, of diseases such as cancer, myelodysplastic syndrome (MDS) and diabetes.

In particular, the compounds according to the present invention and the pharmaceutical compositions thereof may be useful in the treatment or prevention of cancer. According to one embodiment, cancers that may benefit from a treatment with menin/MLL inhibitors of the invention comprise leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

Also, the present invention relates to the use of a compound of Formula (I), a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with the interaction of menin with MLL proteins and oncogenic MLL fusion proteins in a mammal, including a human, the treatment or prevention of which is affected or facilitated by blocking the interaction of menin with MLL proteins and oncogenic MLL fusion proteins.

The invention also relates to a compound of Formula (I), a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), the tautomers and the stereoisomeric forms thereof, and the pharmaceutically acceptable salts, and the solvates thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable salt, or a solvate thereof, to warm-blooded animals, including humans.

Therefore, the invention also relates to a method for the treatment or prevention of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 100 mg/kg, in particular 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral; percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility; may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour, being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The following examples further illustrate the present invention.

EXAMPLES

Several methods for preparing the compounds of this invention are illustrated in the following examples. Unless otherwise noted, all starting materials were obtained from commercial suppliers and used without further purification.

Hereinafter, the terms: 'AcN' or 'ACN' means acetonitrile, 'DCM' means dichloromethane, 'DIEA' or 'DIPEA' means N,N-diisopropylethylamine, 'h' means hours(s), 'min' means minute(s), 'DMF' means dimethylformamide, 'DSC' means differential scanning calorimetry, 'Et₃N' or 'TEA' means triethylamine, 'EtOAc' or 'EA' means ethyl acetate, 'Et₂O' means diethyl ether, 'EtOH' means ethanol, 'FA' means formic acid, 'HOBt' or 'HOBT' means 1-hydroxy-1H-benzotriazole, means High-performance Liquid Chromatography, 'prep-HPLC' means preparative HPLC, 'prep-TLC' means preparative thin layer chromatography, 'IPA' or 'iPrOH' or 'iPrOH' means isopropyl alcohol, 'IBX' means 2-iodoxybenzoic acid, IC/MS' or 'IC-MS' means Liquid Chromatography/Mass Spectrometry, 'MeOH' means methanol, 'NMR' means Nuclear Magnetic Resonance, 'rt' means room temperature, 'SFC' means supercritical fluid chromatography, 'M.P.' or 'm.p.' means melting point, 'OR' means optical rotation, 'iPrNH₂' means isopropylamine, 'THF' means tetrahydrofuran, 'EDCI' means N'-(ethylcarbonimidoyl)-N,N-dimethyl-1,3-propanediamine monohydrochloride, 'BOC' or 'boc' means tert-butyloxycarbonyl, 'DEA' means diethylamine, 'DCE' means dichloroethane, 'NaBH(OAc)₃' means sodium triacetoxyborohydride, 'Int.' means intermediate, 'DBU' means 1,8-diazabicyclo[5.4.0]undecane-7, 'HBTU' means 1-[bis(dimethylamino)methylene]-1H-benzotriazoliumhexafluorophosphate(1-)3-oxide, 'TBAF' means tetrabutylammonium fluoride, 'TFA' means trifluoroacetic acid, 'PE' means petroleum ether, 'min' means minute(s), 'Pd(dppf)Cl₂' means [1,1'-bis-(diphenylphosphino-κP)ferrocene]dichloropalladium, 'PE' means petroleum ether, 'LAH' means lithium aluminium hydride, 'v/v' means volume per volume.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

When a stereocentre is indicated with 'RS' this means that a racemic mixture was obtained at the indicated centre, unless otherwise indicated.

The stereochemical configuration for centres in some compounds may be designated "R" or "S" when the mixture(s) was separated; for some compounds, the stereochemical configuration at indicated centres has been designated as "*R" (first eluted from the column in case the column conditions are described in the synthesis protocol and when only one stereocentre present) or "*S" (second eluted from the column in case the column conditions are described in the synthesis protocol and when only one stereocentre present) when the absolute stereochemistry is undetermined (even if the bonds are drawn stereospecifically) although the compound itself has been isolated as a single stereoisomer and is enantiomerically pure.

The term "enantiomerically pure" as used herein means that the product contains at least 80% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

Similar, the stereochemical configuration at indicated centres has also been designated "*R" or "*S" when a single stereocentre is present in combination with 2 adjacent chiral bridging atoms in the fused hetereocycle L¹, and when the absolute stereochemistry of the single stereocentre is undetermined (even if the bonds are drawn stereospecifically) but enantiomerically pure.

For Example Compound 79A/79B

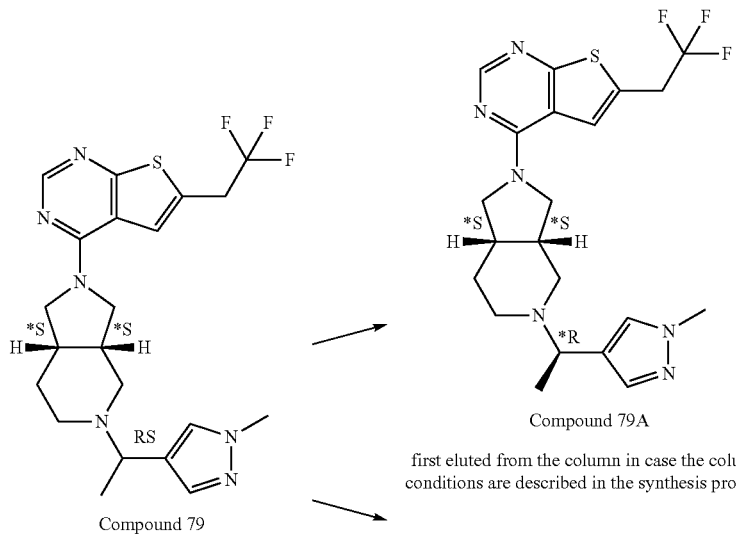

Compound 79

Compound 79A first eluted from the column in case the column conditions are described in the synthesis protocol -continued

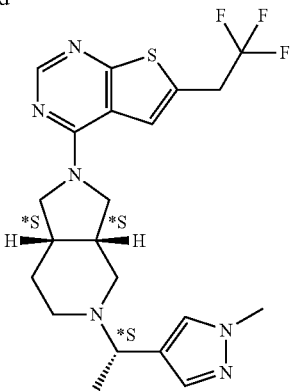

Compound 79B second eluted from the column in case the column conditions are described in the synthesis protocol In case the stereochemistry of the 2 adjacent chiral bridging atoms in the fused hetereocycle L¹ is only known relatively to each other, and not absolutely for each centre, the stereochemical configuration of the two stereocentres are indicated by * (e.g. *R or *S). Even if the bonds are drawn stereospecifically, the *R and *S indicate that the configuration of the first stereocentre is only known relatively to the other stereocentre in the fused heterocycle L¹, although the compound itself has been isolated as a single stereoisomer.

For example, for Compound 85

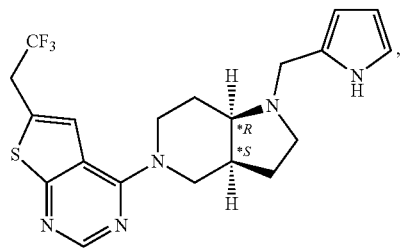 [SMILES: FC(F)(F)Cc1cc2c(N3CC[C@@H]4[C@@H](CCN4Cc4ccc[nH]4)C3)ncnc2s1]

this means that the compound is

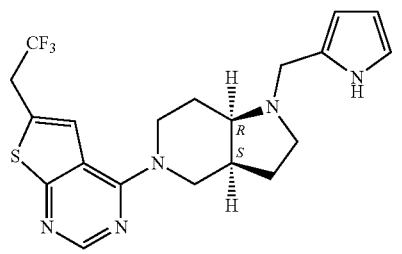

or

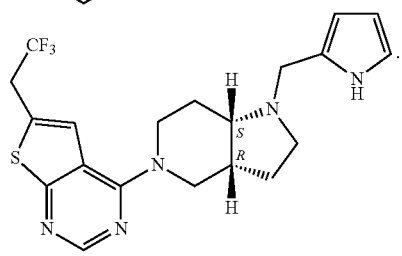

For example, for Compound 79A,

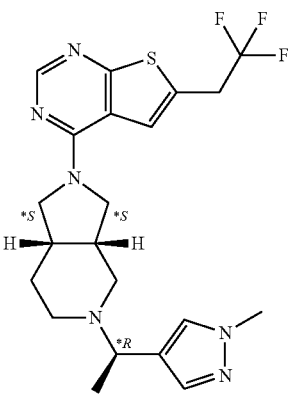 [SMILES: C[C@H](c1cnn(C)c1)N1CC[C@@H]2CN(c3ncnc4sc(CC(F)(F)F)cc34)C[C@@H]2C1]

this means that the compound is

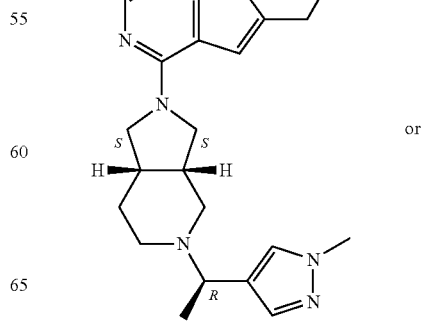

or

-continued

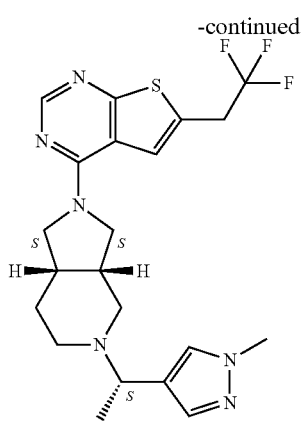

or

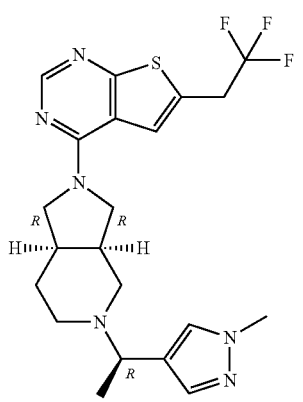

or

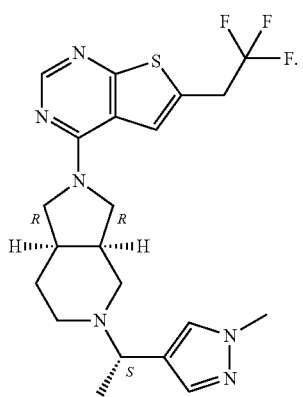

The paragraphs above about stereochemical configurations, also apply to intermediates.

When an intermediate or compound in the experimental part below is indicated as 'HCl salt' or 'TFA salt' without indication of the number of equivalents of HCl or TFA, this means that the number of equivalents of HCl or TFA was not determined.

A skilled person will realize that, even where not mentioned explicitly in the experimental protocols below, typically after a column chromatography purification, the desired fractions were collected and the solvent was evaporated.

A. Preparation of the Intermediates

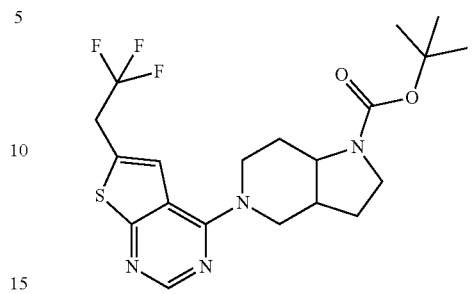

Preparation of Intermediate 1:

Under sealed tube, tert-butyl octahydro-1H-pyrrolo[3,2-c]pyridine-1-carboxylate (3 g, 13.3 mmol), cis relative mixture (CAS[848410-13-9]) prepared as described in Bioorganic & Medicinal Chemistry Letters, 2005, 15(4), 977-982; 4-chloro-6-(2,2,2-trifluoroethyl)thieno[2,3-d]pyrimidine (CAS[1628317-85-0]) (3.5 g, 13.9 mmol) prepared as described in Journal of Medicinal Chemistry (2016), 59(3), 892-913; DIEA (6.9 mL, 39.8 mmol) in iPrOH (60 mL) were heated at 90° C. overnight. The mixture was cooled to rt, poured into ice water then EtOAc was added and extracted with EtOAc (×2). The organic layer was separated, washed with water, dried over $MgSO_4$, filtered and evaporated till dryness to give 9 g of residue. The residue was purified by chromatography over silica gel (Stationary phase: irregular SiOH 40 μm 120 g, mobile phase: 70% heptane, 30% EtOAc). The fractions containing product were collected and evaporated to dryness yielding 5 g (yield 85%) of tert-butyl 5-(6-(2,2,2-trifluoroethyl)-thieno[2,3-d]pyrimidin-4-yl)octahydro-1H-pyrrolo[3,2-c]pyridine-1-carboxylate (I-1) as a cis-relative mixture.

The intermediate in the Table below was prepared using an analogous method as described for the preparation of I-1, starting from the indicated starting material

| INTERMEDIATE NUMBER | Structure |
|---|---|
| Intermediate 2 (from CAS[1628317-85-0] and CAS[885277-81-6], commercially available) | 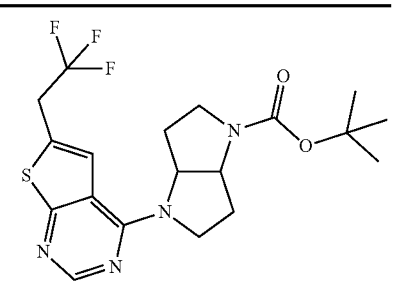 |

| INTERMEDIATE NUMBER | Structure |
|---|---|
| Intermediate 20 (from CAS[185693-02-1]) | 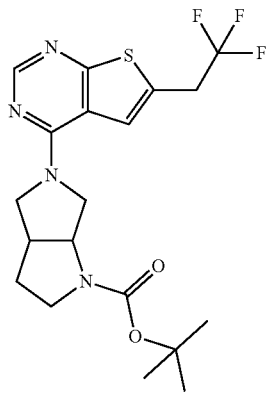 [SMILES: CC(C)(C)OC(=O)N1CCC2CN(c3ncnc4sc(CC(F)(F)F)cc34)CC21] |
| Intermediate 21A and Intermediate 21B (from cis-3-boc-3,7-diazabicyclo[4.2.0]octane CAS[1250993-51-1]) relative congiguration | 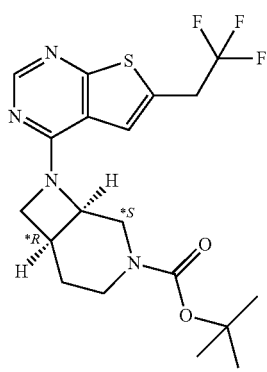
I-21A
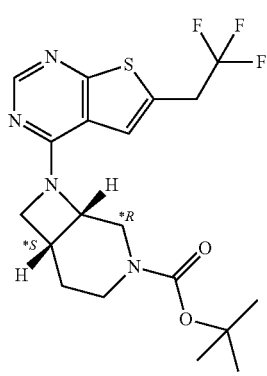
I-21B |
| INTERMEDIATE NUMBER | Structure |
|---|---|
| Intermediate 23 (from (1R,5S)-6-boc-3,6-diazabicyclo[3.2.0]heptane CAS [799279-81-5]) | 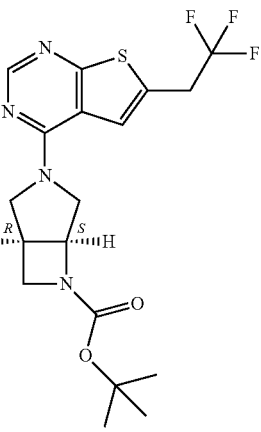 |
| Intermediate 24 (from (1S,5R)-6-boc-3,6-diazabicyclo[3.2.0]heptane CAS [799279-81-51) | 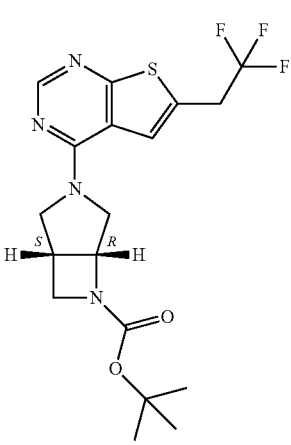 |
| Intermediate 25 (from 5-Boc-octahydro-pyrrolo[3,2-b]pyridine CAS [1277168-52-1])- | 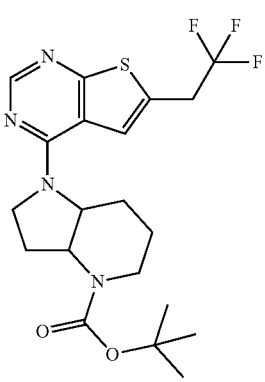 [SMILES: CC(C)(C)OC(=O)N1CCCC2C1CCN2c1ncnc2sc(CC(F)(F)F)cc12] |

Preparation of Intermediate 26:

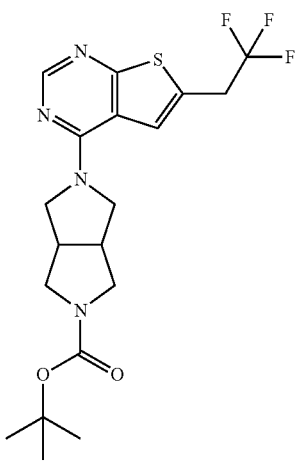 [SMILES: CC(C)(C)OC(=O)N1CC2CN(c3ncnc4sc(CC(F)(F)F)cc34)CC2C1]

Tert-butyl Hexahydropyrrolo[3,4-c]pyrrole-2(1H)-carboxylate (3 g, 133 mmol), (CAS[141449-85-6]), 4-chloro-6-(2,2,2-trifluoroethyl)thieno[2,3-d]pyrimidine (CAS [1628317-85-0]) (3.5 g, 13.9 mmol) (prepared as described in Journal of Medicinal Chemistry (2016), 59(3), 892-913); DIEA (2 mL, 11.9 mmol) in ACN (10 mL) were heated at 80° C. overnight. The mixture was cooled to rt, poured into ice water then, EtOAc was added and extracted twice with EtOAc. The organic layer was separated, washed with water, dried over MgSO$_4$, filtered and evaporated till dryness. The residue (1.83 g) was crystallized from Et$_2$O, the precipitate was filtered and dried to give 1.6 g of intermediate 26.

The intermediate in the Table below was prepared using an analogous method as described for the preparation of intermediate 26, starting from the indicated starting materials

| INTERMEDIATE NUMBER | Structure |
|---|---|
| Intermediate 27 (from (1S,5S)-3-Boc-3,6-diazabicyclo[3.2.0]heptane (CAS[956276-42-9])) | 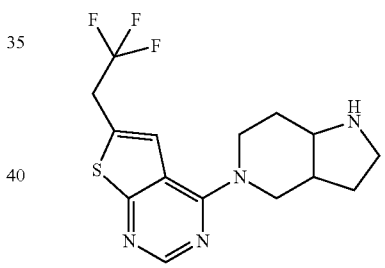 |

Preparation of Intermediate 28

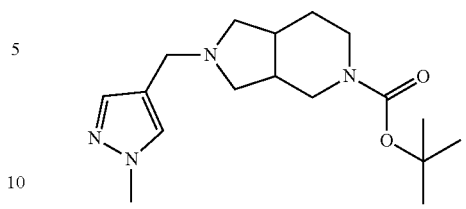

Under N$_2$ flow, a solution of 5-Boc-octahydro-pyrrolo[3,4-c]pyridine (CAS [351370-99-5]) (339 mg; 1.5 mmol) and 1-methyl-1H-pyrazole-4-carbaldehyde (CAS [25016-11-9]) (150 mg; 1.4 mmol) in DCE (5 mL) was stirred at rt. After 10 min, NaBH(OAc)$_3$ (867 mg; 4.1 mmol) was added and the mixture was stirred at rt overnight. The mixture was poured into ice water, basified with a saturated solution of NaHCO$_3$ and DCM was added. The organic layer was separated, washed with brine, dried over MgSO$_4$, filtered and evaporated till dryness. The residue (500 mg) was purified by chromatography over silica gel (Stationary phase: irregular silica 12 g, Mobile phase gradient from: 100% petroleum ether, 0% EtOAc to 0% petroleum ether, 100% EtOAc then 100% EtOAc 0% MeOH to 90% EtOAc, 10% MeOH). The fractions containing product were collected and evaporated to dryness yielding 230 mg (27%) of intermediate 28.

Preparation of Intermediate 3:

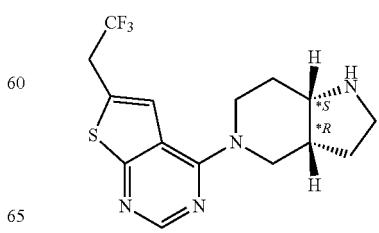

At 0° C., a 4N solution of HCl in dioxane (25 mL, 113 mmol) was added dropwise to a solution of intermediate 1 (5 g; 11.3 mmol) in ACN (40 mL). The mixture was stirred at rt for 1.5 h. The mixture was concentrated then, was poured into ice water, basified with a saturated solution of NaHCO$_3$ and the product was extracted with EtOAc. The organic layer was collected, washed with brine, dried over MgSO$_4$, filtered and evaporated to dryness to give 3 g (yield 78%) of intermediate 3.

Preparation of Intermediate 3 A and Intermediate 3B

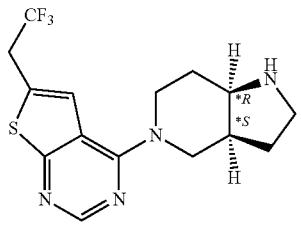 [SMILES: FC(F)(F)Cc1cc2c(N3CC[C@H]4NCC[C@H]4C3)ncnc2s1]

At 0° C., 4N solution of HCl in dioxane (38.5 mL, 154 mmol) was added dropwise to a solution of intermediate 1 (6.81 g; 15.4 mmol) in ACN (50 mL). The mixture was stirred at rt for 1.5 h. The mixture was concentrated and then was poured into ice water, basified with a saturated solution of NaHCO$_3$ and the product was extracted with EtOAc. The organic layer was collected, washed with brine, dried over MgSO$_4$, filtered and evaporated to dryness to give 3.1 g (yield 59%) of intermediate 3 (as yellow oil).

The aqueous layer was saturated with NaHCO$_3$, then extracted with DCM (3 times), dried over MgSO$_4$, filtered and evaporated to dryness to give a further batch of 2.2 g (yield 41%) of intermediate 3 (as yellow oil). The two batches were submitted to chiral SFC (Stationary phase: Chiralpak AD-H 5 μm 250*30 mm, Mobile phase: 78% CO$_2$, 22% MeOH (0.50% iPrNH$_2$)). The fractions containing product were collected and evaporated to dryness yielding 2.15 g (yield 42%) of intermediate 3 A and 2.23 g (yield 42%) of intermediate 3B.

The intermediates in the Table below were prepared using an analogous method as described for the preparation of intermediate 3, starting from the indicated starting materials

| INTERMEDIATE NUMBER | Structure |
| --- | --- |
| Intermediate 4 (from intermediate 2) | |
| Intermediate 29 (from intermediate 20) | |
| Intermediate 30 (from intermediate 26) | 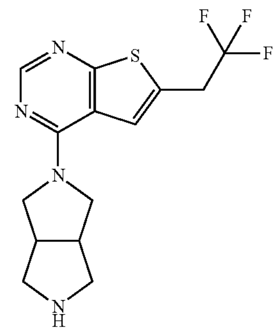 [SMILES: FC(F)(F)Cc1cc2c(N3CC4CNCC4C3)ncnc2s1] |
| Intermediate 31 (from intermediate 27) | 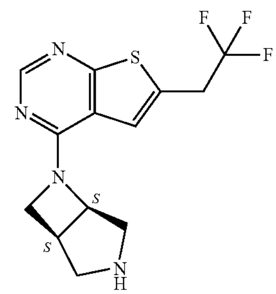 |
| Intermediate 32 (from intermediate 21A) | 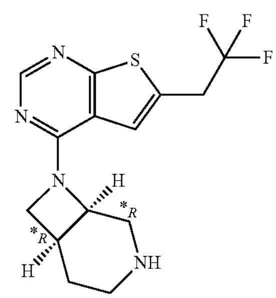 [SMILES: FC(F)(F)Cc1cc2c(N3C[C@@H]4CCNC[C@@H]43)ncnc2s1] |
| Intermediate 33 (from intermediate 21B) | 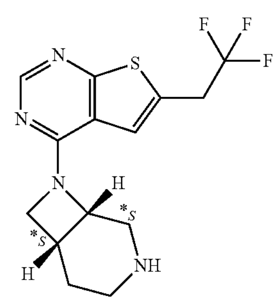 [SMILES: FC(F)(F)Cc1cc2c(N3C[C@H]4CCNC[C@H]43)ncnc2s1] |
| Intermediate 34 (from intermediate 23) | 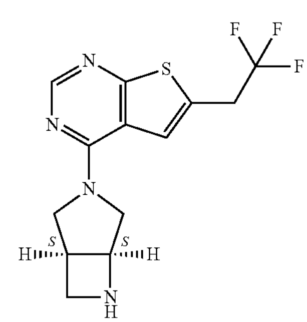 |

| INTERMEDIATE NUMBER | Structure |
| --- | --- |
| Intermediate 35 (from intermediate 24 | 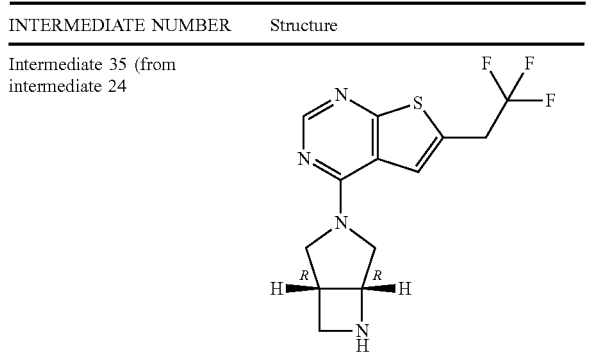 |

Preparation of Intermediate 36

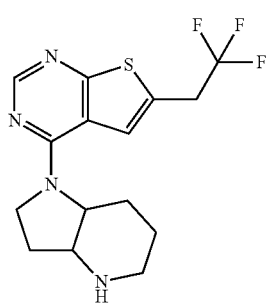 [SMILES: FC(F)(F)Cc1cc2c(N3CCC4NCCCC43)ncnc2s1]

At 0° C., 4N solution of HCl in dioxane (10 mL, 40 mmol) was added dropwise to a solution of intermediate 25 (530 mg; 1.2 mmol) in DCM (2 mL). The mixture was stirred at rt for 1 h. The mixture was concentrated to give 500 mg of intermediate 36.

The intermediate in the Table below was prepared using an analogous method as described for the preparation of intermediate 36, starting from the indicated starting materials

| INTERMEDIATE NUMBER | Structure |
| --- | --- |
| Intermediate 37 (from intermediate 28 ) | 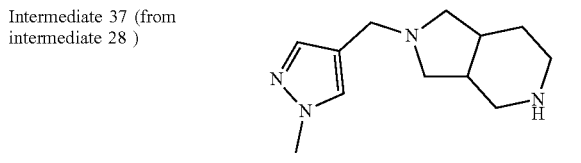 |

Preparation of Intermediate 5:

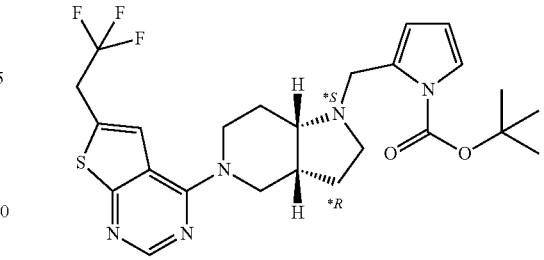

Intermediate 3A (100 mg, 0.29 mmol), tert-butyl 2-(chloromethyl)-1H-pyrrole-1-carboxylate (CAS[1420899-93-9] prepared as described in Chemical Communications 2015, 51(18), 3842-3845) (95 mg, 0.44 mmol), and $K_2CO_3$ (121 mg, 0.88 mmol) in ACN (8 mL) were stirred at rt for 48 h. The reaction mixture was poured into ice water and EtOAc was added. The organic layer was separated, washed with brine, dried over $MgSO_4$, filtered and evaporated till dryness to give a residue (0.15 g). The residue was purified by chromatography over silica gel (Stationary phase: irregular SiOH 15-40 mm 24 g, Mobile phase: 98% DCM, 2% MeOH). The fractions containing product were collected and evaporated to dryness yielding 40 mg (yield 26%) of intermediate 5.

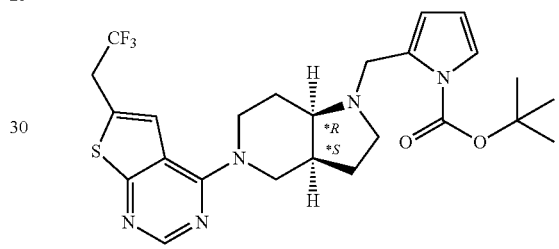

Preparation of Intermediate 45:
Under $N_2$ flow, intermediate 3B (300 mg; 0.9 mmol) and N-boc-pyrrole-2-carboxaldehyde (CAS [161282-57-1]) (206 mg; 1.0 mmol) in DCM (12 mL) was stirred at rt. After 4 h, the mixture was cooled to 5° C. and $NaBH(OAc)_3$ (372 mg; 1.7 mmol) was added and the mixture was stirred at rt for 24 h. The mixture was poured into ice water, a saturated solution $NaHCO_3$ and DCM was added. The organic layer was separated, washed with brine, dried over $MgSO_4$, filtered and evaporated till dryness. The residue (500 mg) was purified by chromatography over silica gel (Stationary phase: irregular silica 24 g, Mobile phase: 0.1% $NH_4OH$, 98% DCM, 2% MeOH). The fractions containing product were collected and evaporated to dryness yielding 140 mg of intermediate 45.

The intermediate in the Table below was prepared using an analogous method as described for the preparation of intermediate 45, starting from the indicated starting materials

| INTERMEDIATE NUMBER | Structure |
| --- | --- |
| Intermediate 38 (from intermediate 3 and 1H-Pyrazole-4-carboxaldehyde, 1-[2-(1,3-dihydro-1,3-dioxo-2H-isoindol-2yl)ethyl] (CAS [1899833-28-3])) | 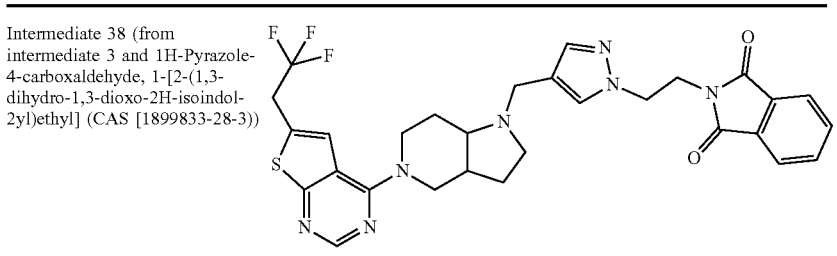 |

Preparation of Intermediate 39

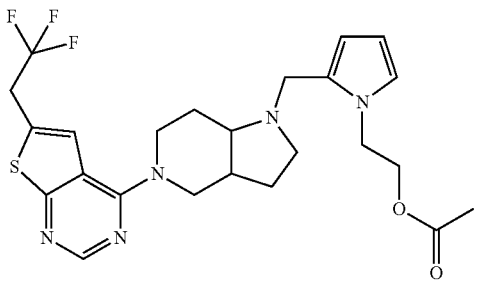 [SMILES: CC(=O)OCCn1cccc1CN1CCC2CN(c3ncnc4sc(CC(F)(F)F)cc34)CCC21]

Under nitrogen flow, 2-(2-formyl-1H-pyrrol-1-yl)ethyl acetate (274 mg, 1.35 mmol) was added to a solution of intermediate 3 (500 mg, 1.23 mmol) in dry DCM (20 mL). The mixture was stirred at room temperature for 2 h. Then, NaBH(OAc)$_3$ (520 mg, 2.45 mmol) was added and the mixture was stirred at rt overnight. The reaction mixture was poured into ice water and the mixture was separated. The aqueous layer was extracted with DCM twice. The organic layers were combined, washed with brine then, dried over MgSO$_4$ and evaporated to give 250 mg (yield 67%) of intermediate 39.

The intermediate in the Table below was prepared using an analogous method as described for the preparation of intermediate 39, starting from the indicated starting materials

| INTERMEDIATE NUMBER | Structure |
|---|---|
| Intermediate 40 (from intermediate 3B) | 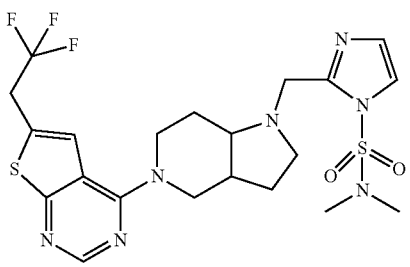 [SMILES: CN(C)S(=O)(=O)n1ccnc1CN1CCC2CN(c3ncnc4sc(CC(F)(F)F)cc34)CCC21] |

Preparation of Intermediate 41:

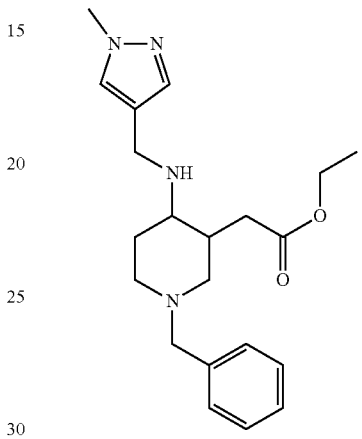

2-(chloromethyl)-N,N-dimethyl-1H-imidazole-1-sulfonamide (CAS [935862-81-0]) (67 mg, 0.51 mmol) was added to a solution of intermediate 3 (300 mg, 0.9 mmol) and K$_2$CO$_3$ (363 mg, 2.6 mmol) in ACN (10 mL). The solution was heated at 90° C. overnight. The reaction mixture was poured into ice water and EtOAc was added. The organic layer was separated, washed with brine, dried over MgSO$_4$, filtered and evaporated till dryness. The residue (500 mg) was purified by chromatography over silica gel (Stationary phase: irregular bare silica 24 g, Mobile phase: 0.1% NH$_4$OH, 97% DCM, 3% MeOH). The fractions containing product were collected and evaporated to dryness yielding 250 mg of intermediate 41.

Preparation of Intermediate 42:

Under N$_2$ flow, a solution of (1-Benzyl-4-oxo-piperidin-3-yl)-acetic acid ethyl ester (CAS [6947-75-7]) (3.7 g; 10 mmol) and (1-Methyl-1H-pyrazol-4-yl)methanamine (CAS [400877-05-6]) (1.4 g; 12 mmol) and acetic acid (300 mg; 5 mmol) in DCE (70 mL) was stirred at rt. After 30 min, NaBH(OAc)$_3$ (10.6 g; 50 mmol) was added and the mixture was stirred at rt overnight. The mixture was poured into ice water and basified with a saturated solution of NaHCO$_3$ (pH=8). DCM was added and the organic layer was separated, washed with brine, dried over MgSO$_4$, filtered and evaporated till dryness. The residue (5 g) was purified by chromatography over silica gel (Stationary phase: irregular bare silica 80 g, Mobile phase gradient: 100% DCM, 0% MeOH to 75% DCM, 25% MeOH). The fractions containing product were collected and evaporated to dryness and dried giving 3.34 g (yield 90%) of intermediate 42.

Preparation of Intermediate 43:

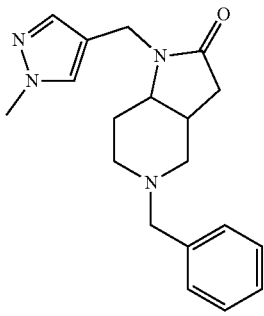 [SMILES: Cn1cc(CN2C(=O)CC3CN(Cc4ccccc4)CCC32)cn1]

Under $N_2$ flow, NaH (1.1 g; 27 mmol) was added to a solution of intermediate 42 (3.34 g; 9 mmol) in THF (100 mL) at rt. The reaction mixture was heated at 80° C. for 3 h. The mixture was poured into ice water, a solution of $NH_4Cl$ and EtOAc were added. The organic layer was separated, washed with brine, dried over $MgSO_4$, filtered and evaporated till dryness. The residue (3.5 g) was purified by chromatography over silica gel (Stationary phase: irregular bare silica 80 g, Mobile phase gradient: 100% DCM, 0% MeOH to 85% DCM, 15% MeOH). The fractions containing product were collected and evaporated to dryness and dried giving 2.37 g (yield 81%) of intermediate 43.

Preparation of Intermediate 44:

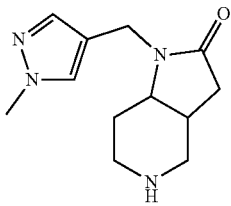 [SMILES: Cn1cc(CN2C(=O)CC3CNCCC32)cn1]

A mixture of intermediate 43 (2.37 g; 7.3 mmol) in MeOH (50 mL) was hydrogenated at 20° C. (50 psi) with Palladium on activated carbon (2 g; 1.9 mmol). After uptake of Hydrogen (1 eq), the catalyst was filtered off and the filtrate was evaporated to give 1.5 g (yield 88%) of intermediate 44.

Preparation of Intermediate

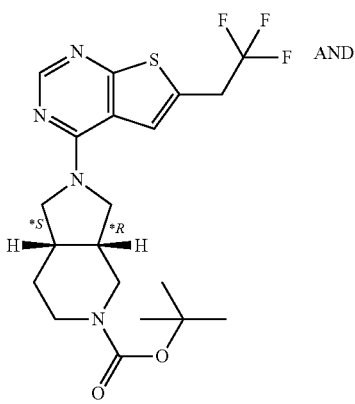

7A

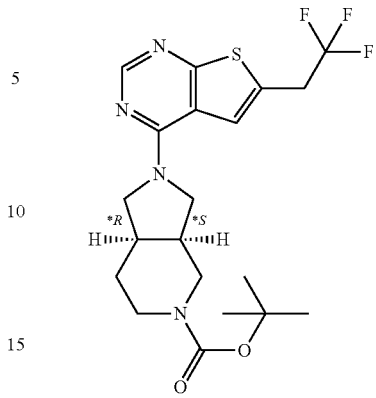

7B (3aR,7aS)-octahydro-pyrrolo[3,4-c]pyridine-5-carboxylate cis relative mixture (CAS[1257389-94-8]) (5.1 g; 22.5 mmol); 4-chloro-6-(2,2,2-trifluoroethyl)thieno-[2,3-d]pyrimidine (CAS[1628317-85-0]) (5.2 g, 20.5 mmol), DIEA (10.7 mL, 61.5 mmol) in iPrOH (150 mL) were heated at 90° C. overnight. The mixture was cooled to rt then concentrated. The residue was poured into ice water then DCM was added. The organic layer was separated, washed with water, dried over $MgSO_4$, filtered and evaporated till dryness. The residue (10.64 g) was purified by chromatography over silica gel (Stationary phase: irregular SiOH 40 μm 220 g, mobile phase: 60% heptane, 35% EtOAc). The fractions containing product were collected and evaporated to dryness. The resulting residue (7.3 g) was separated by chiral SFC (Stationary phase: Chiralpak AD-H 5 μm 250*30 mm, Mobile phase: 76% $CO_2$, 24% i-PrOH). The fractions containing product were collected and evaporated to dryness yielding 3.54 g of enantiomer intermediate 7A and 3.71 g of enantiomer intermediate 7B.

Alternative Preparation of Intermediate 7A

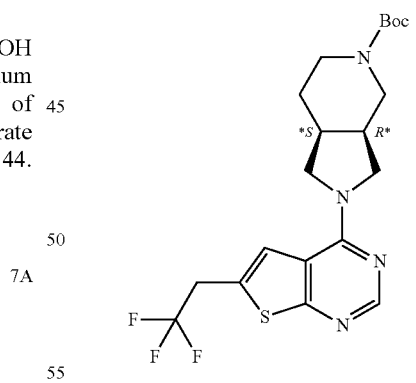

To a solution of 4-chloro-6-(2,2,2-trifluoroethyl)thieno[2,3-d]pyrimidine (4.00 g, 15.0 mmol) in $^i$PrOH (30 mL) was added tert-butyl octahydro-5H-pyrrolo[3,4-c]-pyridine-5-carboxylate (3.90 g, 17.3 mmol) and DIPEA (6.20 g, 48.0 mmol). After stirring at room temperature for 2 h, the solvent was removed to get the crude product. The material was purified by flash chromatography. The obtained mixture was separated by SFC: SFC80 (Waters) (AD 2.5*25 cm, 10 um) column; mobile phase: A: Supercritical $CO_2$, B:IPA/ACN/DEA=80/20/0.2, gradient A:B=65/35 hold; flow 70 mL/min; column temperature 25° C.; stack injections; backpressure 100 bar. The desired fractions were collected and the solvent was evaporated. Yield: 3.00 g of intermediate 7A (6.78 mmol; 42.8% yield).

Preparation of Intermediate 8:

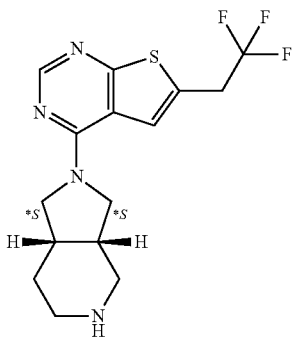 [SMILES: FC(F)(F)Cc1cc2c(N3C[C@H]4CCNC[C@H]4C3)ncnc2s1]

At 0° C., a 4N solution of HCl in dioxane (18.6 mL, 74.6 mmol) was added dropwise to a solution of intermediate 7A (3.3 g; 7.4 mmol) in DCM (25 mL). The mixture was stirred at rt for 3 h. The mixture was concentrated then was poured into ice water basified with a saturated solution of NaOH 3N, and the product was extracted with DCM. The organic layer was collected, dried over MgSO$_4$, filtered and evaporated to dryness. The residue (3.2 g) was purified by chromatography over silica gel (Stationary phase: irregular SiOH 40 μm 40 g, mobile phase: 90% DCM, 10% MeOH (+10% NH$_4$OH)). The fractions containing product were collected and evaporated to dryness yielding 2.17 g (yield 85%) of intermediate 8.

The intermediate in the Table below was prepared using an analogous method as described for the preparation of compound 8, starting from the indicated starting materials

| INTERMEDIATE NUMBER | Structure |
| --- | --- |
| Intermediate 9 (from intermediate 7B) | 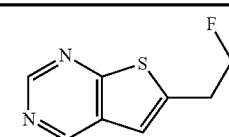 |

Preparation of Intermediate 10

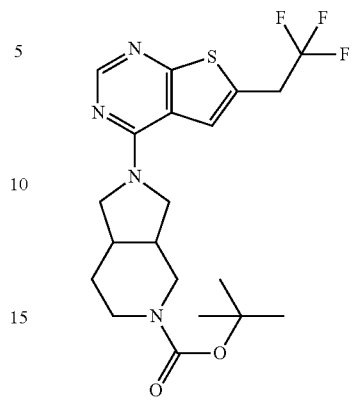

5-boc-octahydro-pyrrolo[3,4-c]pyridine (CAS[351370-99-5]) (1.2 g; 5.4 mmol); 4-chloro-6-(2,2,2-trifluoroethyl)thieno[2,3-d]pyrimidine (CAS [1628317-85-0]) (1.3 g, 5 mmol), DIEA (2.7 mL, 15.2 mmol) in iPrOH (20 nit) were heated at 90° C. overnight. The mixture was cooled to rt then concentrated. The residue (2.5 g) was purified by chromatography over silica gel, (mobile phase gradient from: 100% petroleum ether, 0% EtOAc to 10% petroleum ether, 90% EtOAc). The fractions containing product were collected and evaporated to dryness yielding 200 mg of intermediate 10 and 600 mg of an impure fraction of intermediate 10 (was not pure).

Preparation of Intermediate 11:

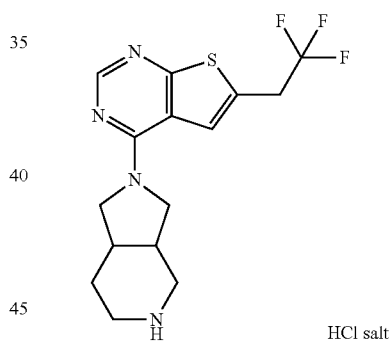

HCl salt

At 0° C., a 4N solution of HCl in dioxane (8 mL, 32 mmol) was added dropwise to a solution of intermediate 10 (600 mg; 1.4 mmol) in DCM (1 mL). The mixture was stirred at rt for 1.5 h. The mixture was evaporated till dryness yielding 720 mg of intermediate 11 as HCl salt.

Preparation of Intermediate 12

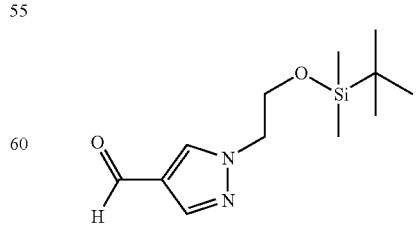

2-bromoethoxy-t-butyldimetylsilane (CAS [86864-60-0]) (2.4 mL; 11.4 mmol) was added to a solution of 1H-pyrazole-4-carbaldehyde (CAS [35344-95-7]) (910 mg; 9.5 mmol) and K$_2$CO$_3$ (1.6 g; 11.4 mmol) in ACN (18 mL). The reaction was heated at 80° C. for 2 h. The reaction mixture was partitioned between a saturated solution of NaHCO$_3$ and EtOAc. The organic layer was separated, dried over MgSO$_4$, filtered and evaporated till dryness. The residue was purified by chromatography over silica gel (Stationary phase: irregular SiOH 40 μm 120 g, mobile phase gradient from: 100% DCM, 0% MeOH to 95% DCM, 5% MeOH). The fractions containing product were collected and evaporated to dryness yielding 1.6 g (65%) of intermediate 12.

Preparation of Intermediate 13

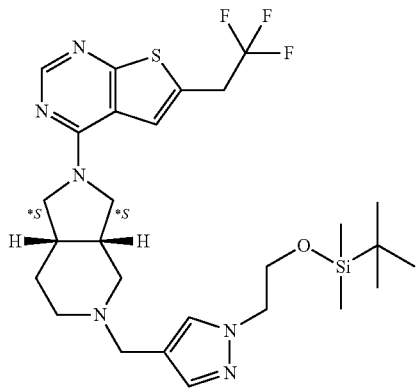 [SMILES: CC(C)(C)[Si](C)(C)OCCn1cc(CN2CC[C@@H]3CN(c4ncnc5sc(CC(F)(F)F)cc45)C[C@@H]3C2)cn1]

Under N$_2$ flow, a solution of intermediate 8 (112 mg; 0.3 mmol) and intermediate 12 (100 mg; 0.4 mmol) in THF (5 mL) was stirred at rt. After 3 h, NaBH(OAc)$_3$ (139 mg; 0.7 mmol) was added and the mixture was stirred at rt overnight. The mixture was poured into ice water, basified with a solution of NaOH 3N and EtOAc was added. The organic layer was separated, washed with brine, dried over MgSO$_4$, filtered and evaporated till dryness. The residue (170 g) was purified by chromatography over silica gel (Stationary phase: irregular silica 12 g, Mobile phase gradient from: 0.1% NH$_4$OH, 97% DCM, 3% MeOH to 0.1% NH$_4$OH, 95% DCM, 5% MeOH). The fractions containing product were collected and evaporated to dryness yielding 71 mg of intermediate 13.

Preparation of Intermediate 16

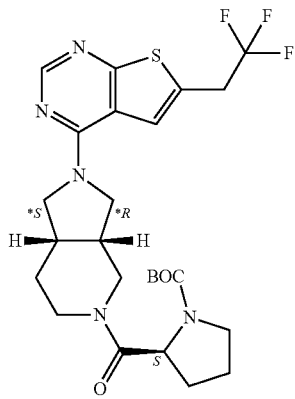

Under N$_2$ flow at 10° C., HBTU (101 mg; 0.3 mmol) was added to a solution of Boc-L-Proline (CAS [15761-39-4]) (57 mg; 0.3 mmol) and DIEA (0.2 mL; 1.3 mmol) in DMF (3 mL). The solution was stirred at 10° C. for 30 min then, intermediate 8 (100 mg; 0.3 mmol) was added and the reaction mixture was stirred at rt for 15 h. The solution was poured into cooled water, a 10% solution of K$_2$CO$_3$ was added and EtOAc. The organic layer was separated, washed with brine, dried over MgSO$_4$, filtered and evaporated till dryness to give 114 mg of intermediate 16. The intermediate was used without any purification for the next step.

The intermediates in the Table below were prepared using an analogous method as described for the preparation of intermediate 16 starting from the indicated starting materials

| INTERMEDIATE NUMBER | Structure |
| --- | --- |
| Intermediate 17 (from intermediate 8 and (S)-5-boc azaspiro[2.4]heptane-6-carboxylic acid (CAS[1129634-44-1])) | 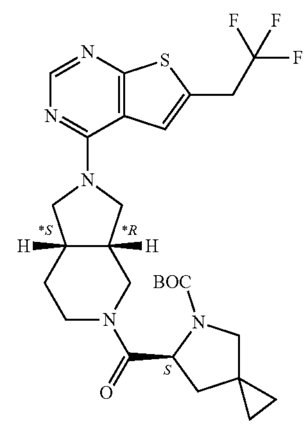 |
| Intermediate 18 (from intermediate 9 and (S)-5-boc azaspiro[2.4]heptane-6-carboxylic acid (CAS[1129634-44-1])) | 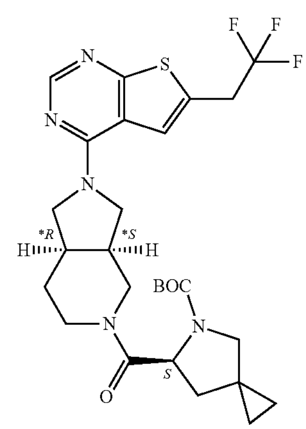 |
| Intermediate 19 (from intermediate 9 and boc L-proline (CAS[15761-39-4])) | 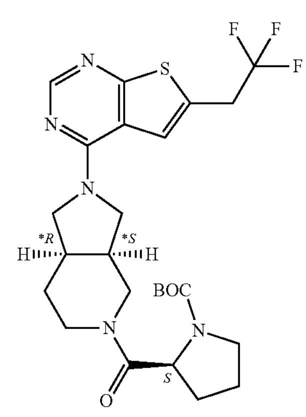 |

Preparation of Intermediate 47 (TFA Salt of Intermediate 8)

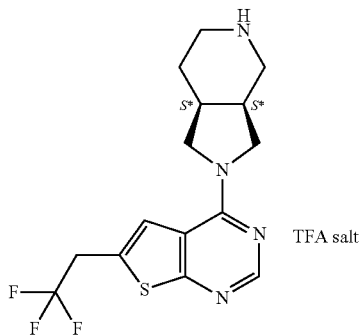 [SMILES: FC(F)(F)Cc1cc2c(N3C[C@H]4CCNC[C@H]4C3)ncnc2s1] TFA salt

To a solution of Intermediate 7A (3.00 g, 6.78 mmol) in CH₃OH (100 mL) was added TFA (10 ml). After stirring at room temperature overnight. The solvent was removed to get intermediate 47 (2.70 g, 4.26 mmol, TFA salt), which was used in the next step without further purification.

Preparation of Intermediate 48

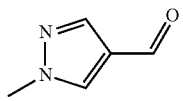

To a solution of 1H-pyrazole-4-carbaldehyde (1.00 g, 10.4 mmol) in DMF (40 mL) was added iodomethane (1.48 g, 10.4 mmol) and Cs₂CO₃ (10 g, 31.2 mmol). After stirring at 60° C. overnight, the reaction mixture was added water (20 mL) and extracted with EtOAc (50 mL×3). The organic phase was washed with brine, dried over Na₂SO₄ and concentrated to give intermediate 48 (1.00 g, 87% yield).

Preparation of Intermediate 49

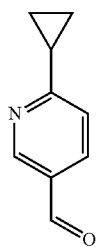

To a solution of 6-bromonicotinaldehyde (500 mg, 2.70 mmol) in 1,4-dioxane (10 mL) was added cyclopropylboronic acid (258 mg, 8.10 mmol), Cs₂CO₃ (2.616 g, 8.10 mmol), and Pd(dppf)Cl₂ (50 mg, 10%). The mixture was stirred overnight at 90° C. Subsequently, the mixture was diluted with H₂O, and extracted twice with EA. The combined extracts were concentrated in vacuo and purified by prep-TLC to yield intermediate 49 (300 mg, 75.2% yield).

Preparation of Intermediate 50

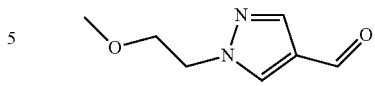

To a solution of 1H-pyrazole-4-carbaldehyde (500 mg, 5.20 mmol) in DMF (20 mL) was added 1-bromo-2-methoxyethane (713 mg, 5.2 mmol) and Cs₂CO₃ (3.40 g, 10.4 mmol). After stirring at 60° C. overnight, water (20 mL) was added to the mixture and the mixture was extracted with EtOAc (50 ml×3). The organic phase was washed with brine, dried over Na₂SO₄ and concentrated to yield intermediate 50 (520 mg, 65% yield).

Preparation of Intermediate 51

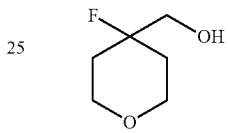

To a mixture of methyl 4-fluorotetrahydro-2H-pyran-4-carboxylate (840 mg, 5.18 mmol) in THF (20 mL) was added LAH (394 mg, 10.36 mmol) under N₂ at 0° C. The mixture was stirred at 0° C. for 3 h. 10 ml saturated NH₄Cl aqueous solution was added carefully. The mixture was filtered, and extracted with EA (10 mL*2). The combined organic layer was dried over Na₂SO₄, filtered and evaporated to yield intermediate 51 ((4-fluorotetrahydro-2H-pyran-4-yl)methanol) (550 mg, 4.10 mmol, 80% yield) as oil which was used directly in the next step.

H NMR CD₃OD (400 MHz): δ 3.81-3.85 (m, 2H), 3.70-3.76 (m, 2H), 3.64 (s, 1H), 3.59 (s, 1H), 1.67-1.90 (m, 4H).

Preparation of Intermediate 52

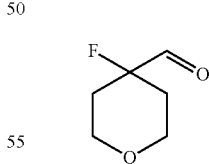

To a mixture of intermediate 51 (550 mg, 4.10 mmol) in acetone (50 mL) was added IBX (4.59 g, 16.4 mmol). The mixture was stirred overnight at 60° C. The mixture was cooled to room temperature and filtered. The solution was concentrated and the residue was purified by column chromatography on silica gel (eluent: EA:PE=10:1) to yield intermediate 52 (250 mg, 1.896 mmol, 45% yield) as oil.

Preparation of Intermediate 53
See table of Example B10.
Preparation of Intermediate 54

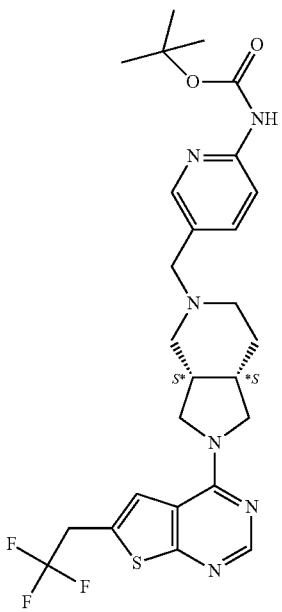 [SMILES: CC(C)(C)OC(=O)Nc1ccc(CN2CC[C@@H]3CN(c4ncnc5sc(CC(F)(F)F)cc45)C[C@@H]3C2)cn1]

To a mixture of intermediate 47 (170 mg, 0.5 mmol) and tert-butyl (5-formylpyridin-2 yl)carbamate (166.5 mg, 0.75 mmol) in DCM (10 mL) was added titanium(IV) isopropoxide (284 mg, 1 mmol). The mixture was stirred at room temperature for 1 h, and then $NaBH(OAc)_3$ (212 mg, 1 mmol) was added. The reaction mixture was stirred at room temperature for 4 h. The residue was diluted in water (20 mL), extracted with DCM (30 mL×2), dried over $Na_2SO_4$ and concentrated to yield intermediate 54 (140 mg, 0.25 mmol, 50% yield) as oil, which was used in the next step without further purification.

B. Preparation of the Compounds

Example B1

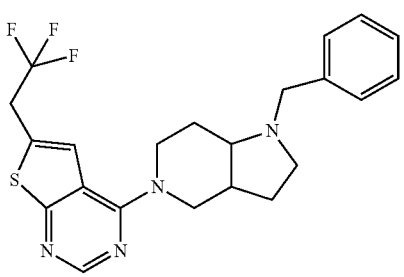 [SMILES: FC(F)(F)Cc1cc2c(N3CCC4C(CCN4Cc4ccccc4)C3)ncnc2s1]

Preparation of Compound 1:

Benzyl bromide (26.9 mg, 0.16 mmol) and then potassium carbonate (59.3 mg, 0.43 mmol) were successively added to a solution of intermediate 3A (50 mg, 0.14 mmol) in ACN (1 mL) and the mixture was stirred at rt overnight. The mixture was then combined with another experiment on same quantities and evaporated to give a yellow oil. The residue was purified by chromatography over silica gel (column C18 150*25 mm*5 um, mobile phase gradient: from 37% water (0.05% ammonia hydroxide v/v) and 63% AcN to 7% water (0.05% ammonia hydroxide v/v) and 93% AcN). The fractions containing product were collected and evaporated to dryness. The residue was then lyophilized to give 30 mg of compound 1 (24% yield) as a yellow solid.

$^1$H NMR (400 MHz, CHLOROFORM-d) d=8.43 (s, 1H), 7.42-7.27 (m, 6H), 3.97 (br d, J=12.3 Hz, 3H), 3.78 (br s, 2H), 3.63 (q, J=10.2 Hz, 2H), 3.41 (br s, 1H), 2.96 (br s, 1H), 2.79 (br s, 1H), 2.54 (br s, 1H), 2.22 (br s, 1H), 2.07-1.84 (m, 3H), 1.57-1.44 (m, 1H).

The compounds in the Table below were prepared using an analogous method as described for the preparation of compound 1, starting from the respective starting materials

| COMPOUND NUMBER | Structure |
|---|---|
| Compound 2 (from intermediate 4) | 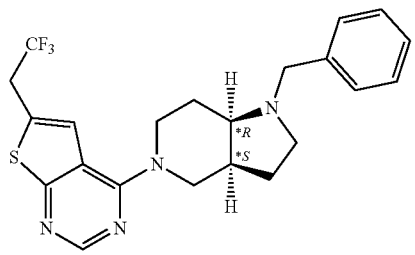 [SMILES: FC(F)(F)Cc1cc2c(N3CC[C@@H]4[C@@H](CCN4Cc4ccccc4)C3)ncnc2s1] |

Example B2

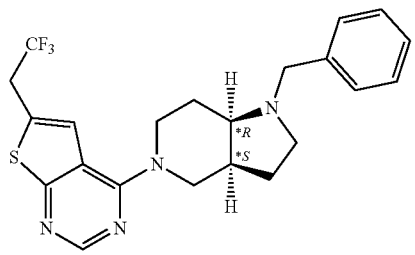 [SMILES: FC(F)(F)Cc1cc2c(N3CC[C@@H]4[C@@H](CCN4Cc4ccccc4)C3)ncnc2s1]

$C_{22}H_{23}F_3N_4S.1.72HCl.1.25H_2O$

Preparation of Compound 3 and 3A:

Benzyl bromide (0.14 mL, 1.2 mmol) was added to a solution of intermediate 3B (372 mg, 1.1 mmol) and $K_2CO_3$ (450 mg, 3.26 mmol) in ACN (8 mL). The mixture was stirred at rt overnight. The reaction mixture was poured into ice water and EtOAc was added. The organic layer was separated, washed with brine, dried over $MgSO_4$, filtered and evaporated till dryness. The residue was purified by chromatography over silica gel (Stationary phase: irregular SiOH 15-40 μm 300 g, Mobile phase: Gradient from 98% DCM, 2% MeOH (+10% $NH_4OH$) to 96% DCM, 4% MeOH (+10% $NH_4OH$)). The fractions containing product were collected and evaporated to dryness yielding 315 mg (yield 67%) of compound 3. The compound was dissolved in 5 mL of acetone, and HCl 4N in dioxane (2 eq, 0.36 mL, 1.45 mmol) was added dropwise at 10° C. $Et_2O$ was added and, after 30 min, a precipitate was filtered and dried giving 185 mg (yield 33%) of compound 3 as a HCl salt ($C_{22}H_{23}F_3N_4S.1.72HCl.1.25H_2O$). The mother layer was evaporated till dryness to give of a residue that was basified with $NH_4OH$ and extracted with DCM. The organic layer was separated, dried over $MgSO_4$, filtered and evaporated till dryness to give 100 mg (yield 21%) of a fraction of the free base of compound 3 (compound 3A).

The compounds in the Table below were prepared by using an analogous method as described for the preparation of compound 3, starting from the respective starting materials

| COMPOUND NUMBER | Structure |
|---|---|
| Compound 4 as an HCl salt (1.7HCl•1.1H$_2$O) (from intermediate 3A) (MP = 128° C. / kofler) | 1.7HCl•1.1H$_2$O |
| Compound 5 as an HCl salt (from intermediate 3A) | HCl salt |
| Compound 6 as an HCl salt (from intermediate 3B) (MP = 140° C. / kofler) | HCl salt |
| Compound 7 as an HCl salt (1.5HCl•1.5H$_2$O) (from intermediate 3A) (MP = 135° C. / kofler) | 1.5HCl•1.5H$_2$O |

Example B3

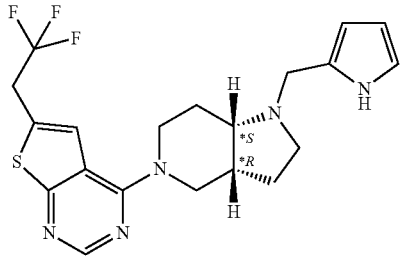 [SMILES: FC(F)(F)Cc1cc2c(N3CC[C@H]4[C@H](CCN4Cc4ccc[nH]4)C3)ncnc2s1]

Preparation of Compound 8:

At 0° C., a 4N solution of HCl in dioxane (0.19 mL, 0.08 mmol) was added dropwise to a solution of intermediate 5 (40 mg, 0.08 mmol) in dioxane (2 mL) and stirred at rt for 4 h. Then, an additional quantity of 4N solution of HCl in dioxane (0.95 mL, 0.04 mmol) was added and the mixture was stirred at rt overnight. The reaction mixture was concentrated. Then, the residue was taken-up with DCM, washed with a solution of NaHCO$_3$ (10%), and the organic layer was decanted, dried over MgSO$_4$, filtered and evaporated to dryness. The residue was purified by chromatography over silica gel (Stationary phase: irregular SiOH 15-40 μm log Mobile phase: Gradient from 0.1% NH$_4$OH, 97% DCM, 3% MeOH to 0.1% NH$_4$OH, 90% DCM, 10% MeOH). The fractions containing product were collected and evaporated to dryness yielding 25 mg (yield 77%) of compound 8.

The compounds in the Table below were prepared using an analogous method as described for the preparation of compound 8, starting from the respective starting materials

| COMPOUND NUMBER | Structure |
|---|---|
| Compound 85 (from intermediate 45) | 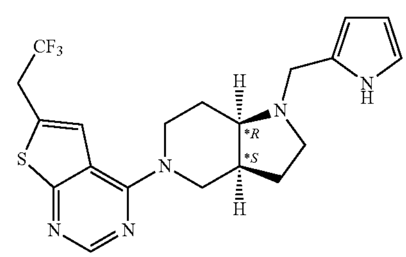 [SMILES: FC(F)(F)Cc1cc2c(N3CC[C@@H]4[C@@H](CCN4Cc4ccc[nH]4)C3)ncnc2s1] |
| Compound 84 (from intermediate 53) | 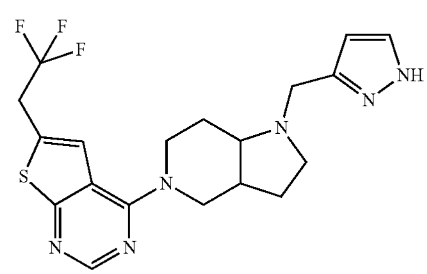 [SMILES: FC(F)(F)Cc1cc2c(N3CCC4C(CCN4Cc4cc[nH]n4)C3)ncnc2s1] |

Example B4

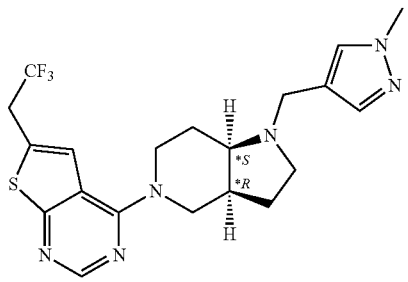 [SMILES: Cn1cc(CN2CC[C@H]3CN(c4ncnc5sc(CC(F)(F)F)cc45)CC[C@H]32)cn1]

2.6HCl.1.1H₂O
Preparation of Compound 9:

4-(Chloromethyl)-1-methyl-1H-pyrazole (67 mg, 0.51 mmol) was added to a solution of intermediate 3B (135 mg, 0.39 mmol) and K₂CO₃ (164 mg, 1.18 mmol) in ACN (4 mL). The yellow solution was stirred at rt for 24 h. The reaction mixture was poured into ice water and EtOAc was added. The organic layer was separated, washed with brine, dried over MgSO₄, filtered and evaporated till dryness. The residue was purified by chromatography over silica gel (Stationary phase: irregular bare silica 40 g, Mobile phase: 0.1% NH₄OH, 95% DCM, 5% MeOH). The fractions containing product were collected and evaporated to dryness yielding 98 mg of compound 9. The compound was dissolved in acetone, and converted into hydrochloric acid salt by treatment with HCl, the precipitate was filtered and the solid was dried providing 64 mg (yield 29%) of compound 9 as a HCl salt (2.6HCl.1.1H₂O).

¹H NMR (500 MHz, DMSO-d₆) δ ppm 11.00 (br s, 1H) 8.47 (s, 1H) 7.94 (s, 1H) 7.74 (s, 1H) 7.65 (s, 1H) 4.24-4.41 (m, 4H) 4.04-4.12 (m, 4H) 3.86 (s, 3H) 3.65-3.76 (m, 2H) 3.35-3.46 (m, 1H) 2.95-3.07 (m, 1H) 2.73-2.85 (m, 1H) 2.14-2.33 (m, 2H) 1.62-1.75 (m, 1H)

The compounds in the Table below were prepared using an analogous method as described for the preparation of compound 9, starting from the respective starting materials

| COMPOUND NUMBER | Structure |
|---|---|
| Compound 10 (from intermediate 3B) | *(structure shown)* |
| Compound 11 (from intermediate 3A) | *(structure shown)* |
| Compound 12 as a HCl salt (1.8 HCl·2.7 H₂O) (from intermediate 3B) | *(structure shown)* 1.8HCl·2.7H₂O |
| Compound 12B as a HCl salt (from intermediate 3A) | *(structure shown)* As HCl salt |
| Compound 13 (from intermediate 3A) | *(structure shown)* |
| Compound 14 as a HCl salt (from intermediate 3A) | *(structure shown)* |
| Compound 15, as an oil (from intermediate 3) | *(structure shown)* |

| COMPOUND NUMBER | Structure |
|---|---|
| Compound 18 (from intermediate 30) | 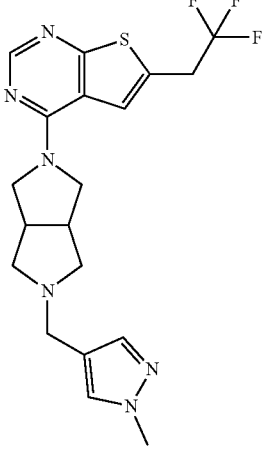 |

Example B5

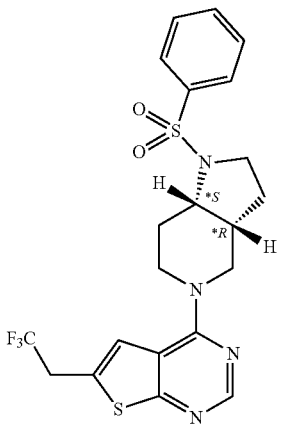 [SMILES: O=S(=O)(c1ccccc1)N1CC[C@@H]2CN(c3ncnc4sc(CC(F)(F)F)cc34)CC[C@@H]21]

0.6HCl.0.4H₂O

Preparation of Compound 16

Benzenesulfonyl chloride (45 μL, 0.32 mmol) was added to a solution of intermediate 3A (0.1 g, 0.29 mmol) and $K_2CO_3$ (120 mg, 0.88 mmol) in ACN (3 mL). The mixture was stirred at rt overnight. The reaction mixture was poured into ice water and EtOAc was added. The organic layer was separated, washed with brine, dried over $MgSO_4$, filtered and evaporated till dryness. The residue was purified by chromatography over silica gel (Stationary phase: irregular bare silica 40 g, Mobile phase: 62% Heptane, 3% MeOH (+10% $NH_4OH$), 35% EtOAc). The product containing fractions were collected and evaporated to dryness yielding 105 mg (yield 74%) of compound 16. The compound was dissolved in acetone and converted into hydrochloric acid salt by treatment with HCl, the precipitate was filtered and the solid was dried providing 70 mg (yield 47%) of compound 16 as a HCl salt ($C_{21}H_{21}F_3N_4O_2S_2$.0.6HCl.0.4H₂O) (MP=152° C./kofler).

The compound in the Table below was prepared using an analogous method as described for the preparation of compound 16, starting from the respective starting materials.

| COMPOUND NUMBER | Structure |
|---|---|
| Compound 17 as a HCl salt (0.9 HCl•0.3 H₂O) (from intermediate 3 enantiomer B) | 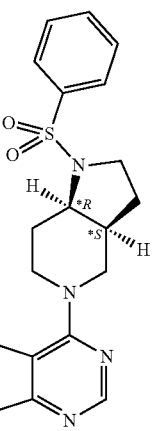 |

Example B6

Preparation of Compound 36

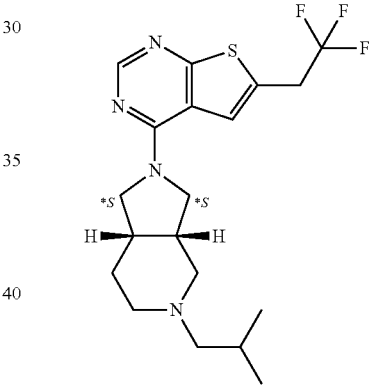

Under $N_2$ flow, a solution of intermediate 8 (250 mg; 0.7 mmol) and isobutyraldehyde (CAS[78-84-2]) (75 μl; 0.82 mmol) in THF (7 mL) was stirred at rt. After 3 h, NaBH(OAc)₃ (290 mg; 1.4 mmol) was added and the mixture was stirred at rt overnight. The mixture was poured into ice water and EtOAc was added. The organic layer was separated, washed with brine, dried over $MgSO_4$, filtered and evaporated till dryness. The residue (280 mg) was purified by chromatography over silica gel (Stationary phase: irregular bare silica 12 g, Mobile phase: 0.1% $NH_4OH$, 97% DCM, 3% MeOH). The fractions containing product were collected and evaporated to dryness yielding 190 mg of product which was freeze-dried with ACN/water 20/80 to give 137 mg (51%) of compound 36.

NMR (400 MHz, DMSO-d₆) δ ppm 8.31 (s, 1H) 7.68 (br s, 1H) 3.99-4.14 (m, 2H) 3.55-3.99 (m, 4H) 2.37-2.49 (m, 4H) 2.24-2.32 (m, 1H) 2.12 (br s, 1H) 2.02 (d, J=7.6 Hz, 2H) 1.63-1.84 (in, 2H) 1.49 (br s, 1H) 0.85 (d, J=6.6 Hz, 6H)

The compounds in the Table below were prepared using an analogous method as described for the preparation of compound 36 starting from the respective starting materials.

| COMPOUND NUMBER | Structure |
|---|---|
| Compound 45 (from intermediate 8) | 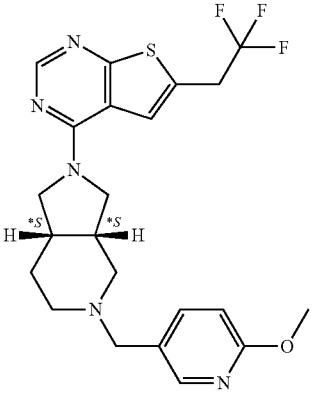 [SMILES: COc1ccc(CN2CC[C@@H]3CN(c4ncnc5sc(CC(F)(F)F)cc45)C[C@@H]3C2)cn1] |
| Compound 71B (from intermediate 8) | 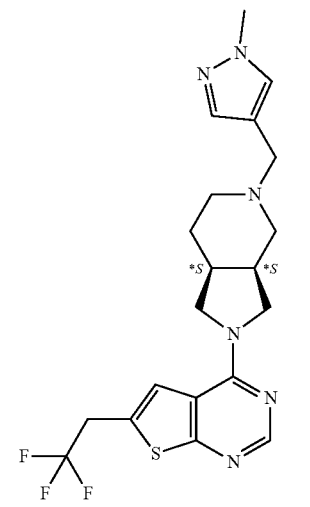 [SMILES: Cn1cc(CN2CC[C@@H]3CN(c4ncnc5sc(CC(F)(F)F)cc45)C[C@@H]3C2)cn1] |
| Compound 67 (from intermediate 8) | 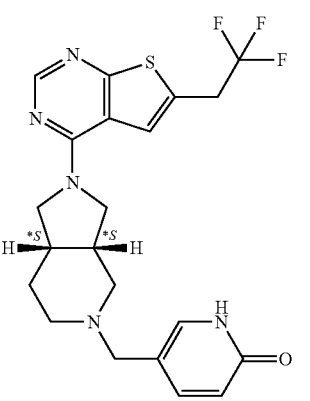 [SMILES: O=c1ccc(CN2CC[C@@H]3CN(c4ncnc5sc(CC(F)(F)F)cc45)C[C@@H]3C2)c[nH]1] |
-continued
| COMPOUND NUMBER | Structure |
|---|---|
| Compound 69 (from intermediate 9) (melting point 109° C. Kofler) | 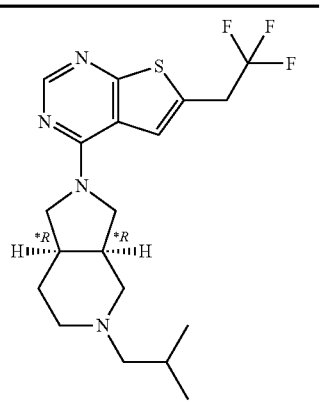 |
| Compound 37 (from intermediate 8) | 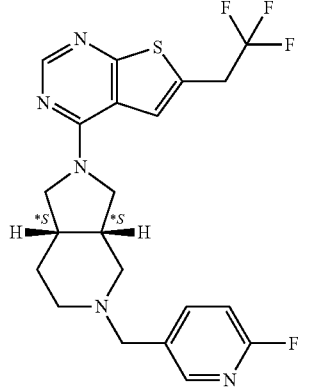 [SMILES: Fc1ccc(CN2CC[C@@H]3CN(c4ncnc5sc(CC(F)(F)F)cc45)C[C@@H]3C2)cn1] |
| Compound 38 (from intermediate 8) | 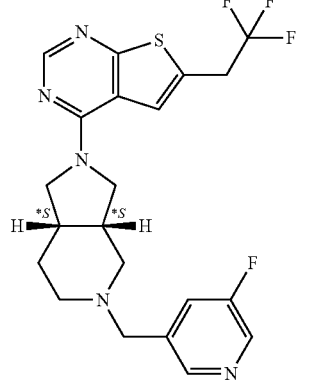 |
| Compound 39 (from intermediate 8) | 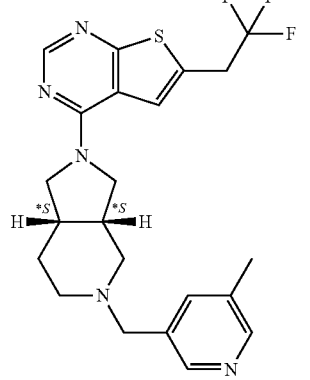 |

| COMPOUND NUMBER | Structure |
|---|---|
| Compound 40 (from intermediate 8) | 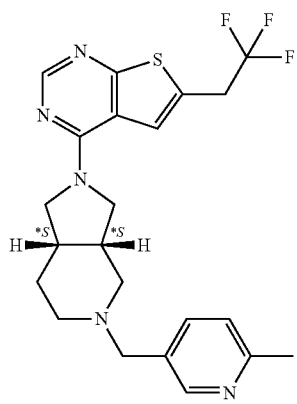 [SMILES: Cc1ccc(CN2CC[C@@H]3CN(c4ncnc5sc(CC(F)(F)F)cc45)C[C@@H]3C2)cn1] |
| Compound 41 (from intermediate 8) | 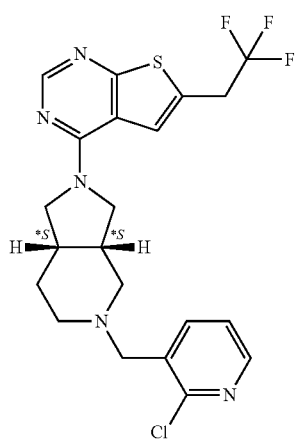 [SMILES: FC(F)(F)Cc1cc2c(N3C[C@H]4CCN(Cc5cccnc5Cl)C[C@H]4C3)ncnc2s1] |
| Compound 42 (from intermediate 8) | 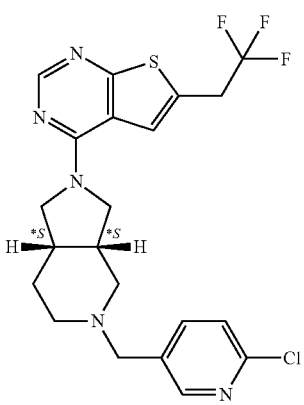 [SMILES: FC(F)(F)Cc1cc2c(N3C[C@H]4CCN(Cc5ccc(Cl)nc5)C[C@H]4C3)ncnc2s1] |
| COMPOUND NUMBER | Structure |
|---|---|
| Compound 43 (from intermediate 8) | 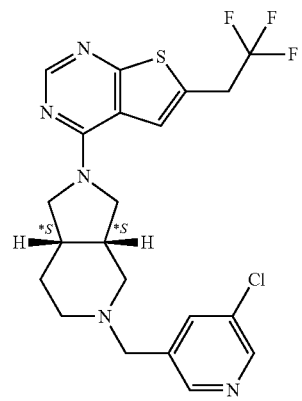 [SMILES: FC(F)(F)Cc1cc2c(N3C[C@H]4CCN(Cc5cncc(Cl)c5)C[C@H]4C3)ncnc2s1] |
| Compound 44 (from intermediate 8) | 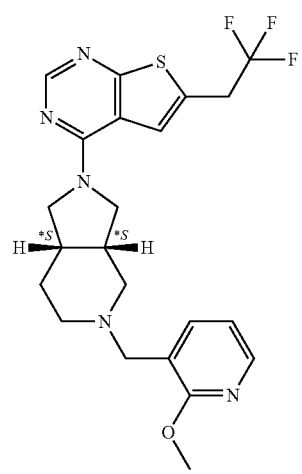 [SMILES: COc1ncccc1CN1CC[C@@H]2CN(c3ncnc4sc(CC(F)(F)F)cc34)C[C@@H]2C1] |
| Compound 46 (from intermediate 8) | 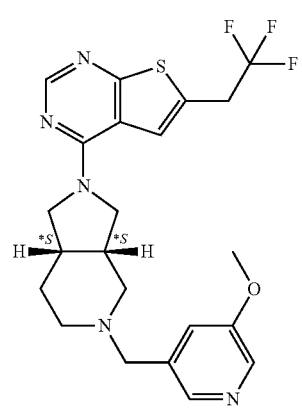 [SMILES: COc1cncc(CN2CC[C@@H]3CN(c4ncnc5sc(CC(F)(F)F)cc45)C[C@@H]3C2)c1] |

| COMPOUND NUMBER | Structure |
| --- | --- |
| Compound 47 (from intermediate 8) | 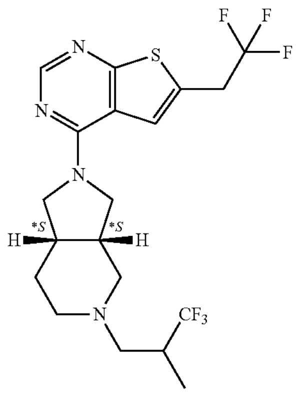 [SMILES: CC(CN1CC[C@@H]2CN(c3ncnc4sc(CC(F)(F)F)cc34)C[C@@H]2C1)C(F)(F)F] |
| Compound 48 (from intermediate 8) | 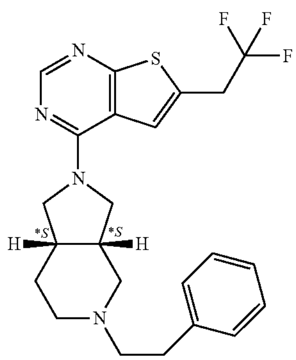 [SMILES: FC(F)(F)Cc1cc2c(N3C[C@H]4CCN(CCc5ccccc5)C[C@H]4C3)ncnc2s1] |
| Compound 49 (from intermediate 8) | 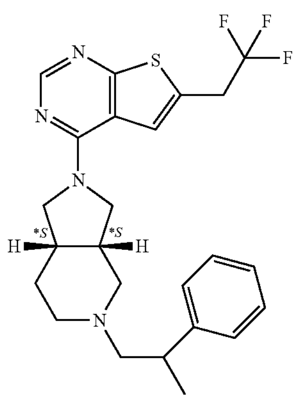 [SMILES: CC(CN1CC[C@@H]2CN(c3ncnc4sc(CC(F)(F)F)cc34)C[C@@H]2C1)c1ccccc1] |
| Compound 50 (from intermediate 8) | 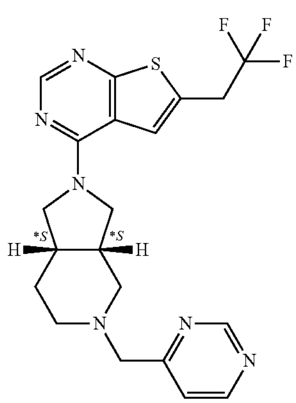 [SMILES: FC(F)(F)Cc1cc2c(N3C[C@H]4CCN(Cc5ccncn5)C[C@H]4C3)ncnc2s1] |
| Compound 51 (from intermediate 8) | |
| Compound 52 (from intermediate 8) | |
| Compound 53 (from intermediate 8) | |
| Compound 54 (from intermediate 8) | |

| COMPOUND NUMBER | Structure |
| --- | --- |
| Compound 55 (from intermediate 8) | (structure) |
| Compound 56 (from intermediate 8) | (structure) |
| Compound 57 (from intermediate 8) | (structure) |
| Compound 58 (from intermediate 8) | (structure) |
| Compound 59 (from intermediate 8) | (structure) |
| Compound 60 (from intermediate 8) | (structure) |
| Compound 61 (from intermediate 8) | (structure) |

| COMPOUND NUMBER | Structure |
|---|---|
| Compound 62 (from intermediate 8) | 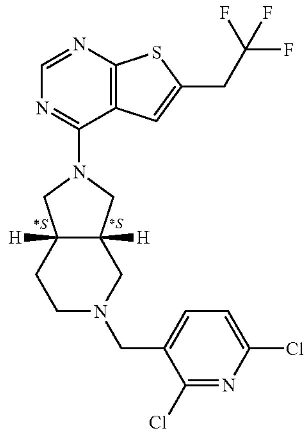 [SMILES: FC(F)(F)Cc1cc2c(N3C[C@H]4CCN(Cc5ccc(Cl)nc5Cl)C[C@H]4C3)ncnc2s1] |
| Compound 63 (from intermediate 8) | 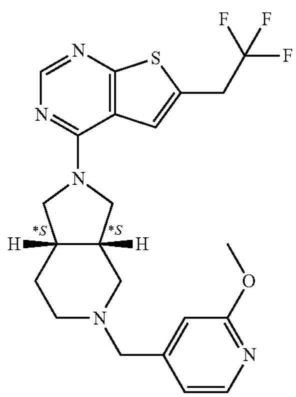 [SMILES: COc1cc(CN2CC[C@@H]3CN(c4ncnc5sc(CC(F)(F)F)cc45)C[C@@H]3C2)ccn1] |
| Compound 64 (from intermediate 8) | 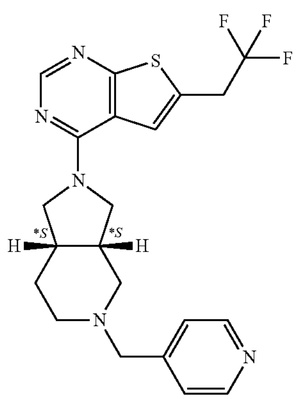 [SMILES: FC(F)(F)Cc1cc2c(N3C[C@H]4CCN(Cc5ccncc5)C[C@H]4C3)ncnc2s1] |
| Compound 65 (from intermediate 8) | 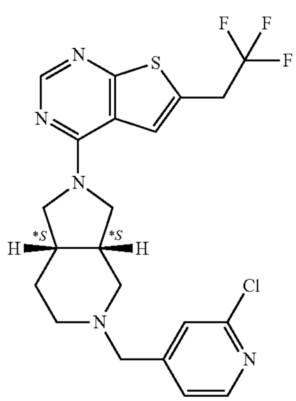 [SMILES: FC(F)(F)Cc1cc2c(N3C[C@H]4CCN(Cc5ccnc(Cl)c5)C[C@H]4C3)ncnc2s1] |

| COMPOUND NUMBER | Structure |
|---|---|
| Compound 66 (from intermediate 8) | 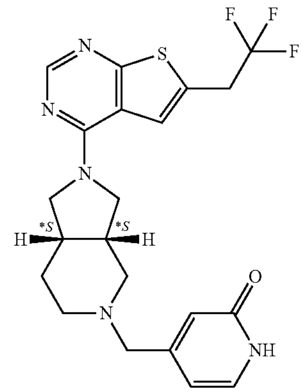 [SMILES: O=c1cc(CN2CC[C@@H]3CN(c4ncnc5sc(CC(F)(F)F)cc45)C[C@@H]3C2)cc[nH]1] |
| Compound 68 (from intermediate 8) | 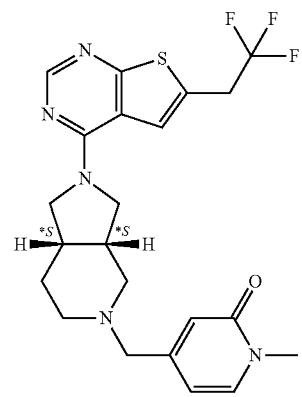 [SMILES: Cn1ccc(CN2CC[C@@H]3CN(c4ncnc5sc(CC(F)(F)F)cc45)C[C@@H]3C2)cc1=O] |

Example B7

Preparation of Compound 70

Under $N_2$ flow, a solution of intermediate 8 (107 mg; 0.3 mmol) and tetrahydropyran-4-carbaldehyde (CAS [50675-18-8]) (39 μL; 0.37 mmol) in THF (3 mL) was stirred at rt. After 3 h, NaBH(OAc)$_3$ (130 mg: 0.6 mmol) was added and the mixture was stirred at rt overnight. The mixture was poured into ice water and EtOAc was added. The organic layer was separated, washed with brine, dried over MgSO$_4$, filtered and evaporated till dryness. The compound (82 mg) was taken up Et$_{20}$, the precipitate was filtered and dried to give 32 mg of compound 70 (M.P: 160° C./Kofler)$^1$H NMR (500 MHz, DMSO-$d_6$) δ ppm 8.29 (s, 1H) 7.63 (s, 1H) 3.99 (q, J=11.0 Hz, 2H) 3.63-3.92 (m, 6H) 3.22-3.37 (m, 2H) 2.51-2.59 (m, 2H) 2.29-2.47 (m, 4H) 2.08-2.24 (m, 2H) 1.42-1.84 (m, 5H) 1.16 (br d, J=12.3 Hz, 2H)

Example B8

Preparation of Compound 71

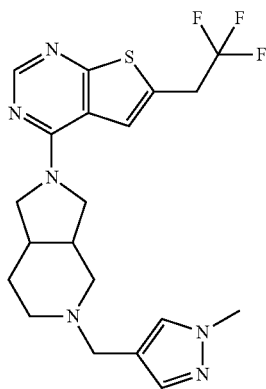 [SMILES: Cn1cc(CN2CCC3CN(c4ncnc5sc(CC(F)(F)F)cc45)CC3C2)cn1]

and Compound 71A

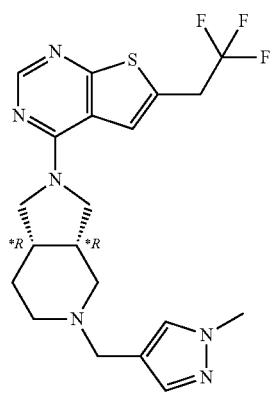 [SMILES: Cn1cc(CN2CC[C@@H]3CN(c4ncnc5sc(CC(F)(F)F)cc45)C[C@@H]3C2)cn1]

and Compound 71B

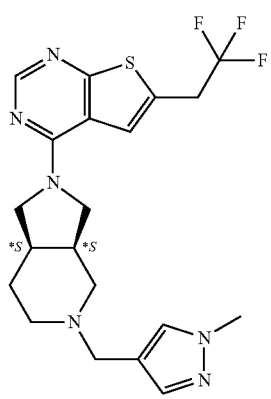 [SMILES: Cn1cc(CN2CC[C@H]3CN(c4ncnc5sc(CC(F)(F)F)cc45)C[C@H]3C2)cn1]

Under $N_2$ flow, NaBH(OAc)$_3$ (2.4 g; 11 mmol)$_3$ was added to a solution of intermediate 11 (840 mg; 2.2 mmol), 1-methyl-TH-pyrazole-4-carbaldehyde (CAS [25016-11-9]) (786 mg; 7.1 mmol) and Et$_3$N (1 mL; 6.7 mmol) in DCE (20 mL) was stirred at rt overnight. The mixture was poured into ice water with a saturated solution of NaHCO$_3$ and DCM was added. The organic layer was separated, washed with brine, dried over MgSO$_4$, filtered and evaporated till dryness. The residue (1.2 g) was purified by chromatography over silica gel (Stationary phase: irregular bare silica 80 g, Mobile phase gradient: 100% petroleum ether, 0% EtOAc to 0% petroleum ether, 100% EtOAc then 100% EtOAc, 0% MeOH to 80% EtOAc, 20% MeOH). The fractions containing product were collected and evaporated to dryness giving 500 mg of compound 71 which was submitted to SFC on chiral phase (Stationary phase 10 μm. 250*30 mm, Mobile phase: 55% CO$_2$, 45% MeOH(0.10% iPrNH$_2$)). The fractions containing products were collected and evaporated to dryness. The first eluted product was freeze dried with ACN/water 20/80 yielding 240 mg (24%) of compound 71A. The second eluted compound was freeze-dried with ACN/water 20/80 yielding 200 mg (21%) of compound 71B. The compound 71 was freeze dried with ACN/water 20/80 yielding 20 mg (2%) of compound 71.

Example B9

Preparation of Compound 70B (Conversion)

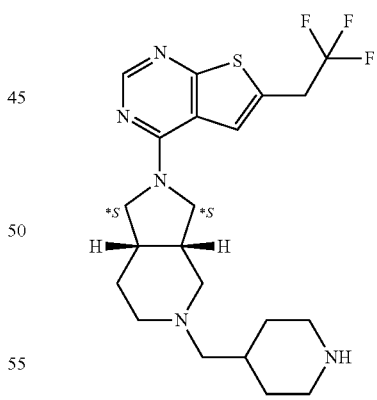

At 0° C., a 4N solution of HCl in dioxane (0.4 mL, 1.4 mmol) was added dropwise to a solution of Compound 20 (67 mg; 0.1 mmol) in MeOH (2 mL). The mixture was stirred at rt overnight. The mixture was poured into ice water, basified with a solution of NaOH 3N and DCM was added. The organic layer was separated, dried over MgSO$_4$, filtered and evaporated till dryness to give 45 mg of compound 70B.

Preparation of Compound 70C (Conversion)

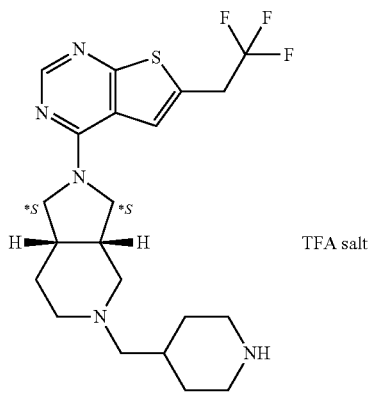 [SMILES: FC(F)(F)Cc1cc2c(N3C[C@H]4CCN(CC5CCNCC5)C[C@H]4C3)ncnc2s1 ; "TFA salt"]

TFA salt

To a solution of Compound 20 (1.90 g, 3.53 mmol) in 20 ml of DCM was added 5 ml of TFA. After stirring at room temperature for 0.5 h, the mixture was concentrated to yield Compound 70C (2.00 g, 100% yield) as yellow oil which was used in the next step without further purification.

Preparation of Compound 91

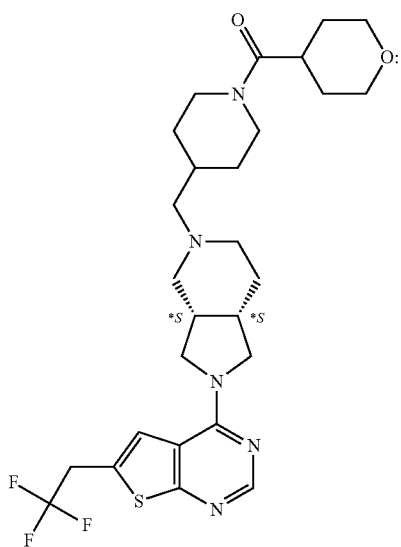

To a solution of tetrahydro-2H-pyran-4-carboxylic acid (44.0 mg, 0.335 mmol) in DCM (10 mL) was added HOBt (68.0 mg, 0.502 mmol), EDCI (96.0 mg, 0.502 mmol) and TEA (0.28 ml, 2 mmol). After stirring at room temperature, Compound 70C (300 mg, 0.335 mmol) was added and the mixture was stirred at room temperature for 2 h. The mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 91 (43.0 mg, 23.6% yield) as a white solid.

$^1$H NMR CD$_3$OD (400 MHz): δ 8.30 (s, 1H), 7.65 (s, 1H), 4.56-4.52 (m, 1H), 4.11-4.07 (m, 2H), 3.98-3.96 (m, 3H), 3.94-3.86 (m, 3H), 3.82-3.80 (m, 2H), 3.55-3.49 (m, 2H), 3.16-3.09 (m, 1H), 3.00-2.94 (m, 1H), 2.69-2.63 (m, 4H), 2.51-2.50 (m, 2H), 2.29-2.23 (m, 3H), 1.94-1.73 (m, 6H), 1.66-1.60 (m, 3H), 1.15-1.04 (m, 2H).

Preparation of Compound 92

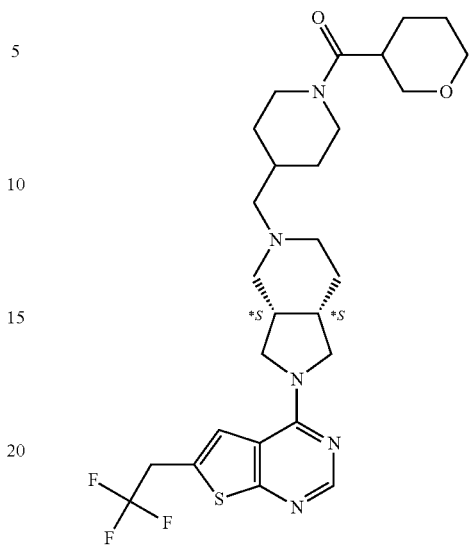

To a solution of tetrahydro-2H-pyran-3-carboxylic acid (44.0 mg, 0.335 mmol) in DCM (10 mL) was added HOBt (68.0 mg, 0.502 mmol), EDCI (96.0 mg, 0.502 mmol) and TEA (0.28 ml, 2 mmol). After stirring at room temperature, Compound 70C (300 mg, 0.335 mmol) was added and the mixture was stirred at room temperature for 2 h. The mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 92 (45 mg, 24.3% yield) as a white solid.

$^1$H NMR CD$_3$OD (400 MHz) δ 8.30 (s, 1H), 7.65 (s, 1H), 4.52-4.49 (m, 1H), 4.08-4.00 (m, 5H), 3.93-3.89 (m, 2H), 3.86-3.80 (m, 2H), 3.53-3.39 (m, 2H), 3.16-3.10 (m, 1H), 2.97-2.92 (m, 1H), 2.66-2.60 (m, 4H), 2.51-2.48 (m, 2H), 2.29-2.22 (m, 3H), 1.94-1.76 (m, 5H), 1.82-1.69 (m, 4H), 1.15-1.03 (m, 2H).

Preparation of Compound 93

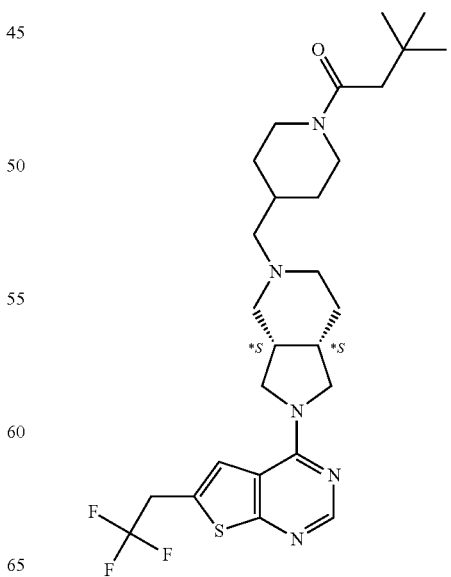

To a solution of Compound 70C (300 mg, 0.335 mmol) in DCM (10 mL) was added 3,3-dimethylbutanoyl chloride (45.0 mg, 0.335 mmol) and TEA (0.28 ml, 2 mmol). After stirring at room temperature for 2 h, the mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 93 (57 mg, 31.6% yield) as a white solid.

$^1$H NMR CD$_3$OD (400 MHz): δ 8.30 (s, 1H), 7.65 (s, 1H), 4.61-4.58 (m, 1H), 4.10-3.80 (m, 7H), 3.16-3.08 (m, 1H), 2.67-2.23 (m, 11H), 1.91-1.83 (m, 4H), 1.69-1.64 (m, 1H), 1.19-1.06 (m, 11H).

Preparation of Compound 94

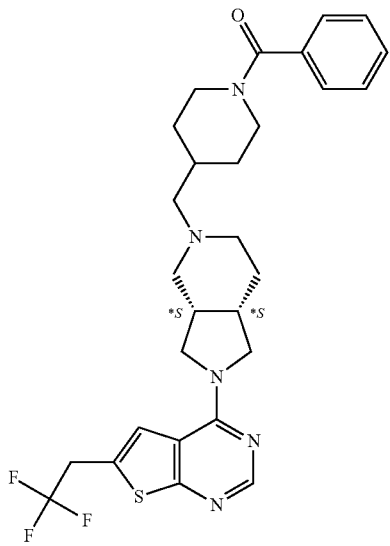 [SMILES: O=C(c1ccccc1)N1CCC(CN2CC[C@@H]3CN(c4ncnc5sc(CC(F)(F)F)cc45)C[C@@H]3C2)CC1]

To a solution of Compound 70C (300 mg, 0.335 mmol) in DCM (10 mL) was added benzoyl chloride (47.0 mg, 0.335 mmol) and TEA (0.28 ml, 2 mmol). After stirring at room temperature for 2 h, the mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 94 (70.0 mg, 38.8% yield) as a white solid.

$^1$H NMR CD$_3$OD (400 MHz): δ 8.29 (s, 1H), 7.64 (s, 1H), 7.49-7.47 (m, 3H), 7.42-7.40 (m, 2H), 4.66-4.63 (m, 1H), 4.00-3.95 (m, 1H), 3.92-3.84 (m, 3H), 3.80-3.73 (m, 3H), 3.15-3.09 (m, 1H), 2.92-2.86 (m, 1H), 2.61-2.48 (m, 5H), 2.30-2.26 (m, 3H), 1.94-1.89 (m, 2H), 1.86-1.77 (m, 2H), 1.69-1.64 (m, 1H), 1.25-1.14 (m, 2H).

Preparation of Compound 95

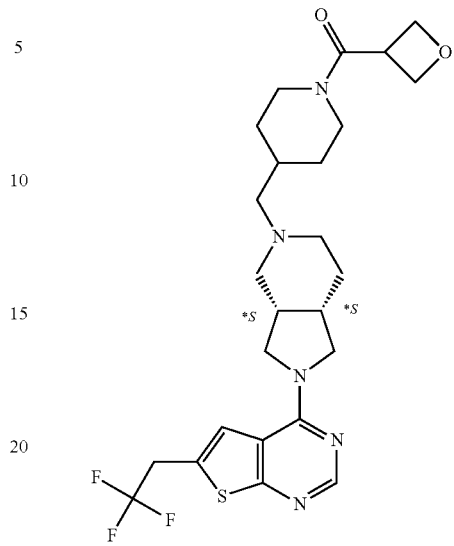

To a solution of oxetane-3-carboxylic acid (35.0 mg, 0.335 mmol) in DCM (10 mL) was added HOBt (68.0 mg, 0.502 mmol), EDCI (96 mg, 0.502 mmol) and TEA (0.28 ml, 2.00 mmol). After stirring at room temperature, Compound 70C (300 mg, 0.335 mmol) was added and the mixture was stirred at room temperature for 2 h. The mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 95 (41 mg, 23.4% yield) as a white solid.

$^1$H NMR CD$_3$OD (400 MHz): δ 8.29 (s, 1H), 7.64 (s, 1H), 4.86-4.80 (m, 4H), 4.54-4.51 (m, 1H), 4.23-4.15 (m, 1H), 4.05-3.98 (m, 1H), 3.94-3.86 (m, 3H), 3.79-3.75 (m, 2H), 3.49-3.45 (m, 1H), 3.06-2.99 (m, 1H), 2.74-2.46 (m, 6H), 2.28-2.21 (m, 3H), 1.87-1.84 (m, 4H), 1.66-1.63 (m, 1H), 1.13-1.02 (m, 2H).

Preparation of Compound 96

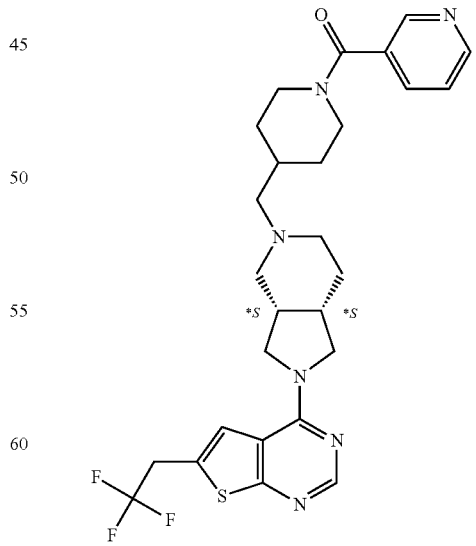

To a solution of nicotinic acid (35.0 mg, 0.335 mmol) in DCM (10 mL) was added HOBt (68 mg, 0.502 mmol), EDCI (96 mg, 0.502 mmol) and TEA (0.28 ml, 2 mmol).

After stirring at room temperature, Compound 70C (300 mg, 0.335 mmol) was added and the mixture was stirred at room temperature for 2 h. The mixture was concentrated to give a residue which was purified by prep-HPLC (Waters 2767/Qda, Column: Waters Xbridge19*150 mm 10 um, Mobile Phase A: H₂O (0.1% NH₄OH), B: ACN) to yield Compound 96 (65.0 mg, 35.1% yield) as a white solid.

¹H NMR CD₃OD (400 MHz) δ 8.64-8.60 (m, 2H), 8.26 (s, 1H), 7.88 (d, J=7.6 Hz, 1H), 7.61 (s, 1H), 7.53 (dd, J=5.2 Hz, 7.6 Hz, 1H), 4.65-4.55 (m, 1H), 4.02-3.77 (m, 6H), 3.68-3.62 (m, 1H), 3.21-3.14 (m, 1H), 3.00-2.86 (m, 1H), 2.68-2.47 (m, 5H), 2.26-2.25 (m, 3H), 1.92-1.82 (m, 4H), 1.66-1.62 (m, 1H), 1.29-1.11 (m, 2H).

Example B10

Preparation of Compound 19

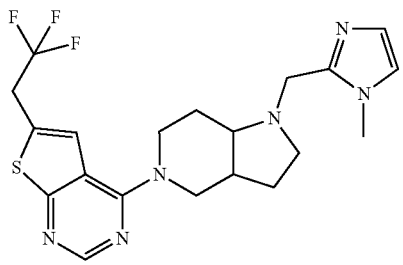

Under nitrogen flow, 1-methyl-2-imidazolecarboxaldehyde (137.4 mg, 1.25 mmol) was added to a solution of intermediate 3 (250 mg, 0.61 mmol) in dry DCM (10 mL). The mixture was stirred at room temperature for 5 h. Then NaBH(OAc)₃ (260 mg; 1.23 mmol) was added portionwise and the mixture was stirred at rt for 72 h. The reaction mixture was poured into ice water and the organic layer was separated, the aqueous layer was extracted with DCM twice. The organic layers were combined, washed with brine then dried over MgSO₄, evaporated. The residue was purified by chromatography over silica gel (Stationary phase: irregular SiOH 15-40 μm 24 g, Mobile phase: Gradient from 0.5% NH₄OH, 97% DCM, 3% MeOH to 0.5% NH₄OH, 95% DCM, 5% WOW The fractions containing product were collected and evaporated to dryness yielding 75 mg (yield 21%) of product which was freeze-dried with Acetonitrile/water 20/80 to give 45 mg of compound 19.

The compound and intermediate in the Table below were prepared using an analogous method as described for the preparation of compound 19, starting from the respective starting materials.

| COMPOUND NUMBER | Structure |
|---|---|
| Intermediate 53 (from intermediate 3) | 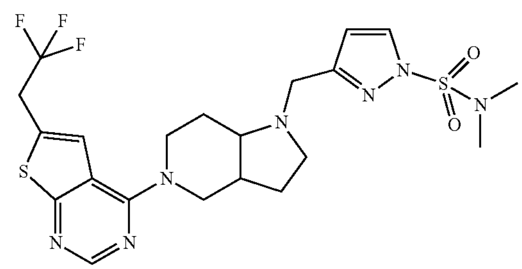 [SMILES: CN(C)S(=O)(=O)n1ccc(CN2CCC3CN(c4ncnc5sc(CC(F)(F)F)cc45)CCC32)n1] |
| Compound 21 (from intermediate 36) | 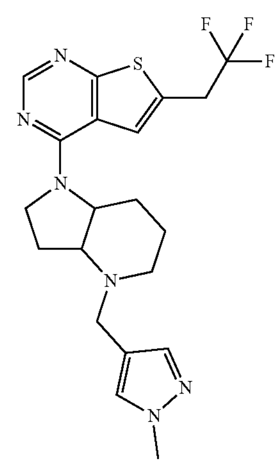 [SMILES: Cn1cc(CN2CCCC3C2CCN3c2ncnc3sc(CC(F)(F)F)cc23)cn1] |

Preparation of Compound 22

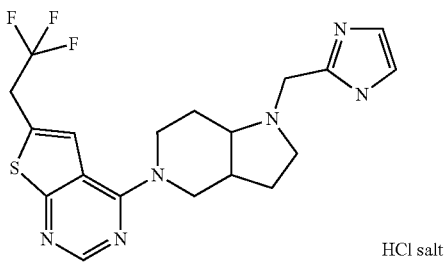 [SMILES: FC(F)(F)Cc1cc2c(N3CCC4C(CCN4Cc4ncc[nH]4)C3)ncnc2s1]

HCl salt

At 5° C., a solution of HCl 4N in dioxane (1.2 mL; 4.7 mmol) was added dropwise to a solution of intermediate 41 (250 mg; 0.5 mmol) in ACN (15 mL). The reaction mixture was stirred at rt for 15 h. The solution was evaporated to dryness and taken up with Et$_2$O. The residue (200 mg) was taken up with Et$_{20}$ and pentane, the precipitate was filtered and dried to give 182 mg (66%) of compound 22 (HCl salt). M.P: 140° C. (Kofler).

Example B11

Preparation of Compound 23

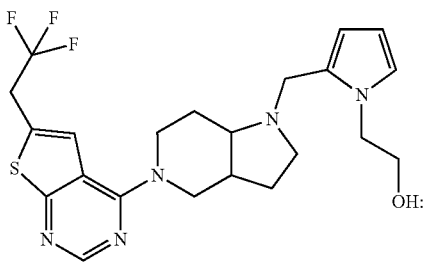

INTERMEDIATE 39 (250 mg, 0.5 mmol), a 3N solution of NaOH (0.8 mL; 2.5 mmol) in MeOH (10 mL) were heated at 60° C. for 45 min. The mixture was cooled to rt, poured into water, extracted twice with EtOAc. The organic layer was dried over MgSO$_4$, filtered and evaporated to dryness. The residue (200 mg) was purified by chromatography over silica gel (Stationary phase: irregular bare silica 40 g, Mobile phase: 0.1% NH$_4$OH, 97% DCM, 3% MeOH). The fractions containing product were collected and evaporated to dryness yielding 100 mg of a pure product and another fraction 90 mg of an impure product. The pure product was freeze-dried with Acetonitrile/water 20/80 to give 75 mg of the compound 23.

The compound in the Table below was prepared using an analogous method as described for the preparation of compound 23 starting from the respective starting materials.

Example B12

Preparation of Compound 25

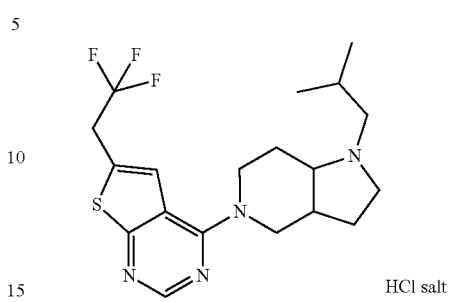

HCl salt

Under N$_2$ flow, a solution of intermediate 3 (200 mg; 0.6 mmol) and isobutyraldehyde (CAS[78-84-2]) (107 µL; 1.2 mmol) and acetic acid (67 µL; 1.2 mmol) in THF (5 mL) was stirred at rt. After 4 h, NaBH(OAc)$_3$ (372 mg; 1.7 mmol) was added and the mixture was stirred at rt overnight. The mixture was poured into ice water and EtOAc was added. The organic layer was separated, washed with brine, dried over MgSO$_4$, filtered and evaporated till dryness. The residue (235 mg) was purified by chromatography over silica gel (Stationary phase: irregular bare silica 24 g, Mobile phase: 0.1% NH$_4$OH, 97% DCM, 3% MeOH). The fractions containing product were collected and evaporated to dryness. The compound was dissolved in 2 mL of ACN and HCl 4N (1 eq, 62 µL, 0.25 mmol) was added dropwise at 10° C. Et$_2$O was added and, after 15 h, a precipitate was filtered and dried giving 55 mg of compound 25. M.P: 140° C. (Kofler) as a HCl salt.

Example B13

Preparation of Compound 26

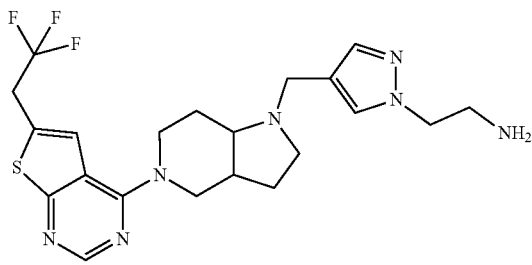 [SMILES: NCCn1cc(CN2CCC3CN(c4ncnc5sc(CC(F)(F)F)cc45)CCC32)cn1]

| INTERMEDIATE COMPOUND | Structure |
|---|---|
| Compound 24 (from intermediate 40) | 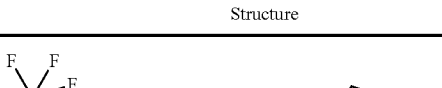 |

Hydrazine hydrate (CAS [302-01-2]) (118 μL; 3 mmol) was added to a solution of intermediate 38 (180 mg: 0.3 mmol) in EtOH (5 mL). The solution was heated at 70° C. for 1 h 30. The reaction mixture was cooled to rt, poured into ice water and DCM was added. The organic layer was separated, washed with brine, dried over MgSO₄, filtered and evaporated till dryness. The residue (120 mg) was purified by chromatography over silica gel (Stationary phase: irregular bare silica 12 g, Mobile phase gradient: 0.1% NH₄OH, 95% DCM, 5% MeOH to 1% NH₄OH, 90% DCM, 10% MeOH). The fractions containing product were collected and evaporated to dryness. The residue (65 mg) was purified by reverse phase (Stationary phase: 10 μm 30*150 mm, Mobile phase gradient from 60% NH₄CO₃ (0.2%), 40% ACN to 0% NH₄CO₃ (0.2%), 100% ACN). The fractions containing product were collected and evaporated to dryness yielding 32 mg of product. The product was freeze dried with Acetonitrile/water 20/80 to give 26 mg (19%) of compound 26.

Example B14

Preparation of Compound 27

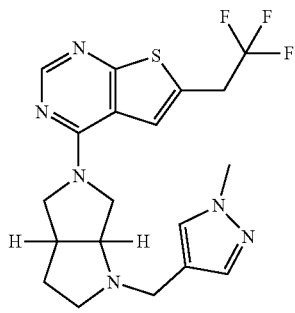 [SMILES: Cn1cc(CN2CCC3CN(c4ncnc5sc(CC(F)(F)F)cc45)CC32)cn1]

Compound 27A

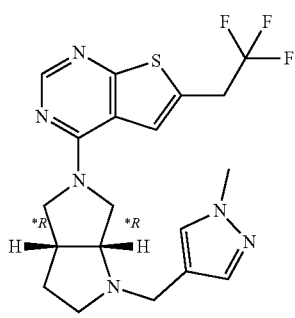 [SMILES: Cn1cc(CN2CC[C@@H]3CN(c4ncnc5sc(CC(F)(F)F)cc45)C[C@@H]32)cn1]

Compound 27B

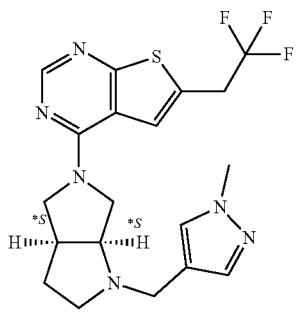 [SMILES: Cn1cc(CN2CC[C@H]3CN(c4ncnc5sc(CC(F)(F)F)cc45)C[C@H]32)cn1]

Compound 27C

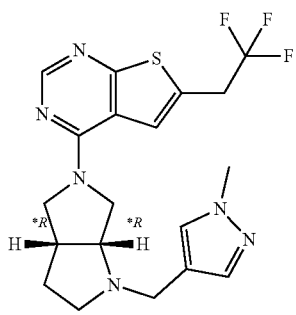

HCl salt and Compound 27D

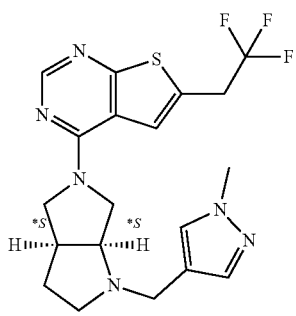

HCl salt

Under N₂ flow, a solution of intermediate 29 (500 mg; 1.4 mmol), 1-methyl-1H-pyrazole-4-carbaldehyde (CAS [25016-11-9]) (181 mg; 1.6 mmol) and Et₃N (0.4 mL; 2.7 mmol) in DCM (12 mL) was stirred at rt. After 4 h, NaBH(OAc)₃ (581 mg; 2.8 mmol) was added and the mixture was stirred at rt overnight. The mixture was poured into ice water and DCM was added. The organic layer was separated, washed with brine, dried over MgSO₄, filtered and evaporated till dryness. The residue (500 mg) was purified by chromatography over silica gel (Stationary phase: irregular bare silica 12 g, Mobile phase gradient: 0.1% NH₄OH, 97% DCM, 3% MeOH to 0.1% NH₄OH, 95% DCM, 5% MeOH). The product containing fractions were collected and evaporated to dryness to give 290 mg of compound 27.

The compound 27 was submitted to chiral SFC (Stationary phase: CHIRACEL® OJ-H1 5 μm 250*20 mm, Mobile phase: 85% CO₂, 15% MeOH(0.30% iPrNH₂)). The fractions containing products were collected, evaporated to dryness yielding 114 mg (20%) of compound 27A and 128 mg (22%) of compound 27B. Compound 27A was dissolved in ACN and converted into hydrochloric salt by treatment with HCl. The precipitate was filtered and dried providing 80 mg of compound 27C.

Compound 27B was dissolved in ACN and converted into hydrochloric salt by treatment with HCl. The precipitate was filtered and dried providing 75 mg of compound 27D.

The compounds in the Table below were prepared using an analogous method as described for the preparation of compounds 27, 27A and 27B starting from the indicated starting materials

| COMPOUND NUMBER | Structure |
|---|---|
| Compound 28A and Compound 28B (from intermediate 29) | 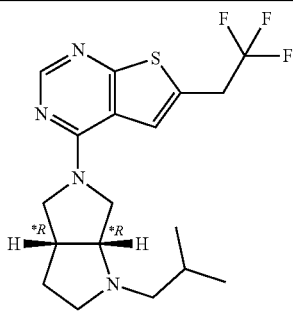<br>Compound 28A<br><br>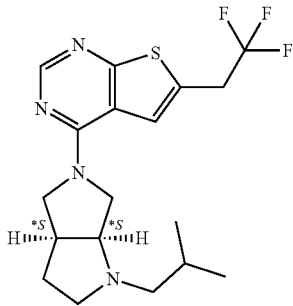<br>Compound 28B |

Example B15

Preparation of Compound 29

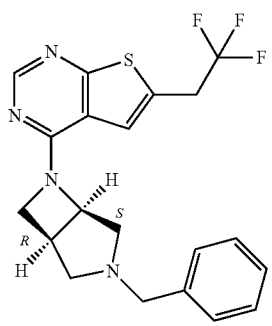

Benzyl bromide (CAS: [100-39-0]) (954, 0.8 mmol) and then potassium carbonate (205 mg, 1.5 mmol) were successively added to a solution of intermediate 31 (235 mg, 0.7 mmol) in ACN (12 mL) and the mixture was stirred at rt overnight. The mixture was poured into ice water and EtOAc was added. The organic layer was separated, washed with brine, dried over MgSO$_4$, filtered and evaporated till dryness. The residue (330 mg) was purified by chromatography over silica gel (Stationary phase: irregular bare silica 10 g, Mobile phase gradient: 0% NH$_4$OH, 100% DCM, 0% MeOH to 0.1% NH$_4$OH, 97% DCM, 3% MeOH) The fractions containing product were collected and evaporated to dryness. The compound was crystallized from Et$_2$O and pentane, the precipitate was filtered and dried to give 139 mg of compound 29 (46% yield). M.P 134° C. (Kofler).

The compounds in the Table below were prepared using an analogous method as described for the preparation of compound 29, starting from the respective starting materials

| COMPOUND NUMBER | Structure |
|---|---|
| Compound 30 (from intermediate 32) | 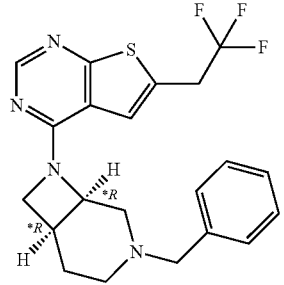<br>HCl salt |
| Compound 31 (from intermediate 33) | 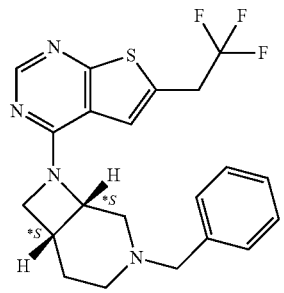<br>HCl salt |
| Compound 32 (from intermediate 35 | 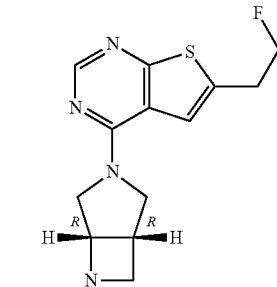 |

| COMPOUND NUMBER | Structure |
|---|---|
| Compound 33 (from intermediate 34 | 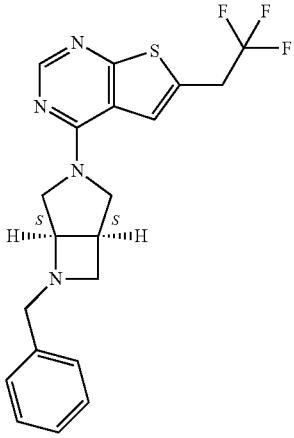 |

Example B16

Preparation of Compound 34:

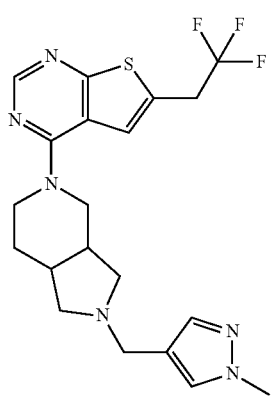 [SMILES: Cn1cc(CN2CC3CCN(c4ncnc5sc(CC(F)(F)F)cc45)CC3C2)cn1]

Intermediate 37 (270 mg, 1 mmol), 4-chloro-6-(2,2,2-trifluoroethyl)thieno[2,3-d]pyrimidine (CAS[1628317-85-0]) (220 mg, 0.9 mmol) (prepared as described in Journal of Medicinal Chemistry (2016), 59(3), 892-913); DIEA (0.5 mL, 2.6 mmol) in iPrOH (5 mL) were heated at 90° C. overnight. The mixture was evaporated till dryness. The residue (700 mg) was purified by reverse phase (Stationary phase: irregular 5 μm 15025 mm, mobile phase gradient: 70% NH$_4$HCO$_3$ (0.05%), 30% ACN to 40% NH$_4$HCO$_3$ (0.05%), 60% ACN). The fractions containing product were collected and evaporated to dryness yielding, 95 mg (yield 25%) compound 34.

The compounds in the Table below were prepared using an analogous method as described for the preparation of compound 34, starting from the respective starting materials.

| COMPOUND NUMBER | Structure |
|---|---|
| Compound 35A and Compound 35B (from intermediate 44) | 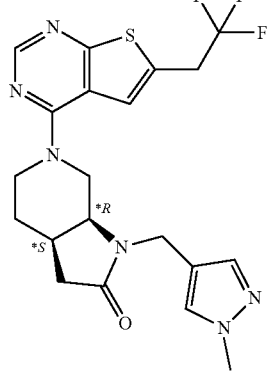<br>COMPOUND 35A<br>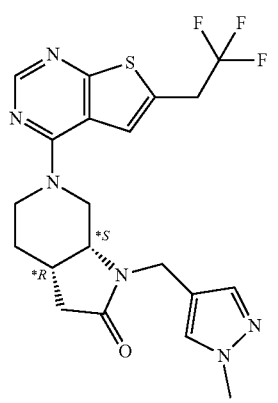<br>COMPOUND 35B |

Example B17

Preparation of Compound 72

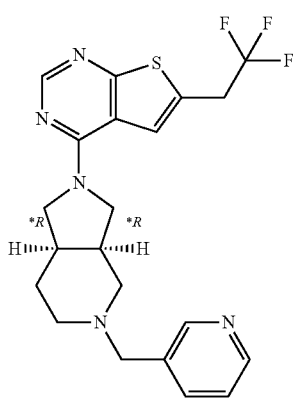 [SMILES: FC(F)(F)Cc1cc2c(N3C[C@H]4CN(Cc5cccnc5)CC[C@H]4C3)ncnc2s1]

Under N$_2$ flow, a solution of intermediate 9 (100 mg; 0.3 mmol) and pyridine-3-carboxaldehyde (CAS [500-22-1]) (34 μL; 0.4 mmol) in DCM (2.5 mL) and MeOH (2.5 mL) was stirred at rt. After 3 h, NaBH(OAc)$_3$ (124 mg; 0.6 mmol) was added and the mixture was stirred at rt for 24 h. The mixture was poured into ice water and EtOAc was added. The organic layer was separated, washed with brine, dried over MgSO$_4$, filtered and evaporated till dryness. The residue (145 mg) was purified by chromatography over silica gel (Stationary phase: irregular bare silica 12 g, Mobile phase gradient: 0.1% NH₄OH, 97% DCM, 3% MeOH to 0.1% NH₄OH, 95% DCM, 5% MeOH). The fractions containing product were collected and evaporated to dryness. The residue (71 mg) was purified by chromatography over silica gel (Stationary phase: irregular bare silica 12 g, Mobile phase gradient: 0.1% NH₄OH, 97% DCM, 3% MeOH to 0.1% NH₄OH, 95% DCM, 5% MeOH). The fractions containing product were collected and evaporated to dryness. The compound was freeze-dried with ACN/water (20/80) yielding 30 mg of compound 72.

Example B18

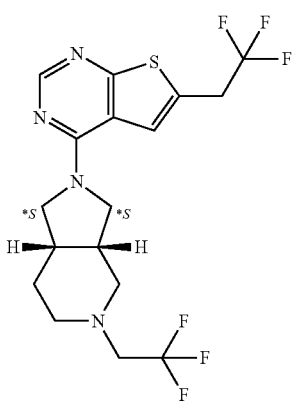 [SMILES: FC(F)(F)Cc1cc2c(N3C[C@H]4CCN(CC(F)(F)F)C[C@H]4C3)ncnc2s1]

Preparation of Compound 73

A solution of intermediate 8 (105 mg; 0.31 mmol), 2,2,2-trifluoroethyltrifluoro-methanesulfonate (CAS [6226-25-1]) (55 μL; 0.4 mmol) and DBU (92 μL; 0.6 mmol) in DMSO (3 mL) was stirred at rt overnight. The reaction mixture was poured into ice water and EtOAc was added. The organic layer was separated, washed with water several times then brine, dried over MgSO₄, filtered and evaporated till dryness. The residue (169 mg) was purified by chromatography over silica gel (Stationary phase: irregular bare silica 12 g, Mobile phase gradient from: 0% NH₄OH, 100% DCM, 0% MeOH to 0.1% NH₄OH, 95% DCM, 5% MeOH). The fractions containing product were collected and evaporated to dryness yielding 72 mg of compound which was freeze-dried with Acetonitrile/water (20/80) to give 43 mg (34%) of compound 73

Preparation of Compound 74

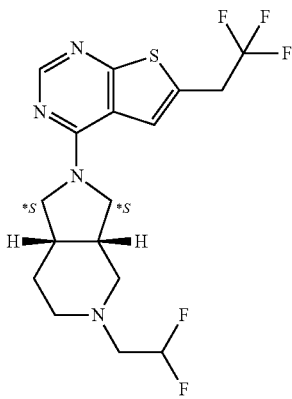 [SMILES: FC(F)CN1CC[C@@H]2CN(c3ncnc4sc(CC(F)(F)F)cc34)C[C@@H]2C1]

A solution of intermediate 8 (100 mg; 0.29 mmol), 2,2-difluoroethyltrifluoromethane-sulfonate (CAS [74427-22-8]) (47 μL; 0.4 mmol) and DIEA (103 μL; 0.6 mmol) in DMF (4 mL) was stirred at rt overnight. The reaction mixture was poured into ice water and EtOAc was added. The organic layer was separated, washed with water several times then brine, dried over MgSO₄, filtered and evaporated till dryness. The residue (139 mg) was purified by chromatography over silica gel (Stationary phase: irregular bare silica 12 g, Mobile phase gradient from: 0.1% NH₄OH, 98% DCM, 2% MeOH to 0.1% NH₄OH, 95% DCM, 5% MeOH). The fractions containing product were collected and evaporated to dryness yielding 83 mg of product which was freeze dried with Acetonitrile/water (20/80) to give 40 mg (34%) of compound 74.

Example B19

Preparation of Compound 75

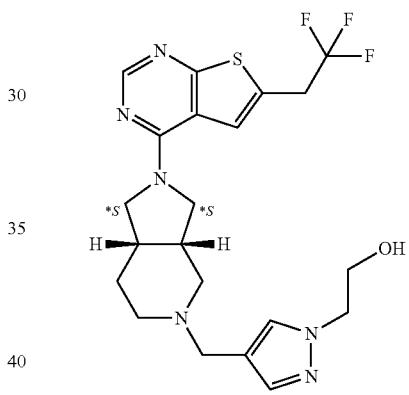

A solution of TBAF (1M in THF) (0.24 mL; 0.24 mmol) was added dropwise to a solution of intermediate 13 (71 mg; 0.1 mmol) in THF (2 mL). The reaction mixture was stirred at rt overnight. The mixture was poured into ice water, basified with a 10% of solution of K₂CO₃ and EtOAc was added. The organic layer was separated, washed with brine, dried over MgSO₄, filtered and evaporated till dryness to give a residue (67 mg) which was purified by chromatography over silica gel (Stationary phase: irregular bare silica 40 g, Mobile phase: 0.7% NH₄OH, 93% DCM, 7% MeOH). The fractions containing product were collected and evaporated to dryness. The residue was purified by reverse phase (Stationary phase: C18 10 μm 30*150 mm, Mobile phase: Gradient from 75% NH₄HCO₃ 0.2%, 25% ACN to 35% NH₃HCO₃ 0.2%, 65% ACN). The fractions containing product were collected and evaporated to dryness to give 11 mg of compound which was taken up with Et₂O and evaporated till dryness to give 10 mg of compound 75.

Example B20

Preparation of Compound 76

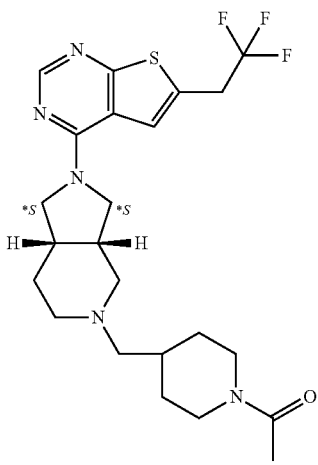 [SMILES: CC(=O)N1CCC(CN2CC[C@@H]3CN(c4ncnc5sc(CC(F)(F)F)cc45)C[C@@H]3C2)CC1]

At 5° C., acetyl chloride (CAS [75-36-5]) (25 µL; 0.3 mmol) was added to a solution of compound 70B (100 mg; 0.2 mmol) and DIEA (79 µL; 0.5 mmol) in DCM (5 mL). The reaction mixture was stirred at rt for 4 h. The reaction was poured into ice water, basified with a 10% aqueous solution of $K_2CO_3$ and DCM was added. The organic layer was separated, dried over $MgSO_4$, filtered and evaporated till dryness. The residue (194 mg) was purified by chromatography over silica gel (Stationary phase: irregular bare silica 12 g, Mobile phase gradient from: 0.1% $NH_4OH$, 97% DCM, 3% MeOH to 0.1% $NH_4OH$, 95% DCM, 5% MeOH). The fractions containing product were collected and evaporated to dryness. The compound was freeze-dried with ACN/water (20/80) yielding 65 mg of compound 76.

Example B21

Preparation of Compound 77

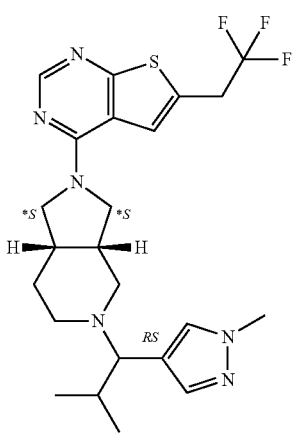

and Compound 77A

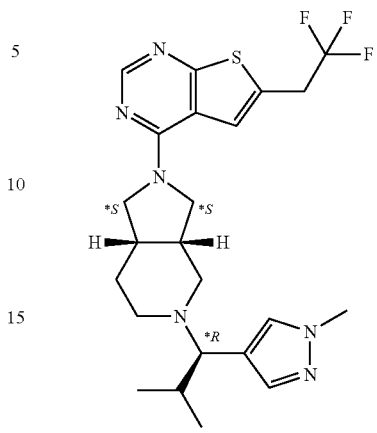

And Compound 77B

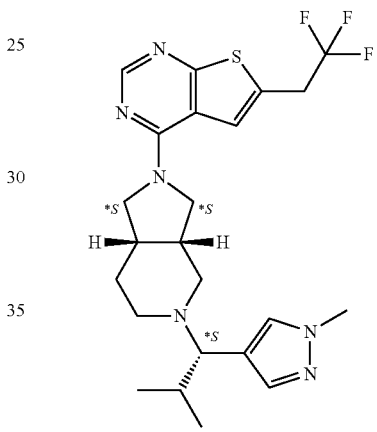

Under $N_2$ flow at rt, 1-methyl-1H-pyrazole-4-carbaldehyde (CAS [25016-11-9]) (98 mg; 0.9 mmol) and titanium (IV) ethoxide (CAS 13087-36-31) (0.3 mL; 1.2 mmol) were added to a solution of intermediate 8 (202 mg; 0.6 mmol) in THF (5 mL). The reaction mixture was stirred at rt for 20 h. The solution was cooled to 0° C. and an isopropylmagnesium chloride solution (2M in THF) (CAS [1068-55-9]) (1.5 mL; 3 mmol) was added dropwise. The reaction mixture was stirred at 0° C. for 30 min and allowed to slowly rise to rt for 24 h. The solution was poured into ice water, EtOAc was added and filtered through a pad of Celite®. The organic layer was separated, dried over $MgSO_4$, filtered and evaporated till dryness. The residue (226 mg) was purified by chromatography over silica gel (Stationary phase: irregular bare silica 12 g, Mobile phase: 0.1% $NH_4OH$, 97% DCM, 3% MeOH). The fractions containing product were collected and evaporated to dryness to afford 25 mg (9%) of compound 77 which was submitted to chiral SFC (Stationary phase: CHIRACEL OJ-H1 5 µm 250*20 mm, Mobile phase: 88% $CO_2$, 12% MeOH(0.30% iPrNH$_2$)). The fractions containing the products were collected, evaporated to dryness to afford 2 fractions that were respectively taken up with $Et_2O$ and evaporated till dryness yielding 9 mg of compound 77A AND 6 mg of compound 77B.

The compounds in the Table below were prepared using an analogous method as described for the preparation of compound 77, 77A and 77B starting from the indicated starting materials

| COMPOUND NUMBER | Structure |
|---|---|
| Compound 78 (from intermediate 9), Compound 78A and Compound 78B | 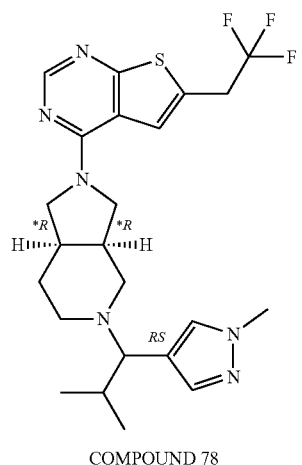 [SMILES: CC(C)C(c1cnn(C)c1)N1CC[C@H]2CN(c3ncnc4sc(CC(F)(F)F)cc34)C[C@H]2C1]<br>COMPOUND 78 |
| | 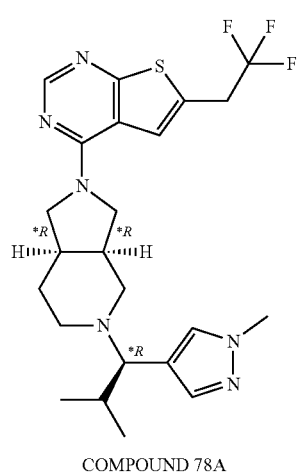 [SMILES: CC(C)[C@H](c1cnn(C)c1)N1CC[C@H]2CN(c3ncnc4sc(CC(F)(F)F)cc34)C[C@H]2C1]<br>COMPOUND 78A |
| | 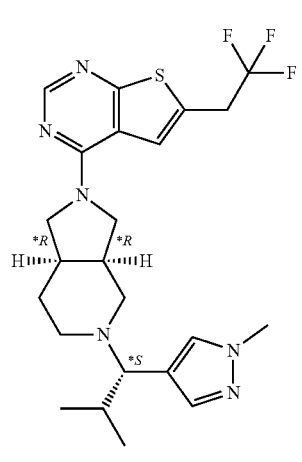<br>COMPOUND 78B |

Example B22

Preparation of Compound 79

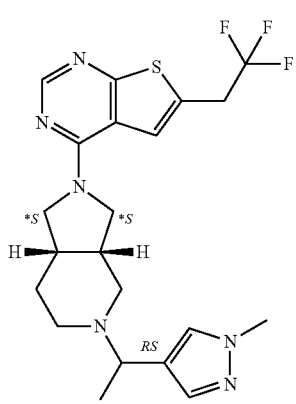 [SMILES: CC(c1cnn(C)c1)N1CC[C@@H]2CN(c3ncnc4sc(CC(F)(F)F)cc34)C[C@@H]2C1]

and Compound 79A

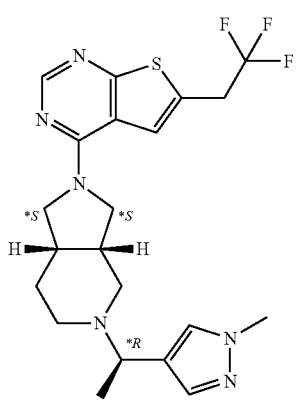 [SMILES: C[C@H](c1cnn(C)c1)N1CC[C@@H]2CN(c3ncnc4sc(CC(F)(F)F)cc34)C[C@@H]2C1]

And Compound 79B

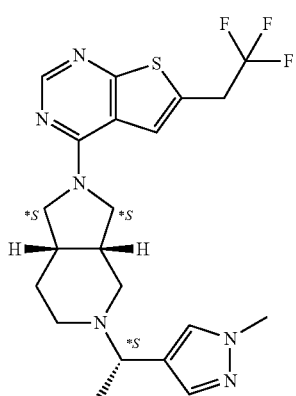

The compounds were prepared using an analogous method as described for the preparation of compound 77, 77A and 77B starting from the intermediate 8 and methylmagnesium bromide in solution 3M in $Et_{2O}$.

Example B23

Preparation of Compound 80

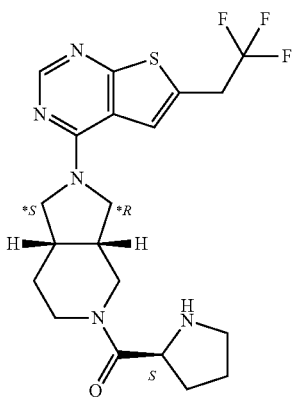

At 5° C., a solution of HCl 4N in dioxane (0.6 mL; 2.1 mmol) was added dropwise to a solution of intermediate 16 (114 mg; 0.2 mmol) in DCM (4 mL). The reaction mixture was stirred at rt for 15 h. The solution was poured into ice water, basified with a solution of NaOH 3N and DCM was added. The organic layer was separated, dried over $MgSO_4$, filtered and evaporated till dryness. The residue was taken up $Et_2O$, the precipitate was filtered and dried to give 43 mg (46%) of compound 80.

The compounds in the Table below were prepared using an analogous method as described for the preparation of compound 80 starting from the indicated starting materials

| COMPOUND NUMBER | Structure |
|---|---|
| Compound 81 (from intermediate 17 | |
| Compound 82 (from intermediate 18 | 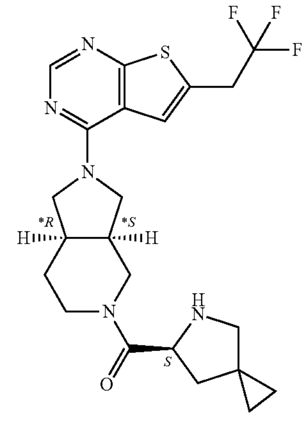 |
| Compound 83 (from intermediate 19 | 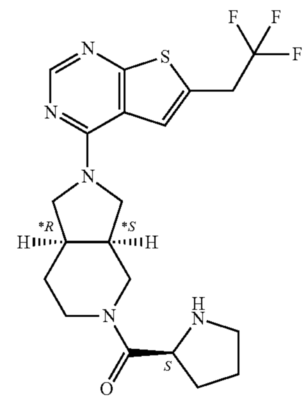 |

Example B24

Preparation of Compound 86

To a solution of intermediate 47 (150 mg, 0.44 mmol) in MeOH (5 mL) was added 1,6-dioxaspiro[2.5]octane (100 mg, 0.88 mmol) and $Et_3N$ (266 mg, 2.63 mmol). After stirring at 65° C. overnight, the mixture was concentrated, diluted with EA and $H_2O$, separated and extracted twice with EA. The combined extracts ware concentrated in vacuo and purified by prep-HPLC (Waters 2767/Qda, Column: SunFire 19*150 mm 10 um, Mobile Phase A: H₂O (0.1% TFA), B: ACN) to give compound 86 (64.69 mg, TFA salt) as colorless oil.

¹H NMR CD₃OD (400 MHz): δ 8.41 (s, 1H), 7.71 (s, 1H), 4.10 (s, 2H), 3.87-3.99 (m, 4H), 3.61-3.84 (m, 6H), 3.18 (s, 2H), 2.97 (s, 2H), 2.83 (s, 1H), 2.32-2.42 (m, 1H), 2.06-2.18 (m, 1H), 2.06-2.18 (m, 1H), 1.64-1.82 (m, 5H).

Preparation of Compound 71B and 87

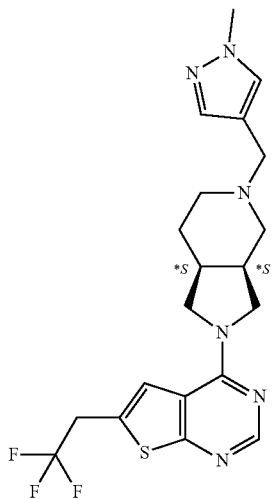

Compound 71B (free base)
Compound 87 (HCl salt)

To a solution of Intermediate 47 (1.20 g, 1.76 mmol) in DCM (20 mL) was added intermediate 48 (220 mg, 2.00 mmol) and NaBH(OAc)₃ (746 mg, 3.52 mmol). After stirring at room temperature overnight, the mixture was concentrated to give a residue which was purified by a column chromatography on silica gel (eluent: DCM:MeOH=20:1, v/v) to yield compound 71B (550 mg, 72% yield, free base) as yellow oil.

To a solution of compound 71B (550 mg, 1.26 mmol) in EA (20 mL) was added HCl/dioxane (4 M, 1 mL, 4 mmol). After the completed of addition, the reaction mixture was stirred at room temperature overnight, filtered and dried to yield compound 87 (480 mg, HCl salt) as yellow solid.

¹H NMR Co 87 CDCl₃ (400 MHz): δ 8.41 (s, 1H), 7.39 (s, 1H), 7.37 (s, 1H), 7.27 (s, 1H), 3.76-3.88 (m, 6H), 3.71-3.75 (m, 1H), 3.59-3.67 (m, 2H), 3.42 (s, 2H), 2.61-2.30 (m, 7H), 1.81-1.84 (m, 1H).

Preparation of Compound 88

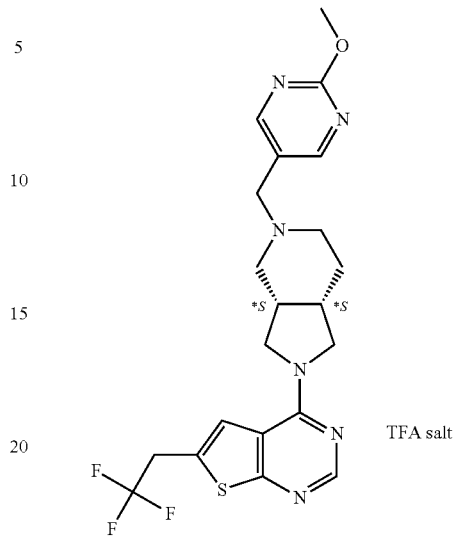

TFA salt

To a solution of Intermediate 47 (200 mg, 0.292 mmol) in DCM (8 mL) was added 2 methoxypyrimidine-5-carbaldehyde (48.5 mg, 0.350 mmol) and NaBH(OAc)₃ (155 mg, 0.73 mmol). After stirring at room temperature overnight, the mixture was concentrated to give a residue, which was purified by prep-HPLC (Waters 2767/Qda, Column: SunFire 19*250 mm 10 um, Mobile Phase A: 0.1% TFA/H₂O, B: ACN) to yield Compound 88 (54 mg, TFA salt) as yellow oil.

¹H NMR CD₃OD (400 MHz): δ 8.71 (s, 2H), 8.47 (s, 1H), 7.73 (s, 1H), 4.42-4.34 (m, 2H), 4.11-4.01 (m, 6H), 3.97-3.89 (m, 3H), 3.51-3.31 (m, 3H), 3.00-2.79 (m, 3H), 2.27-2.14 (m, 2H).

Preparation of Compound 89

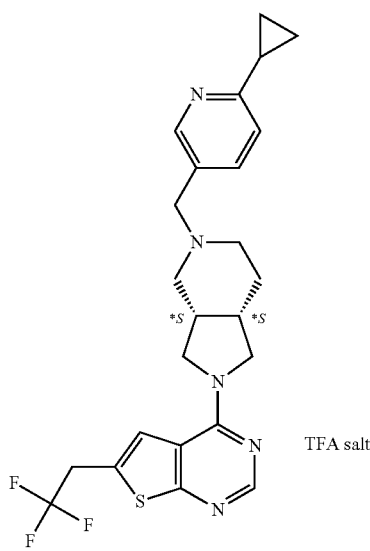 [SMILES: FC(F)(F)Cc1cc2c(N3C[C@H]4CCN(Cc5ccc(C6CC6)nc5)C[C@H]4C3)ncnc2s1 ; "TFA salt"]

TFA salt

To a solution of Intermediate 49 (300 mg, 2.04 mmol) in EtOH (5 ml) was added Intermediate 47 (698 mg, 2.04 mmol) and Pt₂O (30 mg, 10%). After stirring at 60° C. overnight under Hz, the mixture was filtered, and the filtrate was concentrated in vacuo to give a residue which was purified by prep-HPLC (Waters 2767/Qda, Column: SunFire 19*250 mm 10 um, Mobile Phase A: 0.1% TFA/H$_2$O, B: ACN) to yield Compound 89 (59.16 mg, TFA salt) as yellow oil.

$^1$H NMR CD$_3$OD (400 MHz): δ 8.55 (s, 1H) 8.42 (s, 1H), 7.98 (d, J=8.4 Hz, 1H), 7.70 (s, 1H), 7.44 (d, J=8.4 Hz, 1H), 4.90 (m, 1H), 4.42-4.33 (m, 2H), 4.10-4.04 (m, 2H), 4.01-3.87 (m, 4H), 3.45-3.42 (m, 2H), 2.87-2.76 (m, 3H), 2.13-2.19 (m, 2H), 2.19-2.17 (m, 1H), 1.20-1.17 (m, 2H), 1.08-1.07 (m, 2H).

Preparation of Compound 90

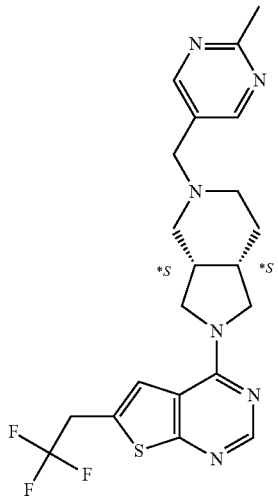 [SMILES: Cc1ncc(CN2CC[C@@H]3CN(c4ncnc5sc(CC(F)(F)F)cc45)C[C@@H]3C2)cn1]

To a solution of Intermediate 47 (200 mg, 0.292 mmol) in DCM (8 mL) was added 2 methylpyrimidine-5-carbaldehyde (42.8 mg, 0.350 mmol) and NaBH(OAc)$_3$ (155 mg, 0.73 mmol). After stirring at room temperature overnight, The mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 90 (35 mg, 26.7% yield) as a light yellow solid.

$^1$H NMR CD$_3$OD (400 MHz): δ 8.66 (s, 2H), 8.27 (s, 1H), 7.62 (s, 1H), 4.10-3.71 (m, 6H), 3.56 (s, 2H), 2.68 (s, 3H), 2.62-2.33 (m, 6H), 1.89-1.61 (m, 2H)

Preparation of Compound 97

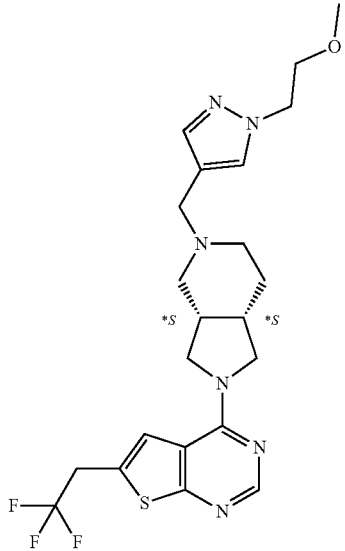 [SMILES: COCCn1cc(CN2CC[C@@H]3CN(c4ncnc5sc(CC(F)(F)F)cc45)C[C@@H]3C2)cn1]

To a solution of Intermediate 47 (300 mg, 0.44 mmol) in dichloromethane (5 mL) was added intermediate 50 (80.0 mg, 0.530 mmol) and NaBH(OAc)$_3$ (186 mg, 0.880 mmol). After stirring at room temperature overnight, the mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 97 (53.0 mg, 24.6% yield) as yellow oil.

$^1$H NMR CDCl$_3$ (400 MHz): δ 8.42 (s, 1H), 7.42 (s, 1H), 7.38 (s, 2H), 4.26 (t, J=5.2 Hz, 2H), 3.91-3.83 (m, 3H), 3.75-3.73 (m, 3H), 3.64 (q, J=10.4 Hz, 2H), 3.43 (s, 2H), 3.33 (s, 3H), 2.54-2.49 (m, 4H), 2.37-2.32 (m, 2H), 1.86-1.80 (m, 1H), 1.70-1.63 (s, 1H).

Preparation of Compound 98

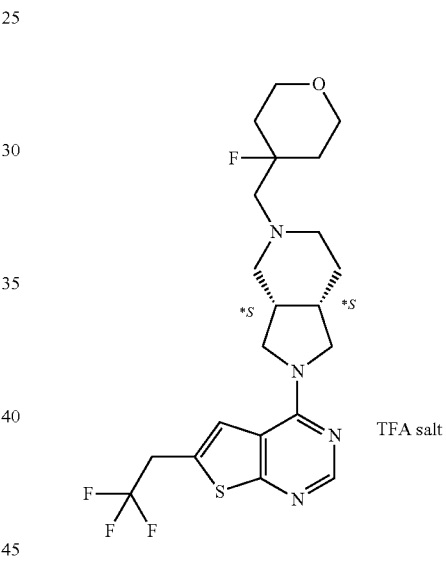

TFA salt

To a mixture of intermediate 52 (250 mg, 1.896 mmol) and intermediate 47 (642 mg, 1.00 mmol) in DCM (10 mL) was added NaBH(OAc)$_3$ (636 mg, 3.00 mmol). The mixture was stirred at room temperature for 18 h and evaporated. The residue was diluted in water (20 mL), extracted with DCM (30 mL*2). The combined organic layer was dried over Na$_2$SO$_4$, filtered and evaporated, The residue was purified by HPLC (Waters 2767/Qda, Column: SunFire 19*250 mm 10 um, Mobile Phase A: 0.1% TFA/H$_2$O, B: ACN) to yield Compound 98 (36 mg, TFA salt) as white solid.

$^1$HNMR CD$_3$OD (400 MHz): δ 8.47 (s, 1H), 7.76 (S, 1H), 3.84-4.13 (m, 8H), 3.61-3.75 (m, 3H), 3.49-3.54 (m, 5H), 2.84-2.97 (m, 2H), 2.3-2.34 (m, 1H), 1.80-2.10 (m, 5H).

Preparation of Compound 99

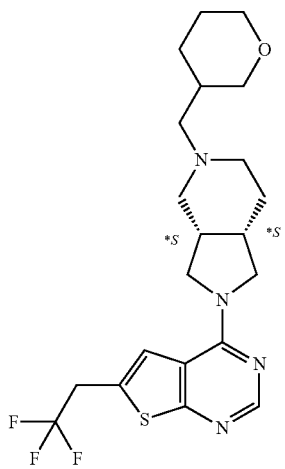 [SMILES: FC(F)(F)Cc1cc2c(N3C[C@H]4CCN(CC5CCCOC5)C[C@H]4C3)ncnc2s1]

To a solution of intermediate 47 (300 mg, 0.44 mmol) in DCM (5 mL) was added tetrahydro-2H-pyran-3-carbaldehyde (50 mg, 0.44 mmol) and NaBH(OAc)$_3$ (140 mg, 0.66 mmol). After stirring at room temperature overnight, the reaction mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 99 (38 mg, 20% yield) as a yellow solid.

1H NMR CD$_3$OD (400 MHz) δ 8.27 (s, 1H), 7.63 (s, 1H), 3.96-3.77 (m, 8H), 3.44-3.38 (m, 1H), 3.39-3.13 (m, 1H), 2.64-2.50 (m, 4H), 2.44-2.30 (m, 2H), 1.86-1.84 (m, 3H), 1.64-1.60 (m, 3H), 1.27-1.20 (m, 1H).

Preparation of Compound 100

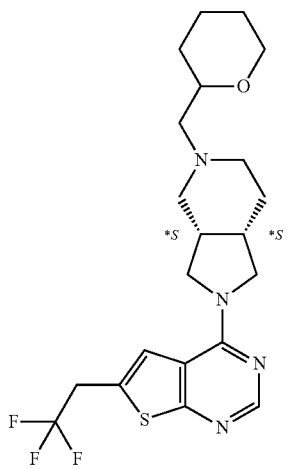 [SMILES: FC(F)(F)Cc1cc2c(N3C[C@H]4CCN(CC5CCCCO5)C[C@H]4C3)ncnc2s1]

To a solution of intermediate 47 (300 mg, 0.44 mmol) in DCM (5 mL) was added tetrahydro-2H-pyran-2-carbaldehyde (50 mg, 0.44 mmol) and NaBH(OAc)$_3$ (140 mg, 0.66 mmol). After stirring overnight at room temperature, the reaction mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 100 (63 mg, 32.6% yield) as a yellow solid.

1H NMR CDCl$_3$ (400 MHz) δ 8.42 (s, 1H), 7.38 (s, 1H), 4.00-3.97 (m, 1H), 3.89-3.82 (m, 2H), 3.78-3.73 (m, 1H), 3.66-3.59 (m, 2H), 3.48-3.39 (m, 2H), 2.58-2.48 (m, 5H), 2.41-2.36 (m, 2H), 2.30-2.26 (m, 1H), 1.89-1.83 (m, 2H), 1.74-1.65 (m, 2H), 1.62-1.48 (m, 4H), 1.31-1.22 (m, 1H).

Preparation of Compound 101

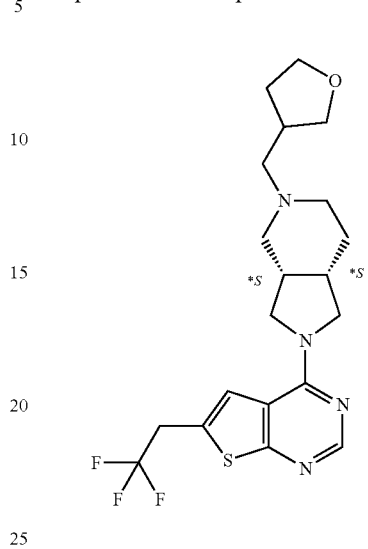

To a solution of intermediate 47 (300 mg, 0.44 mmol) in DCM (5 mL) was added tetrahydro-2H-pyran-2-carbaldehyde (44 mg, 0.44 mmol) and NaBH(OAc)$_3$ (140 mg, 0.66 mmol). After stirring at room temperature overnight, the reaction mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield Compound 101 (48 mg, 25.7% yield) as a yellow solid.

1H NMR (400 MHz, CD$_3$OD) δ 8.27 (s, 1H), 7.63 (s, 1H), 3.99-3.70 (m, 9H), 3.53-3.50 (m, 1H), 2.60-2.40 (m, 6H), 2.47-2.30 (m, 3H), 2.08-2.03 (m, 1H), 1.86-1.82 (m, 1H), 1.67-1.61 (m, 2H).

Preparation of Compound 102 (TFA Salt of Compound 36)

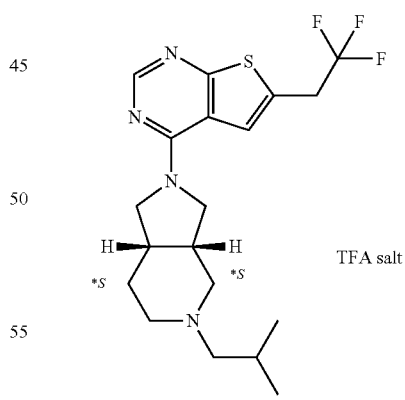

To a solution of intermediate 47 (300 mg, 0.44 mmol) in DCM (5 mL) was added isobutyraldehyde (50 mg, 0.53 mmol) and NaBH(OAc)$_3$ (186 mg, 0.88 mmol). After stirring at room temperature overnight, the reaction mixture was concentrated to give a residue which was purified by prep-HPLC (Waters 2767/Qda, Column: SunFire 19*250 mm 10 um, Mobile Phase A: 0.1% TFA/H$_2$O, B: ACN) to yield Compound 102 (80 mg, TFA salt) as yellow solid.

1H NMR CD$_3$OD (400 MHz) δ 8.27 (s, 1H), 7.63 (s, 1H), 3.99-3.70 (m, 9H), 3.53-3.50 (m, 1H), 2.60-2.40 (m, 6H), 2.47-2.30 (m, 3H), 2.08-2.03 (m, 1H), 1.86-1.82 (m, 1H), 1.67-1.61 (m, 2H).

Example B25

Preparation of Compound 20

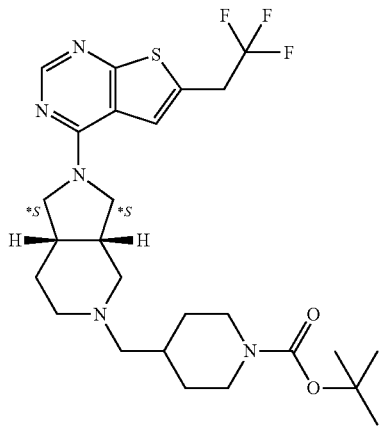 [SMILES: CC(C)(C)OC(=O)N1CCC(CN2CC[C@@H]3CN(c4ncnc5sc(CC(F)(F)F)cc45)C[C@@H]3C2)CC1]

Under N$_2$ flow, a solution of intermediate 8 (329 mg; 1 mmol) and 1-boc-4-piperidinecarboxaldehyde (CAS [123855-51-6]) (246 mg; 1.1 mmol) in THF (7 mL) was stirred at rt. After 4 h, NaBH(OAc)$_3$ (407 mg; 1.9 mmol) was added and the mixture was stirred at rt overnight. The mixture was poured into ice water, basified with a solution of NaOH 3N and EtOAc was added. The organic layer was separated, washed with brine, dried over MgSO$_4$, filtered and evaporated till dryness. The residue (662 mg) was purified by chromatography over silica gel (Stationary phase: irregular silica 12 g, Mobile phase: 0.1% NH$_4$OH, 97% DCM, 3% MeOH). The fractions containing product were collected and evaporated to dryness yielding 386 mg of Compound 20.

Alternative Preparation of Compound 20

To a solution of Intermediate 47 (3.00 g, 4.39 mmol), tert-butyl 4-formylpiperidine-1-carboxylate (1.10 g, 5.30 mmol) in 20 ml of DCM, NaBH(OAc)$_3$ (1.80 g, 8.80 mmol) was added. After stirring at room temperature for 2 h, the mixture was concentrated and purified by chromatography on silica gel with PE/EtOAc=10/1 to 5/1 as gradient to yield Compound 20 (1.90 g, 79% yield) as a yellow solid.

Example B26

Preparation of Compound 103

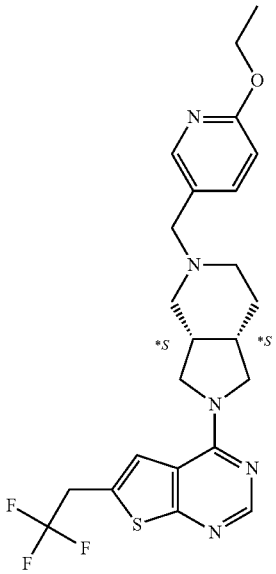 [SMILES: CCOc1ccc(CN2CC[C@@H]3CN(c4ncnc5sc(CC(F)(F)F)cc45)C[C@@H]3C2)cn1]

To a solution of 6-ethoxy-3-pyridinecarboxaldehyde (195 mg, 1.29 mmol) in DCM (10 mL) was added intermediate 47 (340 mg, 0.99 mmol) and titanium tetraisopropanolate (2 drops). After stirring at room temperature for 2 h, NaBH(OAc)$_3$ was added to the mixture at 0° C. and stirred overnight. The mixture was concentrated, diluted with EA and H$_2$O, and the aqueous layer was extracted twice with EA. The combined extracts were concentrated in vacuo and purified by prep-HPLC (Waters 2767/Qda, Column: Waters Xbridge19*150 mm 10 um, Mobile Phase A: H$_2$O (0.1% NH$_4$OH), B: ACN) to yield compound 103 (69.9 mg, 11.3% yield) as a white solid.

$^1$H NMR CD$_3$OD (400 MHz): δ 8.26 (s, 1H), 7.62 (s, 1H), 7.55-7.60 (m, 2H), 6.51-6.66 (m, 1H), 3.98-4.00 (dd, J=6.8 Hz, 14.2 Hz, 3H), 3.71-3.90 (m, 3H), 3.82-3.91 (m, 3H), 3.77 (m, 1H), 3.32 (s, 2H), 2.48-2.64 (m, 5H), 2.28-2.40 (m, 1H), 1.79-1.90 (m, 1H), 1.60-1.72 (m, 1H), 1.29-1.33 (m, 3H).

Preparation of Compound 104

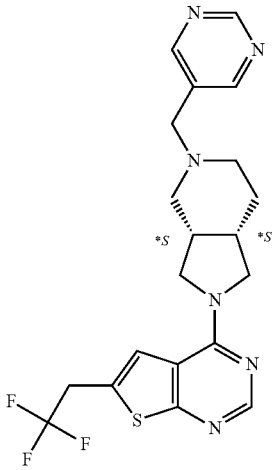 [SMILES: FC(F)(F)Cc1cc2c(N3C[C@H]4CCN(Cc5cncnc5)C[C@H]4C3)ncnc2s1]

To a solution of Intermediate 47 (200 mg, 0.292 mmol) in DCM (8 mL) was added pyrimidine-5-carbaldehyde (37.9 mg, 0.350 mmol) and NaBH(OAc)$_3$ (155 mg, 0.73 mmol). After stirring at room temperature overnight, the mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield compound 104 (74 mg, 58.3% yield) as a light yellow solid.

$^1$H NMR CD$_3$OD (400 MHz): δ 9.06 (s, 1H), 8.78 (s, 2H), 8.27 (s, 1H), 7.62 (s, 1H), 3.95-3.78 (m, 6H), 3.60 (s, 2H), 2.63-2.35 (m, 6H), 1.83-1.65 (m, 2H)

Preparation of Compound 105

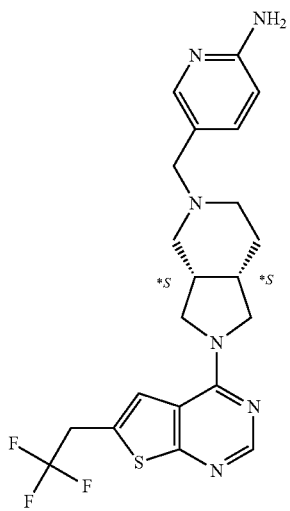 [SMILES: Nc1ccc(CN2CC[C@@H]3CN(c4ncnc5sc(CC(F)(F)F)cc45)C[C@@H]3C2)cn1]

To a mixture of intermediate 54 (140 mg, 0.25 mmol) in DCM (10 ml) was added CF$_3$COOH (285 mg, 2.50 mmol). The reaction mixture was stirred overnight, and the solvent was removed under reduced pressure. The residue was purified by prep-HPLC (Waters 2767/Qda, Column: Waters Xbridge19*150 mm 10 um, Mobile Phase A: H$_2$O (0.1% NH$_4$OH), B: ACN) to yield compound 105 (65.0 mg, 0.145 mmol, 29.0% yield) as a white solid.

$^1$H NMR CD$_3$OD (400 MHz): δ 8.27 (s, 1H), 7.81 (s, 1H), 7.62 (s, 1H), 7.46-7.48 (m, 1H), 6.58 (d, J=8.4 Hz, 1H), 3.77-3.96 (m, 6H), 3.39 (s, 2H), 2.36-2.56 (m, 6H), 1.81-1.85 (m, 1H), 1.65-1.68 (m, 1H)

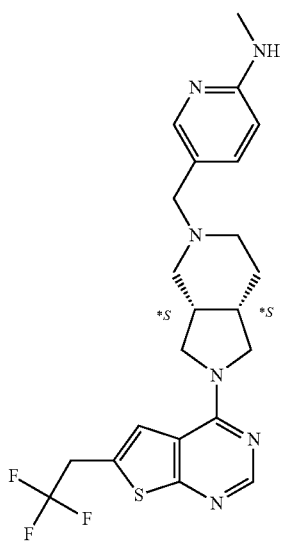 [SMILES: CNc1ccc(CN2CC[C@@H]3CN(c4ncnc5sc(CC(F)(F)F)cc45)C[C@@H]3C2)cn1]

Preparation of Compound 106

To a mixture of intermediate 47 (170 mg, 0.5 mmol) and 6-(methylamino)-nicotinaldehyde (102 mg, 0.75 mmol) in DCM (10 mL) was added titanium(IV) isopropoxide (284 mg, 1 mmol). The mixture was stirred at room temperature for 1 h, and then, NaBH(OAc)$_3$ (212 mg, 1 mmol) was added. The reaction mixture was stirred at room temperature for 4 h. The residue was diluted in water (20 mL), extracted with DCM (30 mL×2). The combined organic layer was dried over Na$_2$SO$_4$, filtered and evaporated. The residue was purified by Prep-HPLC (Waters 2767/Qda, Column: Waters Xbridge19*150 mm 10 um, Mobile Phase A: H$_2$O (0.1% NH$_4$OH), B: ACN) to yield compound 106 (52.3 mg, 0.11 mmol, 22.6% yield) as a white solid.

$^1$H NMR CD$_3$OD (400 MHz): δ 8.26 (s, 1H), 7.84 (s, 1H), 7.61 (s, 1H), 7.43-7.46 (m, 1H), 6.51 (d, J=8.8 Hz, 1H), 3.77-3.95 (m, 6H), 3.39 (s, 2H), 2.52 (s, 3H), 2.36-2.56 (m, 6H), 1.81-1.85 (m, 1H), 1.65-1.68 (m, 1H)

Preparation of Compound 107

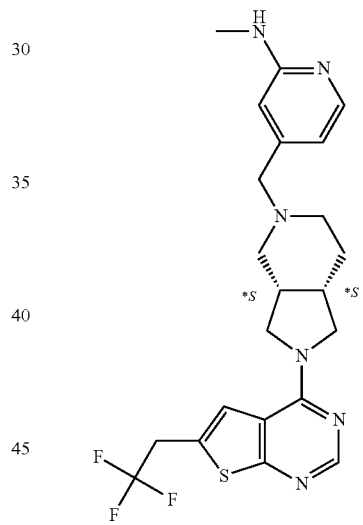

To a mixture of intermediate 47 (170 mg, 0.5 mmol) and 2-(methylamino)isonicotin-aldehyde (102 mg, 0.75 mmol) in DCM (10 mL) was added titanium(IV) isopropoxide (284 mg, 1 mmol). The mixture was stirred at room temperature for 1 h, and then, NaBH(OAc)$_3$ (212 mg, 1 mmol) was added. The reaction mixture was stirred at room temperature for 4 h. The residue was diluted in water (20 mL), extracted with DCM (30 mL×2). The combined organic layer was dried over Na$_2$SO$_4$, filtered and evaporated, The residue was purified by Prep-HPLC (Waters 2767/Qda, Column: Waters Xbridge19*150 mm 10 um, Mobile Phase A: H$_2$O (0.1% NH$_4$OH), B: ACN) to yield compound 107 (92.0 mg, 0.19 mmol, 38.0% yield) as a white solid.

$^1$H NMR CD$_3$OD (400 MHz): δ 8.27 (s, 1H), 7.86 (d, J=5.2 Hz, 1H), 7.63 (s, 1H), 6.57 (d, J=5.2 Hz, 1H), 6.51 (s, 1H), 3.82-3.97 (m, 6H), 3.42 (s, 2H), 2.85 (s, 3H), 2.30-2.60 (m, 6H), 1.81-1.85 (m, 1H), 1.65-1.68 (m, 1H)

Example B27 (Conversion)

Preparation of Compound 108

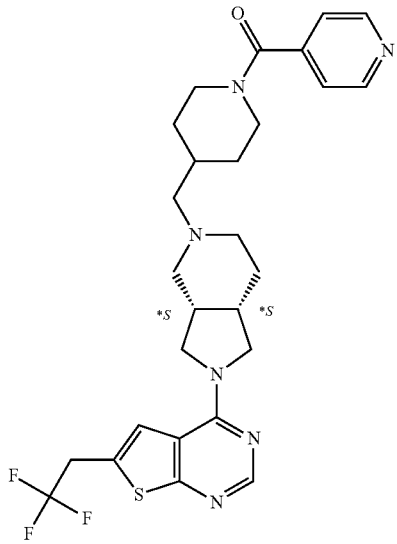 [SMILES: O=C(c1ccncc1)N1CCC(CN2CC[C@@H]3CN(c4ncnc5sc(CC(F)(F)F)cc45)C[C@@H]3C2)CC1]

To a solution of isonicotinic acid (35.0 mg, 0.335 mmol) in DCM (10 mL) was added HOBt (68 mg, 0.502 mmol), EDCI (96 mg, 0.502 mmol) and TEA (0.28 ml, 2 mmol). After stirring at room temperature for a while, the compound 70C (TFA salt of compound 70B) (300 mg, 0.335 mmol) was added. The resulting mixture was stirred at room temperature for 2 h and then concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield compound 108 (40.0 mg, 22.2% yield) as a white solid.

$^1$H NMR CD$_3$OD (400 MHz) δ 8.65 (d, J=5.6 Hz, 2H), 8.26 (s, 1H), 7.61 (s, 1H), 7.43 (d, J=5.6 Hz, 2H), 4.64-4.61 (m, 1H), 3.96-3.77 (m, 6H), 3.59-3.56 (m, 1H), 3.17-3.10 (m, 1H), 2.92-2.86 (m, 1H), 2.60-2.43 (m, 5H), 2.35-2.25 (m, 3H), 1.94-1.91 (m, 2H), 1.80-1.77 (m, 2H), 1.64-1.62 (m, 1H), 1.30-1.11 (m, 2H).

Example B28

Preparation of Compound 109

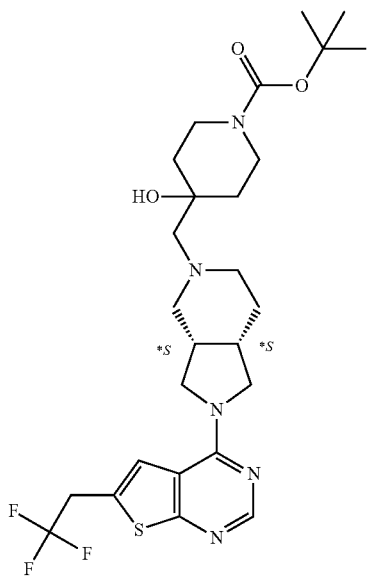 [SMILES: CC(C)(C)OC(=O)N1CCC(O)(CN2CC[C@@H]3CN(c4ncnc5sc(CC(F)(F)F)cc45)C[C@@H]3C2)CC1]

To a solution of intermediate 47 (400 mg, 0.585 mmol) in 10 ml of EtOH was added tert-butyl 1-oxa-6-azaspiro[2.5]octane-6-carboxylate (250 mg, 1.17 mmol) and K$_2$CO$_3$ (323 mg, 2.34 mmol). After stirring at 110° C. for 1 h in microwave reactor, the mixture was concentrated to give a residue which was purified by prep-HPLC (Waters 2767/Qda, Column: Waters Xbridge19*150 mm 10 um, Mobile Phase A: H$_2$O (0.1% NH$_4$OH), B: ACN) to yield compound 109 (58 mg, 17.8% yield) as a white solid.

$^1$H NMR CDCl$_3$ (400 MHz) δ 8.43 (s, 1H), 7.35 (s, 1H), 3.97-3.88 (m, 4H), 3.77-3.73 (m, 1H), 3.67-3.60 (m, 2H), 3.19-3.13 (m, 2H), 2.71-2.33 (m, 8H), 1.84-1.61 (m, 3H), 1.53-1.40 (m, 13H), 1.30-1.25 (m, 1H).

Analytical Part

NMR

NMR experiments were carried out using a Bruker Avance 500 spectrometer equipped with a Bruker 5 mm BBFO probe head with z gradients and operating at 500 MHz for the proton and 125 MHz for carbon, or using a Bruker Avance DRX 400 spectrometer using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz.

Alternatively, some NMR experiments were carried out using a Bruker Avance III 400 spectrometer at ambient temperature (298.6 K), using internal deuterium lock and equipped with 5 mm PABBO BB-probe head with z gradients and operating at 400 MHz for the proton and 100 MHz for carbon. Chemical shifts (δ) are reported in parts per million (ppm). J values are expressed in Hz.

LCMS (Liquid Chromatography/Mass Spectrometry)

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 1a

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| 1 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 50 | 10 |
| 2 | Waters: Acquity UPLC ®-DAD and Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| 3 | Waters: Acquity ® H-Class-DAD and SQD2 ™ | Waters: BEH C18 (1.7 μm, 2.1 × 100 mm) | A: 95% $CH_3COONH_4$ 7 mM/5% $CH_3CN$, B: $CH_3CN$ | 84.2% A to 10.5% A in 2.18 min, held for 1.96 min, back to 84.2% A in 0.73 min, held for 0.73 min. | 0.343 40 | 6.1 |
| 4 | Waters: Acquity UPLC ® H-Class-DAD and QDa | BEH ®-C18 (1.7 μm, 2.1 × 100 mm | A: 95% $CH_3COONH_4$ 7 mM/5% $CH_3CN$, B: $CH_3CN$ | 95% A to 5% A in 1 min, held for 1.6 min, back to 95% A in 0.2 min, held for 0.5 min. | 0.5 40 | 3.3 |
| 5 | Waters: Acquity UPLC ® H-Class-DAD and SQD 2 | Waters BEH ®C18 (1.7 μm, 2.1 × 50 mm) | A: 95% $CH_3COONH_4$ 7 mM/5% $CH_3CN$, B: $CH_3CN$ | From 95% A to 5% A in 1 min, held for 1.6 min, back to 95% A in 0.2 min, held for 0.5 min. | 0.5 40 | 3.3 |
| 6 | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10 |
| 7 | Shimadzu: LC-MS2020-SPD-M20A and Alltech 3300ELSD | SunFire C18 5 μm 50 * 4.6 mm | A: HCOOH 0.1% in water, B: HCOOH 0.1% in $CH_3CN$ | 90% A for 0.4 min, to 5% A in 1.2 min, to 1% A in 1.0 min. | 2.0 40 | 2.6 |
| 8 | Shimadzu: LC-MS2020-SPD-M20A and Alltech 3300ELSD | SunFire C18 5 μm 50 * 4.6 mm | A: HCOOH 0.1% in water, B: HCOOH 0.1% in $CH_3CN$ | 80% A for 0.4 min, to 5% A in 1.2 min, to 1% A in 1.0 min. | 2.0 40 | 2.6 |
| 9 | Shimadzu: LC-MS2020-SPD-M20A and Alltech 3300ELSD | SunFire C18 5 μm 50 * 4.6 mm | A: HCOOH 0.1% in water, B: HCOOH 0.1% in $CH_3CN$ | 70% A for 0.4 min, to 5% A in 1.2 min, to 1% A in 1.0 min. | 2.0 40 | 2.6 |
| 10 | Shimadzu: LC-MS2020-SPD-M20A | SunFire C18 3.5 μm 50 * 4.6 mm | A: HCOOH 0.1% in water B: HCOOH 0.1% in $CH_3CN$ | 90% A for 0.4 min, to 5% A in 1.2 min, to 1% A in 1.0 min. | 2.0 40 | 2.6 |
| 11 | Shimadzu: LC-MS2020-SPD-M20A | SunFire C18 3.5 μm 50 * 4.6 mm | A: HCOOH 0.1% in water B: HCOOH 0.1% in $CH_3CN$ | 70% A for 0.4 min, to 5% A in 1.2 min, to 1% A in 1.0 min. | 2.0 40 | 2.6 |
| 12 | Waters UPLC-QDa-PDA Detector | ACQUITY UPLC BEH C18 1.7 μm 2.1 * 50 mm | A: HCOOH 0.1% in water, B: HCOOH 0.1% in $CH_3CN$ | 80% A for 0.1 min, to 5% A in 1.1 min, hold 5% A in 0.8 min. | 0.6 50 | 2.0 |

TABLE 1a-continued

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| 13 | Shimadzu: LC-MS2020-SPD-M20A | SunFire C18 3.5 μm 50 * 4.6 mm | A: HCOOH 0.1% in water, B: HCOOH 0.1% in $CH_3CN$ | 80% A for 0.4 min, to 5% A in 1.2 min, to 1% A in 1.0 min. | 2.0 40 | 2.6 |

Melting Points

For a number of compounds, melting points (MP) were determined with a DSC1 (Mettler-Toledo). Melting points were measured with a temperature gradient of 10° C./minute. Maximum temperature was 300° C. Values are peak values."

For a number of compounds, melting points were obtained with a Kofler hot bench (indicated with (K)), consisting of a heated plate with linear temperature gradient, a sliding pointer and a temperature scale in degrees Celsius.

TABLE 1b

LCMS and melting point data.

| Co. No. | M.P (° C.) | $R_t$ | $[M + H]^+$ | Adduct | LCMS Method |
|---|---|---|---|---|---|
| 1 | | 2.752 | 433 | | 1 |
| 2 | | 2.714 | 419 | | 1 |
| 3 | | 3.62 | 433.2 | 491.4 $[M + CH_3COO]^-$ | 2 |
| 4 | | 3.61 | 433.2 | 491.4 $[M + CH_3COO]^-$ | 2 |
| 5 | | 3.6 | 435.3 | 493.5 $[M + CH_3COO]^-$ | 2 |
| 6 | | 3.64 | 451.2 | 509.5 $[M + CH_3COO]^-$ | 2 |
| 7 | | 3.63 | 451.3 | 509.5 $[M + CH_3COO]^-$ | 2 |
| 8 | | 2.88 | 343 | 480.4 $[M + CH_3COO]^-$ | 2 |
| 9 | | 2.42 | 437.2 | 495.4 $[M + CH_3COO]^-$ | 2 |
| 10 | | 3.33 | 468.2 | 526.4 $[M + CH_3COO]^-$ | 2 |
| 11 | | 3.33 | 466.2 | 526.4 $[M + CH_3COO]^-$ | 2 |
| 12 | | 2.98 | 454.2 | 512.3 $[M + CH_3COO]^-$ | 2 |
| 12B | | 2.85 | 454 | 512 $[M + CH_3COO]^-$ | 3 |
| 13 | | 2.42 | 437.2 | 495.4 $[M + CH_3COO]^-$ | 2 |
| 14 | | 2.59 | 437.2 | 495.4 $[M + CH_3COO]^-$ | 2 |
| 15 | | 3.62 | 475 | 533.3 $[M + CH_3COO]^-$ | 2 |
| 16 | | 3.11 | 483.2 | 541.5 $[M + CH_3COO]^-$ | 2 |
| 17 | | 2.96 | 483.4 | 541.3 $[M + CH_3COO]^-$ | 3 |
| 18 | | 2.27 | 423.2 | 481.4 $[M + CH_3COO]-$ | 2 |
| 19 | | 2.60 | 437.1 | 495.4 $[M + CH_3COO]-$ | 2 |
| Intermediate 53 | | 2.94 | 530.6 | 588.4 $[M + CH_3COO]-$ | 3 |
| 21 | | 3.46 | 437 | / | 6 |
| 22 | 140 (K) | 2.35 | 423.2 | / | 2 |
| 23 | | 2.8 | 466.5 | 524. $[M + CH_3COO]-$ | 3 |
| 24 | | 1.13 | 467.4 | 525.3 $[M + CH_3COO]-$ | 2 |
| 25 | 140 (K) | 3.71 | 399.2 | 457.3 $[M + CH_3COO]-$ | 2 |
| 26 | | 2.14 | 466.2 | / | 2 |
| 27C | | 2.33 | 423.5 | 481.3 $[M + CH_3COO]-$ | 3 |
| 27A | | 2.34 | 423.5 | 481.3 $[M + CH_3COO]-$ | 3 |
| 27D | | 2.33 | 423.5 | 481.3 $[M + CH_3COO]-$ | 3 |
| 27B | | 2.34 | 423.5 | 481.3 $[M + CH_3COO]-$ | 3 |
| 28A | | 3.6 | 385.2 | 443.3 $[M + CH_3COO]-$ | 2 |
| 28B | | 3.59 | 385.1 | 443.3 $[M + CH_3COO]-$ | 2 |
| 29 | 134 (K) | 2.58 | 405.4 | 463.3 $[M + CH_3COO]-$ | 3 |
| 30 | 140 (K) | 3.36 | 419.2 | 477.4 $[M + CH_3COO]-$ | 2 |
| 31 | 150 (K) | 3.36 | 419.1 | 477.4 $[M + CH_3COO]-$ | 2 |
| 32 | | 2.96 | 405.5 | 463.3 $[M + CH_3COO]-$ | 3 |
| 33 | | 2.96 | 405.4 | 463.3 $[M + CH_3COO]-$ | 3 |
| 34 | | 3.79 | 437 | / | 6 |
| 35A | | 3.99 | 451 | / | 6 |
| 35B | | 3.99 | 451 | / | 6 |
| 36 | | 3.34 | 399.1 | 457.2 $[M + CH_3COO]-$ | 2 |
| 37 | | 2.88 | 452.4 | 510.3 $[M + CH_3COO]-$ | 3 |
| 38 | | 2.94 | 452.1 | 510.3 $[M + CH_3COO]-$ | 2 |
| 39 | | 2.74 | 448.4 | 506.4 $[M + CH_3COO]-$ | 3 |
| 40 | | 2.8 | 448.1 | 506.4 $[M + CH_3COO]-$ | 2 |
| 41 | | 3.10 | 468.3 | 562.3 $[M + CH_3COO]-$ | 3 |
| 42 | | 3.04 | 468.4 | 526.2 $[M + CH_3COO]-$ | 3 |
| 43 | | 3.05 | 468.3 | 526.2 $[M + CH_3COO]-$ | 3 |
| 44 | | 3.17 | 464.1 | 522.2 $[M + CH_3COO]-$ | 2 |
| 45 | | 2.97 | 464.3 | 522.4 $[M + CH_3COO]-$ | 3 |
| 46 | | 2.81 | 464.1 | 522.3 $[M + CH_3COO]-$ | 2 |
| 47 | | 3.57 | 453.1 | 511.3 $[M + CH_3COO]-$ | 2 |
| 48 | | 3.29 | 447.2 | 505.4 $[M + CH_3COO]-$ | 2 |
| 49 | | 3.8 | 461.3 | 519.4 $[M + CH_3COO]-$ | 2 |

TABLE 1b-continued

LCMS and melting point data.

| Co. No. | M.P (° C.) | $R_t$ | $[M + H]^+$ | Adduct | LCMS Method |
|---|---|---|---|---|---|
| 50 | | 2.58 | 435.1 | 493.1 [M + CH$_3$COO]- | 2 |
| 51 | | 2.55 | 424.4 | 482.4 [M + CH$_3$COO]- | 3 |
| 52 | | 2.81 | 440.1 | 498.3 [M + CH$_3$COO]- | 2 |
| 53 | | 2.6 | 435.1 | 493.3 [M + CH$_3$COO]- | 2 |
| 54 | | 2.53 | 437.1 | 495.3 [M + CH$_3$COO]- | 2 |
| 55 | | 2.48 | 435.1 | 493.3 [M + CH$_3$COO]- | 2 |
| 56 | | 2.7 | 434.1 | 492.4 [M + CH$_3$COO]- | 2 |
| 57 | | 2.51 | 385.5 | 443.3 [M + CH$_3$COO]- | 3 |
| 58 | | 2.93 | 429.1 | 487.3 [M + CH$_3$COO]- | 2 |
| 59 | | 2.55 | 455.1 | 513.3 [M + CH$_3$COO]- | 2 |
| 60 | | 2.86 | 448.3 | 506.4 [M + CH$_3$COO]- | 3 |
| 61 | | 2.63 | 464.1 | 522.3 [M + CH$_3$COO]- | 3 |
| 62 | | 3.62 | 502.1 | 560.3 [M + CH$_3$COO]- | 3 |
| 63 | | 3.21 | 464.1 | 522.4 [M + CH$_3$COO]- | 2 |
| 64 | | 2.78 | 434.1 | 492.3 [M + CH$_3$COO]- | 2 |
| 65 | | 3.22 | 468.1 | 526.3 [M + CH$_3$COO]- | 2 |
| 66 | | 2.37 | 450.1 | / | 2 |
| 67 | | 2.26 | 450.1 | / | 2 |
| 68 | | 2.49 | 464.1 | 522.3 [M + CH$_3$COO]- | 2 |
| 69 | 109 (K) | 3.32 | 399.2 | 457.3 [M + CH$_3$COO]- | 2 |
| 70 | 160 (K) | 2.81 | 441.1 | 499.2 [M + CH$_3$COO]- | 2 |
| 71 | | 3.36 | 437 | / | 6 |
| 71A | | 3.48 | 437 | / | 6 |
| 71B | | 3.49 | 437 | / | 6 |
| 72 | | 2.7 | 434.1 | 492.3 [M + CH$_3$COO]- | 2 |
| 73 | | 3.22 | 425.1 | 483.2 [M + CH$_3$COO]- | 2 |
| 74 | | 2.88 | 407.4 | 465.2 [M + CH$_3$COO]- | 3 |
| 75 | | 2.13 | 467.2 | 525.4 [M + CH$_3$COO]- | 2 |
| 76 | | 2.52 | 482.2 | 540.4 [M + CH$_3$COO]- | 2 |
| 77A | | 3.17 | 479.2 | 573.4 [M + CH$_3$COO]- | 2 |
| 77B | | 3.21 | 479.2 | 537.5 [M + CH$_3$COO]- | 2 |
| 78A | | 3.18 | 479.2 | 537.4 [M + CH$_3$COO]- | 2 |
| 78B | | 3.22 | 479.2 | 537.4 [M + CH$_3$COO]- | 2 |
| 79A | | 2.3 | 451.4 | 509.4 [M + CH$_3$COO]- | 3 |
| 79B | | 2.29 | 451.4 | 509.5 [M + CH$_3$COO]- | 3 |
| 80 | | 2.13 | 440.1 | 498.3 [M + CH$_3$COO]- | 2 |
| 81 | 112 (K) | 2.27 | 466.1 | 524.5 [M + CH$_3$COO]- | 2 |
| 82 | 105 (K) | 2.24 | 466.2 | 524.4 [M + CH$_3$COO]- | 2 |
| 83 | | 2.11 | 440.1 | 498.3 [M + CH$_3$COO]- | 2 |
| 84 | | 2.47 | 423.2 | 481.4 [M + CH$_3$COO]- | 2 |
| 85 | | 1.31 | 422.4 | 480.3 [M + CH$_3$COO]- | 5 |
| Intermediate 5 | | 1.7 | 522.5 | 580.3 [M + CH$_3$COO]- | 5 |
| Intermediate 7A | | 3.21 | 443.1 | 501.3 [M + CH$_3$COO]- | 2 |
| Intermediate 7B | | 3.21 | 443.1 | 501.4 [M + CH$_3$COO]- | 2 |
| Intermediate 8 | | 1.71 | 343.2 | / | 4 |
| Intermediate 13 | | 1.59 | 581.4 | / | 5 |
| 20 | | 3.66 | 540.3 | 598.5 [M + CH$_3$COO]- | 2 |
| 70B | | 2.22 | 440.2 | 498.3 [M + CH$_3$COO]- | 2 |
| Intermediate 16 | | 1.22 | 540.5 | 584.3 [M + HCOO]- | 4 |
| Intermediate 17 | | 1.27 | 566.5 | 624.5 [M + CH3COO]- | 4 |
| Intermediate 18 | | 1.35 | 566.5 | 624.3 [M + CH$_3$COO]- | 5 |
| Intermediate 19 | | 1.21 | 540.6 | 598.4 [M + CH$_3$COO]- | 4 |
| Intermediate 20 | | 1.4 | 429.4 | 487.2 [M + CH$_3$COO]- | 5 |
| Intermediate 26 | | 1.38 | 429.4 | 487.3 [M + CH$_3$COO]- | 5 |
| Intermediate 34 | | 0.84 | 315.3 | / | 4 |
| Intermediate 35 | | 0.83 | 315.3 | / | 4 |
| Intermediate 38 | | 2.76 | 596.4 | 654.5 [M + CH$_3$COO]- | 2 |
| Intermediate 40 | | 0.98 | 509.5 | 553.3 [M + HCOO]- | 4 |
| Intermediate 45 | | 1.70 | 522.5 | 580.3 [M + CH$_3$COO]- | 5 |
| 86 | | 0.45 | 475.4 | / | 12 |
| 87 | | 1.05 | 437.1 | / | 7 |
| 88 | | 1.18 | 465.2 | / | 10 |
| 89 | | 0.83 | 473.56 | / | 9 |
| 90 | | 1.18 | 449.2 | / | 10 |
| 91 | | 1.53 | 552.2 | / | 7 |
| 92 | | 1.43 | 552.2 | / | 7 |
| 93 | | 1.47 | 538.2 | / | 7 |
| 94 | | 1.49 | 544.2 | / | 7 |
| 95 | | 1.06 | 524.2 | / | 7 |
| 96 | | 1.02 | 545.3 | / | 8 |
| 97 | | 1.083 | 481.2 | / | 7 |
| 98 | | 0.932 | 459.2 | / | 11 |
| 99 | | 0.853 | 441.2 | / | 8 |
| 100 | | 0.893 | 441.2 | / | 8 |
| 101 | | 0.823 | 427.1 | / | 8 |
| 102 | | 0.823 | 427.1 | / | 8 |
| 103 | | 0.83 | 478.0 | / | 8 |
| 104 | | 1.18 | 435.2 | / | 10 |
| 105 | | 0.80 | 449.2 | / | 13 |
| 106 | | 0.77 | 463.2 | / | 13 |
| 107 | | 0.79 | 463.2 | / | 13 |
| 108 | | 1.03 | 545.1 | / | 7 |
| 109 | | 0.98 | 556.1 | / | 8 |

Co. No. means compound number; $R_t$ means retention time in min.

SFCMS-Methods:

General Procedure for SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

TABLE 2a

Analytical SFC-MS Methods (Flow expressed in mL/min; column temperature (T) in ° C.; Run time in minutes, Backpressure (BPR) in bars, all other abbreviations used in the table below are as defined before).

| Method code | column | mobile phase | gradient | Flow Col T | Run time BPR |
|---|---|---|---|---|---|
| 1 | Daicel Chiralcel ® OJ-3 column (3 µm, 100 × 4.6 mm) | A: $CO_2$ B: MeOH(+0.3% $iPrNH_2$) | 20% B hold 3 min, | 3.5 35 | 3 103 |
| 2 | Phenomenex Luxcellulose-2 column (3 µm, 100 × 4.6 mm) | A: $CO_2$ B: EtOH(+0.3% $iPrNH_2$) | 40% B hold 3 min, | 3.5 35 | 3 103 |
| 3 | Daicel Chiralcel ® AD-3 column (3 µm, 100 × 4.6 mm) | A: $CO_2$ B: EtOH(+0.3% $iPrNH_2$) | 25% B hold 3 min, | 3.5 35 | 3 103 |
| 4 | Phenomenex Luxcellulose-2 column (3 µm, 100 × 4.6 mm) | A: $CO_2$ B: MeOH(+0.3% $iPrNH_2$) | 30% B hold 3 min, | 3.5 35 | 3 103 |
| 5 | Daicel Chiralpak ® IC-3 (3 µm, 100 × 4.6 mm) | A: $CO_2$ B: MeOH (0.3% $iPrNH_2$) | 20% B hold 3 min, | 3.5 35 | 3 105 |
| 6 | Daicel Chiralcel ® OD-3 (3 µm, 100 × 4.6 mm | A: $CO_2$ B: MeOH (0.3% $iPrNH_2$ | 15% B hold 3 min, | 3.5 35 | 3 105 |
| 7 | Daicel Chiralcel ® OJ-3 (3 µm, 100 × 4.6 mm | A: $CO_2$ B: MeOH (0.3% $iPrNH_2$) | 20% B hold 3 min, | 3.5 35 | 3 105 |
| 8 | Daicel Chiralpak ® AD-3 (3 µm, 100 × 4.6 mm) | A: $CO_2$ B: iPrOH(0.3% $iPrNH_2$) | 50% B hold 3 min, | 3.5 35 | 3 105 |
| 9 | Daicel Chiralpak ® AS-3 (3 µm, 100 × 4.6 mm) | A: $CO_2$ B: MeOH (0.3% $iPrNH_2$) | 15% B hold 3 min, | 3.5 35 | 3 105 |
| 10 | Daicel Chiralcel ® OJ-3 (3 µm, 100 × 4.6 mm | A: $CO_2$ B: EtOH (0.3% $iPrNH_2$) | 10% B hold 3 min, | 3.5 35 | 3 105 |
| 11 | Daicel Chiralcel ® AD-3 (3 µm, 100 × 4.6 mm | A: $CO_2$ B: EtOH (0.3% $iPrNH_2$) | 20% B hold 3 min | 3.5 35 | 3 105 |
| 12 | Daicel Chiralcel ® AD-3 (3 µm, 100 × 4.6 mm | A: $CO_2$ B: EtOH (0.3% $iPrNH_2$) | 20% B hold 3 min | 3.5 35 | 3 105 |
| 14 | Daicel Chiralcel ® OJ-3 (3 µm, 100 × 4.6 mm | A: $CO_2$ B: EtOH (0.3% $iPrNH_2$) | 15% B hold 3 min, | 3.5 35 | 3 105 |
| 16 | Daicel Chiralcel ® OD-3 (3 µm, 100 × 4.6 mm | A: $CO_2$ B: MeOH (0.3% $iPrNH_2$) | 10% B hold 3 min, | 3.5 35 | 3 105 |
| 17 | $UPC^2$ (Waters) AD, 5 um, 4.6*250(Daicel) | $CO_2$/IPA/ACN/DEA 85/12/3/0.03 | Hold 25 min | 2.8 35 | 25 100 |
| 18 | Daicel Chiralcel ® AD-3 column (3 µm, 100 × 4.6 mm) | A: $CO_2$ B: MeOH(+0.3% $iPrNH_2$) | 20% B hold 3 min, | 3.5 35 | 3 103 |

TABLE 2b

SFC-MS data. (elution order 'A' elutes before 'B' under the described SFC-MS conditions).

| Co. No. | $R_t$ (min) | UV % Area | Isomer elution order | SFCMS Method |
|---|---|---|---|---|
| 3 | 1.27 | 99.36 | A | 1 |
| 4 | 1.55 | 99.24 | B | 1 |
| 6 | 0.9 | 99.39 | A | 1 |
| 7 | 1.05 | 98.73 | B | 1 |
| 13 | 1.68 | 99.53 | A | 2 |
| 9 | 2.43 | 100 | B | 2 |

TABLE 2b-continued

SFC-MS data. (elution order 'A' elutes before 'B' under the described SFC-MS conditions).

| Co. No. | R$_t$ (min) | UV % Area | Isomer elution order | SFCMS Method |
|---|---|---|---|---|
| 11 | 2.69 | 97.46 | A | 3 |
| 10 | 3.2 | 98.57 | B | 3 |
| 12 | 2.17 | 100 | A | 4 |
| 12B | 2.62 | 100 | B | 4 |
| 16 | 1.60 | 98.69 | B | 1 |
| 17 | 1.34 | 99.33 | A | 1 |
| 30 | 2.19 | 100 | A | 6 |
| 31 | 2.52 | 100 | B | 6 |
| 32 | 1.46 | 99.67 | B | 1 |
| 33 | 1.32 | 100 | A | 1 |
| 69 | 2.18 | 98.87 | A | 5 |
| 36 | 2.4 | 99.7 | B | 5 |
| 80 | 1.45 | 100 | B | 8 |
| 81 | 1.35 | 100 | A | 9 |
| 82 | 1.81 | 98.88 | B | 9 |
| 83 | 0.83 | 98.7 | A | 8 |
| 78A | 1.57 | 100 | A | 12 |
| 78B | 1.86 | 98.4 | B | 12 |
| 77A | 0.96 | 100 | A | 14 |
| 77B | 1.2 | 98.0 | B | 14 |
| 79A* | 1.77 | 100 | A | 14 |
| 79B* | 2.24 | 99 | B | 14 |
| Intermediate 7A | 1.27 | 100 | A | 11 |
| Intermediate 7B | 1.57 | 98 | B | 11 |
| Intermediate 47 | 5.044 | — | A | 17 |
| Intermediate 3A | 1.50 | 99.5 | A | 18 |
| Intermediate 3B | 2.05 | 99.6 | B | 18 |

*Compounds 79A and 79B were obtained when Compound 79 was separated. Compound 79A elutes before (isomer elution order A) before compound 79B (isomer elution order B) under the described SFC-MS conditions.

Optical Rotation (OR)

Optical Rotation is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (DMF for example). The cell is filled with the solution and put into the polarimeter at a temperature of 20° C. The OR is read with 0.004° of precision.

Calculation of the concentration: weight in gram×100/volume in ml

Specific rotation (OR): $[\alpha]_d^{20}$: (read rotation×100)/(1.000 dm×concentration).

$^d$ is sodium D line (589 nanometer).

TABLE 3

| Co. No. | OR (°) | Wavenlength (nm) | Conc. |
|---|---|---|---|
| 3 | +39.36 | 365 | 0.282 |
| 4 | −40.44 | 365 | 0.272 |
| 7 | −52.3 | 365 | 0.283 |
| 9 | −11.36 | 589 | 0.308 |
| 10 | −17.19 | 589 | 0.285 |
| 11 | +15.45 | 589 | 0.246 |
| 12 | −13.22 | 589 | 0.295 |
| 12B | +5 | 589 | 0.24 |
| 13 | +34.75 | 589 | 0.282 |
| 16 | +96.99 | 589 | 0.266 |
| 17 | −99.64 | 589 | 0.28 |
| 30 | +70.46 | 589 | 0.369 |
| 31 | −73.68 | 589 | 0.285 |
| 32 | −12.67 | 589 | 0.3 |
| 33 | +4.62 | 589 | 0.26 |
| 36 | +23.29 | 589 | 0.292 |
| 37 | +32.09 | 589 | 0.215 |
| 38 | +26.28 | 589 | 0.228 |
| 39 | +30.25 | 589 | 0.225 |
| 41 | +20.04 | 589 | 0.235 |
| 42 | +44.3 | 589 | 0.221 |
| 43 | +20.16 | 589 | 0.238 |
| 44 | +23.21 | 589 | 0.232 |
| 45 | +41.42 | 589 | 0.249 |
| 46 | +21.24 | 589 | 0.235 |
| 48 | +22.51 | 589 | 0.235 |
| 50 | +29.74 | 589 | 0.235 |
| 51 | +27.13 | 589 | 0.258 |
| 52 | +35.71 | 589 | 0.266 |
| 53 | +32.64 | 589 | 0.288 |
| 54 | +15.2 | 589 | 0.296 |
| 55 | +30.38 | 589 | 0.293 |
| 56 | +28.99 | 589 | 0.276 |
| 57 | +28.74 | 589 | 0.209 |
| 59 | +24.83 | 589 | 0.242 |
| 60 | +22.51 | 589 | 0.231 |
| 61 | +24.01 | 589 | 0.212 |
| 62 | +25.47 | 589 | 0.216 |
| 66 | +33.0 | 589 | 0.221 |
| 67 | +45.44 | 589 | 0.253 |
| 68 | +32.11 | 589 | 0.234 |
| 69 | −30.37 | 589 | 0.27 |
| 70 | +32.69 | 589 | 0.26 |
| 71B | +31.67 | 589 | 0.24 |
| 72 | −7.09 | 589 | 0.240 |
| 73 | +26.78 | 589 | 0.243 |
| 74 | +32.16 | 589 | 0.224 |
| 76 | +31.81 | 589 | 0.239 |
| 78A | −8.8 | 589 | 0.25 |
| 78B | −17.04 | 589 | 0.27 |
| 79A | +5.75 | 589 | 0.243 |
| 79B | +28.82 | 589 | 0.219 |
| 80 | +19.08 | 589 | 0.262 |
| 81 | +11.11 | 589 | 0.288 |
| 82 | −76.95 | 589 | 0.295 |
| 83 | −66.31 | 589 | 0.279 |
| Intermediate 7A | +29.73 | 589 | 0.296 |
| Intermediate 7B | −29.43 | 589 | 0.265 |
| 20 | +13.1 | 589 | 0.247 |
| 70B | +38.06 | 589 | 0.250 |

OR data: solvent: DMF; temperature: 20° C.; 'conc' means concentration (g/100 mL); 'OR' means optical rotation.

Pharmacological Part

1) Menin/MLL Fluorescence Polarization Assay

To a non-surface binding, black 384-well microtiter plate was added 50 nL 160× test compound in DMSO and 4 μL 2× menin in assay buffer (40 mM Tris-HCl, pH 7.5, 50 mM NaCl, 1 mM DTT and 0.001% Tween 20). After incubation of test compound and menin for 10 min at ambient temperature, 4 μL 2×FITC-MBM1 peptide (FITC-β-alanine-SARWRFPARPGT-NH$_2$) in assay buffer was added, the microtiter plate centrifuged at 1000 rpm for 1 min and the assay mixtures incubated for 15 min at ambient temperature. The relative amount of menin: FITC-MBM1 complex present in an assay mixture is determined by measuring the fluorescence polarization (FP) of the FITC label with a BMG Pherastar plate reader (ex. 485 nm/em. 520 nm) at ambient temperature. The final concentrations of reagents in the binding assay are 100 nM menin, 5 nM FITC-MBM1 peptide and 0.625% DMSO in assay buffer. Dose-response titrations of test compounds are conducted using an 11 point, three-fold serial dilution scheme, starting at 31 μM.

Compound potencies were determined by first calculating % inhibition at each compound concentration according to equation 1:

$$\% \text{ inhibition} = ((HC-LC)-(FP^{compound}-LC))/(HC-LC))*100 \quad \text{(Eqn 1)}$$

Where LC and HC are the FP values of the assay in the presence or absence of a saturating concentration of a compound that competes with FITC-MBM1 for binding to menin, and $FP^{compound}$ is the measured FP value in the presence of the test compound. HC and LC FP values represent an average of at least 16 replicates per plate. For each test compound, % inhibition values were plotted vs. the logarithm of the test compound concentration, and the $IC_{50}$ value derived from fitting these data to equation 2:

$$\% \text{ inhibition} = \text{Bottom} + (\text{Top}-\text{Bottom})/(1+10\textasciicircum((\log IC_{50} - \log[cmpd])*h)) \quad \text{(Eqn 2)}$$

Where Bottom and Top are the lower and upper asymptotes of the dose-response curve, respectively, $IC_{50}$ is the concentration of compound that yields 50% inhibition of signal and h is the Hill coefficient.

2) Proliferation Assay

The anti-proliferative effect of menin/MLL protein/protein interaction inhibitor test compounds was assessed in human leukemia cell lines. The cell lines MV-4-11 and MOLM14 harbor MLL translocations and express the MLL fusion proteins MLL-AF4 and MLL-AF9, respectively, as well as the wildtype protein from the second allele. Therefore, the MLL rearranged cell lines MV-4-11 and MOLM14 exhibit stem cell-like HOXA/MEIS1 gene expression signatures. K562 and KG1 were used as a control cell lines containing two MLL wildtype alleles in order to exclude compounds that display general cytotoxic effects.

MV-4-11 and MOLM14 were cultured in RPMI-1640 (Sigma Aldrich) supplemented with 10% fetal bovine serum (HyClone), 2 mM L-glutamine (Sigma Aldrich) and 50 µg/ml gentamycin (Gibco). K562 were propagated in RPMI-1640 (Sigma Aldrich) supplemented with 20% fetal bovine serum (HyClone), 2 mM L-glutamine (Sigma Aldrich) and 50 µg/ml gentamycin (Gibco). KG1 were cultured in Iscove's MDM (Gibco) supplemented with 20% fetal bovine serum (HyClone), 2 mM L-glutamine (Sigma Aldrich) and 50 µg/ml gentamycin (Gibco). Cells were kept at 0.3-2.5 million cells per ml during culturing and passage numbers did not exceed 25.

In order to assess the anti-proliferative effects, 1,500 MV-4-11, 300 MOLM14, 750 K562 or 1,300 KG1 cells were seeded in 200 µl media per well in 96-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 d at 37° C. and 5% $CO_2$. Spheroid like growth was monitored in real-time by live-cell imaging (IncuCyteZOOM, Essenbio, 4× objective) acquiring one image every four hours for 8 d. Confluence (%) as a measure of spheroid size was determined using an integrated analysis tool.

In order to determine the cumulative effect of the test compounds over time, the area under the curve (AUC) in a plot of confluence against time was calculated. Confluence at the beginning of the experiment (t=0) was used as baseline for the AUC calculation.

Absolute $IC_{50}$ values were calculated according to the following procedure:

% Control=(AUC sample/AUC control)*100

AUC control=mean AUC of control values (cells without compound/DMSO as vehicle control)

A non-linear curve fit was applied using the least squares (ordinary) fit method to the plot of % control versus compound concentration. Based on this, the absolute $IC_{50}$ value (half maximal inhibitory concentration of the test compound causing an anti-proliferative effect of 50% relative to the vehicle control) was calculated.

3) Menin/MLL Homogenous Time-Resolved Fluorescence (HTRF) Assay

To an untreated, white 384-well microtiter plate was added 40 nL 200× test compound in DMSO and 4 µL 2× terbium chelate-labeled menin (vide infra for preparation) in assay buffer (40 mM Tris-HCl, pH 7.5, 50 mM NaCl, 1 mM DTT and 0.05% Pluronic F-127). After incubation of test compound and terbium chelate-labeled menin for 5 min at ambient temperature, 4 µL 2×FITC-MBM1 peptide (FITC-β-alanine-SARWRFPARPGT-NH$_2$) in assay buffer was added, the microtiter plate centrifuged at 1000 rpm for 1 min and the assay mixtures incubated for 15 min at ambient temperature. The relative amount of menin•FITC-MBM1 complex present in an assay mixture is determined by measuring the homogenous time-resolved fluorescence (HTRF) of the terbium/FITC donor/acceptor fluorophore pair using a BMG Pherastar plate reader (ex. 337 nm/terbium em. 490 nm/FITC em. 520 nm) at ambient temperature. The degree of fluorescence resonance energy transfer (the HTRF value) is expressed as the ratio of the fluorescence emission intensities of the FITC and terbium fluorophores ($F^{em}$ 520 nm/$F^{em}$ 490 nm). The final concentrations of reagents in the binding assay are 100 pM terbium chelate-labeled menin, 75 nM FITC-MBM1 peptide and 0.5% DMSO in assay buffer. Dose-response titrations of test compounds are conducted using an 11 point, three-fold serial dilution scheme, starting at 31 µM.

Compound potencies were determined by first calculating % inhibition at each compound concentration according to equation 1:

$$\% \text{ inhibition} = ((HC-LC)-(HTRF^{compound}-LC))/(HC-LC))*100 \quad \text{(Eqn 1)}$$

Where LC and HC are the HTRF values of the assay in the presence or absence of a saturating concentration of a compound that competes with FITC-MBM1 for binding to menin, and $HTRF^{compound}$ is the measured HTRF value in the presence of the test compound. HC and LC HTRF values represent an average of at least 16 replicates per plate. For each test compound, % inhibition values were plotted vs. the logarithm of the test compound concentration, and the $IC_{50}$ value derived from fitting these data to equation 2:

$$\% \text{ inhibition} = \text{Bottom} + (\text{Top}-\text{Bottom})/(1+10\textasciicircum((\log IC_{50} - \log[cmpd])*h)) \quad \text{(Eqn 2)}$$

Where Bottom and Top are the lower and upper asymptotes of the dose-response curve, respectively, $IC_{50}$ is the concentration of compound that yields 50% inhibition of signal and h is the Hill coefficient.

Preparation of Terbium cryptate labeling of Menin: Menin (a.a. 1-610-6×his tag) was labeled with terbium cryptate as follows. 2 mg of Menin was buffer exchanged into 1× phosphate buffered saline. 16 uM Menin was incubated with 4-fold molar excess NHS-terbium cryptate (Cisbio Bioassays, Bedford, Mass.) for 2 hours at room temperature. The labeled protein was purified away from free label by running the reaction over a Superdex 200 Increase 10/300 GL column at 0.75 ml/min. Peak fractions were collected, aliquoted and frozen at −80° C.

MENIN Protein Sequence (SEQ ID NO: 1):
MGLKAAQKTLFPLRSIDDVVRLFAAELGREEPDLVLLSLVLGFVEHFLA

VNRVIPTNVPELTFQPSPAPDPPGGLTYFPVADLSIIAALYARFTAQIR

GAVDLSLYPREGGVSSRELVKKVSDVIWNSLSRSYFKDRAHIQSLFSFI

TGTKLDSSGVAFAVVGACQALGLRDVHLALSEDHAWVVFGPNGEQTAEV

TWHGKGNEDRRGQTVNAGVAERSWLYLKGSYMRCDRKMEVAFMVCAINP

SIDLHTDSLELLQLQQKLLWLLYDLGHLERYPMALGNLADLEELEPTPG

RPDPLTLYHKGIASAKTYYRDEHIYPYMYLAGYHCRNRNVREALQAWAD

TATVIQDYNYCREDEEIYKEFFEVANDVIPNLLKEAASLLEAGEERPGE

QSQGTQSQGSALQDPECFAHLLRFYDGICKWEEGSPTPVLHVGWATFLV

QSLGRFEGQVRQKVRIVSREAEAAEAEEPWGEEAREGRRRGPRRESKPE

EPPPPKKPALDKGLGTGQGAVSGPPRKPPGTVAGTARGPEGGSTAQVPA

PAASPPPEGPVLTFQSEKMKGMKELLVATKINSSAIKLQLTAQSQVQMK

KQKVSTPSDYTLSFLKRQRKGLHHHHHH

TABLE 4

Biological data in the Menin fluorescence polarization (FP) assay (1), Menin/MLL homogenous time-resolved fluorescence (HTRF) assay (3) and proliferation assay (2). Co. No. means compound number. The values in table 4 are averaged values over all measurements.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 1 | 0.033 | 113 | 1.5 | 4.4 | 13.1 | |
| 2 | 0.34 | 797 | 7.3 | 9.8 | >15 | |
| 4 | 0.23 | 69 | 8.3 | 12.8 | | |
| 3 | 0.089 | 61 | 2.0 | 3.8 | | |
| 7 | 0.63 | 510 | | 14.6 | >15 | |
| 6 | 0.21 | 476 | 1.4 | 3.3 | 9.0 | |
| 16 | 1.53 | | | | | |
| 17 | 1.85 | | | | | |
| 13 | 0.52 | | 13.7 | >15 | | |
| 10 | 0.25 | 118 | 4.4 | 2.0 | | |
| 11 | 0.59 | 680 | >15 | >15 | | |
| 12 | 0.43 | 860 | 2.1 | 9.2 | | |
| 9 | 0.098 | 106 | 3.5 | 10.3 | | |
| 14 | 1.12 | | | | | |
| 15 | 0.13 | 120 | 3.9 | 5.9 | 14 | |
| 84 | 1.02 | 906 | | | | |
| 23 | 0.22 | 366 | 1.7 | 4.3 | | |
| 19 | 1.77 | 4571 | | | | |
| 18 | 0.52 | 1133 | >15 | >15 | | |
| 22 | 2.41 | | | | | |
| 34 | 0.78 | 1976 | | | | |
| 21 | 1.77 | 2124 | | | | |
| 32 | 1.56 | 2776 | | | | |
| 33 | 1.19 | 2100 | | | | |
| 27A | 4.54 | 10046 | | | | |
| 27C | | 4530 | | | | |
| 27B | 3.65 | 8989 | | | | |
| 27D | | ~6912 | | | | |
| 28A | 1.17 | 1727 | | | | |
| 28B | 1.38 | 2487 | | | | |
| 29 | | 3448 | | | | |
| 71 | 0.088 | 70 | 0.84 | 6.7 | | |
| 85 | | 103 | 3.1 | | | |
| 30 | | ~1259 | | | | |
| 31 | | 1084 | | | | |
| 71B | | 54 | 0.42 | 2.2 | >15 | >15 |
| 87 | | 20 | | | | |
| 71A | | 985 | | | | |
| 69 | | 57 | 1.8 | | | |
| 36 | | 15 | 0.22 | 1.4 | >15 | >15 |
| 102 | | 13 | 0.24 | | | |
| 82 | | 653 | 7.9 | | | |
| 81 | | 410 | 5.7 | | | |
| 80 | | 933 | | | | |
| 83 | | 985 | | | | |
| 26 | | 54 | 4.7 | 5.6 | | |
| 35A | | 8327 | | | | |
| 35B | | >25000 | | | | |
| 25 | | 546 | | | | |
| 78A | | 520 | | | | |
| 78B | | 1319 | | | | |
| 77A | | 201 | | | | |
| 77B | | 1625 | | | | |
| 56 | | 41 | 1.4 | | | |
| 55 | | 75 | 3.3 | | | |
| 54 | | 97 | 2.1 | | | |
| 70 | | 18 | 0.56 | 1.4 | >15 | >15 |
| 53 | | 252 | | | | |
| 52 | | 41 | 0.86 | | | |
| 75 | | 28 | 1.0 | | | |
| 51 | | 62 | 2.3 | | | |
| 20 | | 31 | 0.38 | 0.98 | >15 | |
| 48 | | 446 | | | | |
| 73 | | 2455 | | | | |
| 70B | | 24 | 0.28 | 2 | >15 | |
| 72 | | 991 | | | | |
| 49 | | 44 | 1.9 | | | |
| 46 | | 105 | 1.5 | | | |
| 38 | | 208 | 2.3 | | | |
| 47 | | 55 | 2.3 | | | |
| 50 | | 281 | | | | |
| 45 | | 16 | 0.28 | 1.8 | | >15 |
| 44 | | 87 | 2.1 | | | >15 |
| 76 | | 105 | 2.9 | | | |
| 40 | | 25 | 0.26 | 1.6 | | 8.1 |
| 79A | | 955 | | | | |
| 79B | | 964 | | | | |
| 74 | | 2220 | | | | |
| 43 | | 97 | 1.3 | | | |
| 42 | | 21 | 0.47 | 1.6 | | >15 |
| 41 | | 74 | 0.84 | 1.2 | | 4.5 |
| 39 | | 165 | 0.67 | | | 2.5 |
| 37 | | 41 | 0.48 | 1.3 | | >15 |
| 60 | | 95 | 0.66 | 0.22 | | 1.8 |
| 57 | | 67 | 0.59 | 2.1 | | >15 |
| 58 | | 63 | 0.99 | | | >15 |
| 59 | | 212 | 1.8 | | | |
| 61 | | 146 | 1.7 | | | |
| 67 | | 27 | 0.32 | 3.2 | | >15 |
| 64 | | 25 | 0.55 | 0.77 | | 8.4 |
| 65 | | 56 | 1.2 | | | |
| 63 | | 61 | 0.65 | 0.8 | | 9.5 |
| 66 | | 492 | | | | |
| 62 | | 36 | 2.2 | | | |
| 68 | | 266 | 2.9 | | | |
| 99 | | 33 | 0.24 | | | >15 |
| 100 | | 57 | 0.93 | | | >15 |
| 101 | | 28 | 0.41 | | | >15 |
| 97 | | 150 | 2 | | | |
| 98 | | 504 | | | | |
| 88 | | 267 | | | | |
| 89 | | 24 | 0.24 | | | |
| 90 | | 317 | | | | |
| 86 | | 198 | 6.6 | | | |
| 91 | | 30 | 1.2 | | | |
| 92 | | 14 | 0.45 | | | |

TABLE 4-continued

Biological data in the Menin fluorescence polarization (FP) assay (1), Menin/MLL homogenous time-resolved fluorescence (HTRF) assay (3) and proliferation assay (2). Co. No. means compound number. The values in table 4 are averaged values over all measurements.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 93 |  | 20 | 0.58 |  |  |  |
| 94 |  | 18 | 0.43 |  |  |  |
| 95 |  | 69 | 2.1 |  |  |  |
| 96 |  | 45 | 1.0 |  |  |  |
| 104 |  | 375 |  |  |  |  |
| 105 |  | 11 | 0.22 |  |  |  |
| 106 |  | 10 | 0.19 |  |  |  |
| 107 |  | 23 | 0.34 |  |  |  |
| 108 |  | 23 | 0.87 |  |  |  |
| 103 |  | 106 | 1.1 |  |  |  |
| 109 |  | 714 |  |  |  |  |

TABLE 5

Biological data in the Menin fluorescence polarization (FP) assay (1), Menin/MLL homogenous time-resolved fluorescence (HTRF) assay (3) and proliferation assay (2). Co. No. means compound number. The values in table 5 are values for individual measurements (not averaged): in case a value was determined more than 1 time, each value is reported individually in Table 5.

| Co. No. | (1) Menin FP assay (IC$_{50}$ (μM)) | (3) Menin HTRF assay (IC$_{50}$ (nM)) | (2) Spheroid assay MV-4-11 (IC$_{50}$ (μM)) | (2) Spheroid assay MOLM14 (IC$_{50}$ (μM)) | (2) Spheroid assay K562 (IC$_{50}$ (μM)) | (2) Spheroid assay KG1 (IC$_{50}$ (μM)) |
|---|---|---|---|---|---|---|
| 8 |  |  | 2.1 | 5.7 |  |  |
|  | 0.101 | 48 | 2.3 | >15 | >15 |  |
| 5 |  |  | 2.1 |  |  |  |
|  | ~0.17 |  | 2.1 | 4.3 |  |  |
|  | 6.0 | 9 | >15 | 4.3 | >15 |  |
| 24 |  |  | 0.09 |  |  |  |
|  |  | 244 | 8.2 |  |  |  |

The invention claimed is:
1. A compound of Formula (1)

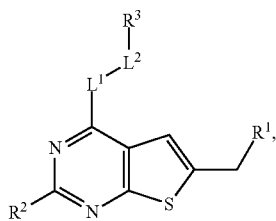

(I)

or a tautomer or a stereoisomeric form thereof, wherein
$R^1$ is selected from the group consisting of $CH_3$, $CH_2F$, $CHF_2$ and $CF_3$;
$R^2$ is selected from the group consisting of hydrogen and $CH_3$;
$L^1$ is a 7- to 9-membered fused heterocycle of Formula (a)

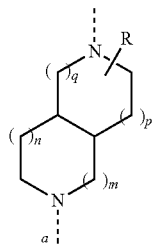

(a)

wherein
a represents the position of linkage to the thienopyrimidinyl heterocycle;
m is equal to 0 or 1;
n is equal to 0 or 1;
p is equal to 0, 1 or 2;
q is equal to 0 or 1;
R is selected from the group consisting of hydrogen and oxo; and
-$L^2$-$R^3$ is selected from (a), (b), (c), (d) or (e), wherein
(a) $L^2$ is selected from the group consisting of >$SO_2$, >$CR^{4a}R^{4b}$, and —$CHR^{4a}CHR^5$—; wherein
$R^{4a}$ is selected from the group consisting of hydrogen; —C(=O)$NR^{7a}R^{7b}$;
$C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;
$R^{4b}$ is selected from the group consisting of hydrogen and methyl; or
$R^{4a}$ and $R^{4b}$ together with the carbon atom to which they are attached form a $C_{3-5}$cycloalkyl or a C-linked 4- to 6-membered heterocyclyl containing an oxygen atom;
$R^5$ is selected from the group consisting of hydrogen; —$OR^6$; —$NR^{7a}R^{7b}$; —C(=O)$NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom; wherein $R^6$, $R^{7a}$, $R^{7b}$, $R^8$, $R^{9a}$ and $R^{9b}$ are each independently selected from the group consisting of hydrogen; $C_{1-4}$alkyl optionally substituted with a substituent selected from the group consisting of fluoro, —CN and —C(=O)$NR^{10a}R^{10b}$, and $C_{2-4}$alkyl substituted with a substituent selected from the group consisting of —$OR^{11}$ and —$NR^{10a}R^{10b}$; wherein
$R^{10a}$, $R^{10b}$ and $R^{11}$ are each independently selected from the group consisting of hydrogen; $C_{1-4}$alkyl; and C-linked 4- to 7-membered non-aromatic heterocyclyl containing at least one nitrogen, oxygen or sulfur atom; and
$R^3$ is selected from the group consisting of Ar; $Het^1$; $Het^2$; and a 7- to 10-membered saturated spirocarbobicyclic system; or
(b) $L^2$ is selected from >$CR^{4c}R^{4d}$ and —$CHR^{4c}CHR^{5a}$—; wherein $R^{4c}$, $R^{4d}$ and $R^{5a}$ are each independently selected from the group consisting of hydrogen and $C_{1-4}$alkyl; and
$R^3$ is selected from the group consisting of

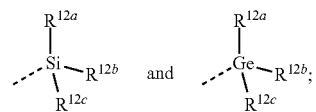

and wherein $R^{12a}$, $R^{12b}$, and $R^{12c}$ are each independently selected from the group consisting of $C_{1-6}$alkyl optionally substituted with a —OH or a —$NH_2$ substituent; and —$OC_{1-6}$alkyl; or
(c) -$L^2$-$R^3$ is $C_{1-6}$alkyl optionally substituted with one, two or three fluoro or —OH substituents; or
(d) -$L^2$-$R^3$ is

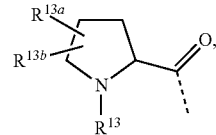

wherein
$R^{13}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{14}$ and —$NR^{15a}R^{15b}$; wherein
$R^{14}$, $R^{15a}$ and $R^{15b}$ are each independently selected from the group consisting of hydrogen; $C_{1-4}$alkyl optionally substituted with a substituent selected from the group consisting of fluoro, —CN, and —C(=O)$NR^{16a}R^{16b}$; $C_{2-4}$alkyl substituted with a substituent selected from the group consisting of —$OR^{17}$ and —$NR^{16a}R^{16b}$; and C-linked 4- to 7-membered non-aromatic heterocyclyl containing at least one nitrogen, oxygen or sulfur atom; wherein
$R^{16a}$, $R^{16b}$ and $R^{17}$ are each independently selected from the group consisting of hydrogen and $C_{1-4}$alkyl; and
$R^{13a}$ is selected from the group consisting of hydrogen, fluoro and $C_{1-4}$alkyl;

$R^{13b}$ is selected from the group consisting of hydrogen, fluoro, —$OC_{1-4}$alkyl, and $C_{1-4}$alkyl optionally substituted with 1, 2 or 3 fluoro substituents; or $R^{13a}$ and $R^{13b}$ are bound to the same carbon atom and together form a $C_{3-5}$cycloalkyl or a C-linked 4- to 6-membered heterocyclyl containing an oxygen atom; or (e) -$L^2$-$R^3$ is

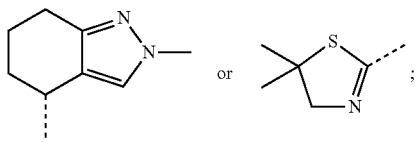

and wherein

Ar is phenyl or naphthyl, each of which may be optionally substituted with one, two, or three substituents each independently selected from the group consisting of halo, —CN, —$OR^{18}$, —$NR^{19a}R^{19b}$, and $C_{1-4}$alkyl optionally substituted with a substituent selected from the group consisting of fluoro, —CN, —$OR^{20}$, —$NR^{21a}R^{21b}$ and —$C(=O)NR^{21a}R^{21b}$;

$Het^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzothiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —$OR^{18}$, —$NR^{19a}R^{19b}$, $C_{3-6}$cycloalkyl, and $C_{1-4}$alkyl optionally substituted with a substituent selected from the group consisting of fluoro, —CN, —$OR^{20}$, —$NR^{21a}R^{21b}$, and —$C(=O)NR^{21a}R^{21b}$, and $Het^2$ is a non-aromatic heterocyclyl optionally substituted with one, two, or three substituents each independently selected from the group consisting of halo, —CN, —$OR^{18}$, —$NR^{19a}R^{19b}$, —$C(=O)C_{1-6}$alkyl, —$C(=O)$—O—$C_{1-6}$alkyl, —$C(=O)$—$C_{3-6}$cycloalkyl, —$C(=O)$—$Ar^2$, —$C(=O)$—$Het^3$, —$C(=O)$—$Het^4$, and $C_{1-4}$alkyl optionally substituted with a substituent selected from the group consisting of fluoro, —CN, —$OR^{20}$, —$NR^{21a}R^{21b}$, and —$C(=O)NR^{21a}R^{21b}$, $Ar^2$ is phenyl;
$Het^3$ is pyridyl;
$Het^4$ is oxetanyl, tetrahydrofuranyl, or tetrahydropyranyl; wherein $R^{18}$, $R^{19a}$, $R^{19b}$, $R^{20}$, $R^{21a}$, and $R^{21b}$ are each independently selected from the group consisting of hydrogen; $C_{1-4}$alkyl optionally substituted with a substituent selected from the group consisting of fluoro and —$C(=O)NR^{22a}R^{22b}$, and $C_{2-4}$alkyl substituted with a substituent selected from the group consisting of —$OR^{23}$ and —$NR^{22a}R^{22b}$; wherein $R^{22a}$, $R^{22b}$ and $R^{23}$ are each independently selected from the group consisting of hydrogen; $C_1$-4alkyl; and C-linked 4- to 7-membered non-aromatic heterocyclyl containing at least one nitrogen, oxygen or sulfur atom;

or a pharmaceutically acceptable salt or a solvate thereof.

2. The compound according to claim 1, wherein -$L^2$-$R^3$ is selected from (a), (b), (c), (d) or (e), wherein (a) $L^2$ is selected from the group consisting of >$SO_2$, >$CR^{4a}R^{4b}$, and —$CHR^{4a}CHR^5$—; wherein $R^{4a}$ is selected from the group consisting of hydrogen; —$C(=O)NR^{7a}R^{7b}$;

$C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom;

$R^{4b}$ is selected from the group consisting of hydrogen and methyl; or $R^{4a}$ and $R^{4b}$ together with the carbon atom to which they are attached form a $C_{3-5}$cycloalkyl or a C-linked 4- to 6-membered heterocyclyl containing an oxygen atom;

$R^5$ is selected from the group consisting of hydrogen; —$OR^6$; —$NR^{7a}R^{7b}$;

$C(=O)NR^{7a}R^{7b}$; $C_{1-4}$alkyl optionally substituted with a substituent selected from the group consisting of fluoro, —CN, —$OR^8$, and —$NR^{9a}R^{9b}$; and C-linked 4- to 7-membered non-aromatic heterocyclyl containing at least one nitrogen, oxygen or sulfur atom; wherein $R^6$, $R^{7a}$, $R^{7b}$, $R^8$, $R^{9a}$ and $R^{9b}$ are each independently selected from the group consisting of hydrogen; $C_{1-4}$alkyl optionally substituted with a substituent selected from the group consisting of fluoro, —CN and —$C(=O)NR^{10a}R^{10b}$; and $C_{2-4}$alkyl substituted with a substituent selected from the group consisting of —$OR^{11}$ and —$NR^{10a}R^{10b}$; wherein $R^{10a}$, $R^{10b}$ and $R^{11}$ are each independently selected from the group consisting of hydrogen; $C_{1-4}$alkyl; and C-linked 4- to 7-membered non-aromatic heterocyclyl containing at least one nitrogen, oxygen or sulfur atom; and $R^3$ is selected from the group consisting of Ar; $Het^1$; $Het^2$; and a 7- to 10-membered saturated spirocarbobicyclic system; or (b) $L^2$ is selected from >$CR^{4c}R^{4d}$ and —$CHR^{4c}CHR^{5a}$—; wherein $R^{4c}$, $R^{4d}$ and $R^{5a}$ are each independently selected from the group consisting of hydrogen and $C_{1-4}$alkyl; and $R^3$ is selected from the group consisting of

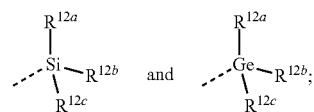

wherein $R^{12a}$, $R^{12b}$ and $R^{12c}$ are each independently selected from the group consisting of $C_{1-6}$alkyl optionally substituted with a —OH or a —$NH_2$ substituent; and —$OC_{1-6}$alkyl; or (c) -$L^2$-$R^3$ is $C_{1-6}$alkyl optionally substituted with one, two or three fluoro substituents; or (d) -L²-R³ is

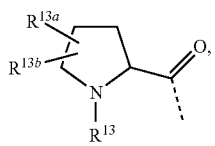

wherein
R¹³ is selected from the group consisting of hydrogen; C$_{1-4}$alkyl optionally substituted with a fluoro or a —CN substituent; and C$_{2-4}$alkyl substituted with a substituent selected from the group consisting of —OR¹⁴ and —NR$^{15a}$R$^{15b}$; wherein
R¹⁴, R$^{15a}$ and R$^{15b}$ are each independently selected from the group consisting of hydrogen; C$_{1-4}$alkyl optionally substituted with a substituent selected from the group consisting of fluoro, —CN, and —C(=O)NR$^{16a}$R$^{16b}$; C$_{2-4}$alkyl substituted with a substituent selected from the group consisting of —OR¹⁷ and —NR$^{16a}$R$^{16b}$; and
C-linked 4- to 7-membered non-aromatic heterocyclyl containing at least one nitrogen, oxygen or sulfur atom; wherein
R$^{16a}$, R$^{16b}$ and R¹⁷ are each independently selected from the group consisting of hydrogen and C$_{1-4}$alkyl; and
R$^{13a}$ is selected from the group consisting of hydrogen, fluoro and C$_{1-4}$alkyl;
R$^{13b}$ is selected from the group consisting of fluoro, —OC$_{1-4}$alkyl, and C$_{1-4}$alkyl optionally substituted with 1, 2 or 3 fluoro substituents; or
R$^{13a}$ and R$^{13b}$ are bound to the same carbon atom and together form a C$_{3-5}$cycloalkyl or a C-linked 4- to 6-membered heterocyclyl containing an oxygen atom; or (e) -L²-R³ is

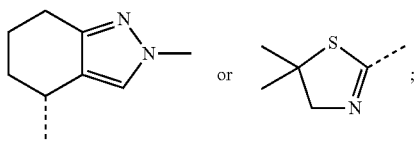

and wherein
Ar is phenyl or naphthyl, each of which may be optionally substituted with one, two, or three substituents each independently selected from the group consisting of halo, —CN, —OR¹⁸, —NR$^{19a}$R$^{19b}$, and C$_{1-4}$alkyl optionally substituted with a substituent selected from the group consisting of fluoro, —CN, —OR²⁰, —NR$^{21a}$R$^{21b}$, and —C(=O)NR$^{21a}$R$^{21b}$;
Het¹ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; or a bicyclic heteroaryl selected from the group consisting of imidazothiazolyl, imidazoimidazolyl, benzofuranyl, benzothiophenyl, benzimidazolyl, benzoxazolyl, isobenzoxazolyl, benzisoxazolyl, benzthiazolyl, benzisothiazolyl, isobenzofuranyl, indolyl, isoindolyl, indolizinyl, indolinyl, isoindolinyl, indazolyl, pyrazolopyridinyl, pyrazolopyrimidinyl, imidazopyridinyl, imidazopyrazinyl, imidazopyridazinyl; each of which may be optionally substituted with one, two, or three substituents each independently selected from the group consisting of halo, —CN, —OR¹⁸, —NR$^{19a}$R$^{19b}$, and C$_{1-4}$alkyl optionally substituted with a substituent selected from the group consisting of fluoro, —CN, —OR²⁰, —NR$^{21a}$R$^{21b}$, and —C(=O)NR$^{21a}$R$^{21b}$; and
Het² is a non-aromatic heterocyclyl optionally substituted with one, two, or three substituents each independently selected from the group consisting of halo, —CN, —OR¹⁸, —NR$^{19a}$R$^{19b}$, and C$_{1-4}$alkyl optionally substituted with a substituent selected from the group consisting of fluoro, —CN, —OR²⁰, —NR$^{21a}$R$^{21b}$, and —C(=O)NR$^{21a}$R$^{21b}$;
wherein
R¹⁸, R$^{19a}$, R$^{19b}$, R²⁰, R$^{21a}$, and R$^{21b}$ are each independently selected from the group consisting of hydrogen; C$_{1-4}$alkyl optionally substituted with a substituent selected from the group consisting of fluoro and —C(=O)NR$^{22a}$R$^{22b}$; and C$_{2-4}$alkyl substituted with a substituent selected from the group consisting of —OR²³ and —NR$^{22a}$R$^{22b}$; wherein
R$^{22a}$, R$^{22b}$ and R²³ are each independently selected from the group consisting of hydrogen; C$_{1-4}$alkyl; and C-linked 4- to 7-membered non-aromatic heterocyclyl containing at least one nitrogen, oxygen or sulfur atom.

3. The compound according to claim 1, wherein
(a) L² is selected from the group consisting of >SO$_2$, >CR$^{4a}$R$^{4b}$, and —CHR$^{4a}$CHR⁵—; wherein
R$^{4a}$ is selected from the group consisting of hydrogen; —C(=O)NR$^{7a}$R$^{7b}$;
C$_{1-4}$alkyl optionally substituted with a substituent selected from the group consisting of fluoro, —CN, —OR⁸, and —NR$^{9a}$R$^{9b}$; and C-linked 4- to 7-membered non-aromatic heterocyclyl containing at least one nitrogen, oxygen or sulfur atom;
R$^{4b}$ is selected from the group consisting of hydrogen and methyl; or
R$^{4a}$ and R$^{4b}$ together with the carbon atom to which they are attached form a C$_{3-5}$cycloalkyl or a C-linked 4- to 6-membered heterocyclyl containing an oxygen atom;
R⁵ is selected from the group consisting of hydrogen; —OR⁶; —NR$^{7a}$R$^{7b}$;
C(=O)NR$^{7a}$R$^{7b}$; C$_{1-4}$alkyl optionally substituted with a substituent selected from the group consisting of fluoro, —CN, —OR⁸, and —NR$^{9a}$R$^{9b}$; and C-linked 4- to 7-membered non-aromatic heterocyclyl containing at least one nitrogen, oxygen or sulfur atom; wherein
R⁶, R$^{7a}$, R$^{7b}$, R⁸, R$^{9a}$ and R$^{9b}$ are each independently selected from the group consisting of hydrogen; C$_{1-4}$alkyl optionally substituted with a substituent selected from the group consisting of fluoro, —CN and —C(=O)NR$^{10a}$R$^{10b}$; and
C$_{2-4}$alkyl substituted with a substituent selected from the group consisting of —OR¹¹ and —NR$^{10a}$R$^{10b}$; wherein
R$^{10a}$, R$^{10b}$ and R¹¹ are each independently selected from the group consisting of hydrogen and C$_{1-4}$alkyl; and
R³ is selected from the group consisting of Ar; Het¹; Het²; and a 7- to 10-membered saturated spirocarbobicyclic system; or (b) L² is selected from >CR⁴ᶜR⁴ᵈ, and —CHR⁴ᶜCHR⁵ᵃ—; wherein R⁴ᶜ, R⁴ᵈ and R⁵ᵃ are each independently selected from the group consisting of hydrogen; and
C₁₋₄alkyl; and
R³ is selected from the group consisting of

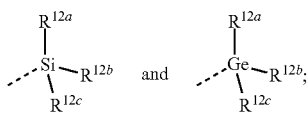

wherein
R¹²ᵃ, R¹²ᵇ, and R¹²ᶜ are each independently selected from the group consisting of C₁₋₆alkyl optionally substituted with a —OH or a —NH₂ substituent; or
(c) -L²-R³ is C₁₋₆alkyl optionally substituted with one, two or three fluoro substituents; or
(d) -L²-R³ is

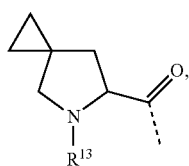

wherein R¹³ is hydrogen; or
(e) -L²-R³ is

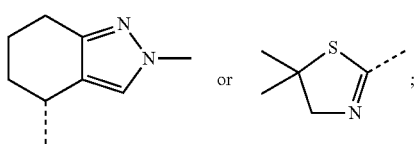

and wherein
Ar is phenyl optionally substituted with one, two, or three substituents each independently selected from the group consisting of halo, —CN, and C₁₋₄alkyl optionally substituted with a substituent selected from the group consisting of fluoro, —CN, —OR²⁰, —NR²¹ᵃR²¹ᵇ, and —C(=O)NR²¹ᵃR²¹ᵇ;
Het¹ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, and C₁₋₄alkyl optionally substituted with a substituent selected from the group consisting of fluoro, —CN, —OR²⁰, —NR²¹ᵃR²¹ᵇ, and
—C(=O)NR²¹ᵃR²¹ᵇ; and
Het² is a non-aromatic heterocyclyl selected from azetidinyl, pyrrolidinyl and piperidinyl; wherein
R²⁰, R²¹ᵃ, and R²¹ᵇ are each independently selected from the group consisting of hydrogen and C₁₋₄alkyl.

4. The compound according to claim 1, wherein
R¹ is CF₃;
(a) L² is >CR⁴ᵃR⁴ᵇ; wherein
R⁴ᵃ is selected from the group consisting of hydrogen; —C(=O)NR⁷ᵃR⁷ᵇ;
C₁₋₄alkyl; and C-linked 4- to 7-membered non-aromatic heterocyclyl containing at least one nitrogen, oxygen or sulfur atom; and
R⁴ᵇ is selected from the group consisting of hydrogen and methyl; wherein
R⁷ᵃ and R⁷ᵇ are each independently selected from the group consisting of hydrogen;
C₁₋₄alkyl; and C₂₋₄alkyl substituted with a substituent selected from the group consisting of —OR¹¹ and —NR¹⁰ᵃR¹⁰ᵇ; wherein
R¹⁰ᵃ, R¹⁰ᵇ and R¹¹ are each independently selected from the group consisting of hydrogen and C₁₋₄alkyl; and
R³ is selected from the group consisting of Ar; Het¹; and a 7- to 10-membered saturated spirocarbobicyclic system; or
(b) L² is >CR⁴ᶜR⁴ᵈ, wherein R⁴ᶜ and R⁴ᵈ are each independently selected from the group consisting of hydrogen; and C₁₋₄alkyl; and
R³ is selected from the group consisting of

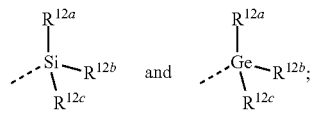

wherein
R¹²ᵃ, R¹²ᵇ, and R¹²ᶜ are each independently selected from the group consisting of C₁₋₆alkyl optionally substituted with a —NH₂ substituent; or
(c) -L²-R³ is C₁₋₆alkyl optionally substituted with one, two or three fluoro substituents; or
(d) -L²-R³ is

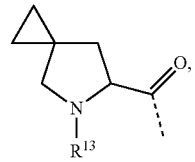

wherein R¹³ is hydrogen; or
(e) -L²-R³ is

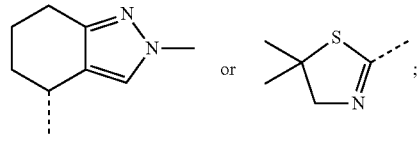

and wherein
Ar is phenyl optionally substituted with a halo substituent; and
Het¹ is a monocyclic heteroaryl selected from the group consisting of pyridyl, 4-, 5- or 6-pyrimidinyl, pyrazinyl, pyridazinyl, pyrrolyl, pyrazolyl, imidazolyl, and 4- or 5-thiazolyl; each of which may be optionally substituted with one or two substituents each independently selected from the group consisting of halo and $C_{1-4}$alkyl optionally substituted with a substituent selected from the group consisting of —CN, —OR$^{20}$, —NR$^{21a}$R$^{21b}$, and —C(=O)NR$^{21a}$R$^{21b}$; wherein R$^{20}$, R$^{21a}$, and R$^{21b}$ are each independently selected from the group consisting of hydrogen and $C_{1-4}$alkyl.

5. The compound according to claim 1, wherein
R$^1$ is CF$_3$;
L$^1$ is a 7- to 9-membered fused heterocycle of Formula (a) as defined in any one of claims 1 to 3, wherein
m is equal to 0 or 1;
n is equal to 0 or 1;
p is 1 and q is 0;
R is hydrogen; and
(a) L$^2$ is >CH$_2$; and R$^3$ is Ar; or Het$^1$; or
(b) L$^2$ is >CH$_2$; and R$^3$ is .... Ge(—R$^{12b}$)(R$^{12c}$)R$^{12a}$;

wherein R$^{12a}$, R$^{12b}$, and R$^{12c}$ are each independently selected from $C_{1-6}$alkyl; or
(c) -L$^2$-R$^3$ is $C_{1-6}$alkyl optionally substituted with one, two or three fluoro substituents; wherein
Ar is phenyl optionally substituted with a halo substituent; and
Het$^1$ is a monocyclic heteroaryl selected from the group consisting of pyridyl, 4-, 5- or 6-pyrimidinyl, pyrazinyl, pyridazinyl, pyrrolyl, pyrazolyl, and 4- or 5-thiazolyl; each of which may be optionally substituted with a halo or a $C_{1-4}$alkyl substituent.

6. The compound according to claim 1, wherein
R$^1$ is CF$_3$;
R$^2$ is hydrogen;
L$^1$ is a 8- to 9-membered fused heterocycle of Formula (a-1) or (a-2)

(a-1)

(a-2)

(a) L$^2$ is >CH$_2$; and R$^3$ is Ar; or Het$^1$; or
(b) L$^2$ is >CH$_2$; and R$^3$ is —Ge(CH$_3$)$_3$; wherein
Ar is phenyl optionally substituted with a halo substituent; and
Het$^1$ is a monocyclic heteroaryl selected from the group consisting of pyridyl, 4-, 5- or 6-pyrimidinyl, pyrrolyl, pyrazolyl, and 4- or 5-thiazolyl; each of which may be optionally substituted with a halo or a $C_{1-4}$alkyl substituent.

7. The compound according to claim 1, wherein
R$^1$ is selected from the group consisting of CF$_3$;
R$^2$ is selected from the group consisting of hydrogen;
-L$^2$-R$^3$ is selected from (a), (b), (c) or (d) wherein
(a) L$^2$ is selected from the group consisting of >SO$_2$, >CR$^{4a}$R$^{4b}$, and —CHR$^{4a}$CHR$^5$—; wherein
R$^{4a}$ is selected from the group consisting of hydrogen and $C_{1-4}$alkyl;
R$^{4b}$ is hydrogen; o
R$^5$ is selected from the group consisting of hydrogen and $C_{1-4}$alkyl; and
R$^3$ is selected from the group consisting of Ar; Het$^1$; and Het$^2$; or
(b) L$^2$ is >CR$^{4c}$R$^{4d}$; wherein R$^{4c}$ and R$^{4d}$ are hydrogen; and
R$^3$ is .... Ge(—R$^{12b}$)(R$^{12c}$)R$^{12a}$;

wherein
R$^{12a}$, R$^{12b}$, and R$^{12c}$ are $C_{1-6}$alkyl; or
(c) -L$^2$-R$^3$ is $C_{1-6}$alkyl optionally substituted with one, two or three fluoro or —OH substituents; or
(d) -L$^2$-R$^3$ is wherein
R$^{13}$ is hydrogen; and
R$^{13a}$ is hydrogen;
R$^{13b}$ hydrogen; or
R$^{13a}$ and R$^{13b}$ are bound to the same carbon atom and together form a $C_{3-5}$cycloalkyl;
Ar is phenyl which may be optionally substituted with one, two, or three substituents each independently selected from halo;
Het$^1$ is a monocyclic heteroaryl selected from the group consisting of pyridyl, 4-, 5- or 6-pyrimidinyl, pyrazinyl, pyridazinyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^{18}$, —NR$^{19a}$R$^{19b}$, $C_{3-6}$cycloalkyl, and $C_{1-4}$alkyl optionally substituted with a substituent selected from the group consisting of —OR$^{20}$, and —NR$^{21a}$R$^{21b}$; and
Het$^2$ is a non-aromatic heterocyclyl optionally substituted with one, two, or three substituents each independently selected from the group consisting of halo, —OR$^{18}$, —C(=O)—O—$C_{1-6}$alkyl, —C(=O)—Ar$^2$, —C(=O)—Het$^3$, and —C(=O)—Het$^4$;
Ar$^2$ is phenyl;
Het$^3$ is pyridyl;
Het$^4$ is oxetanyl, or tetrahydropyranyl;

wherein
R$^{18}$, R$^{20}$, R$^{21a}$ and R$^{21b}$ are each independently selected from the group consisting of hydrogen; and C$_{1-4}$alkyl.

8. The compound according to claim 1, wherein at least one of m, n, q and p is different from 0.

9. A pharmaceutical composition comprising a compound as claimed in claim 1 and a pharmaceutically acceptable carrier or diluent.

10. A process for preparing a pharmaceutical composition comprising mixing a pharmaceutically acceptable carrier or diluent with a therapeutically effective amount of a compound according to claim 1.

* * * * *